US012735705B2

(12) United States Patent
Sawamoto et al.

(10) Patent No.: US 12,735,705 B2
(45) Date of Patent: Sep. 15, 2026

(54) COMPOUND, METHOD AND PHARMACEUTICAL COMPOSITION FOR REGULATING EXPRESSION OF ATAXIN 3

(71) Applicant: TANABE PHARMA CORPORATION, Osaka (JP)

(72) Inventors: Hiroaki Sawamoto, Osaka (JP); Takuya Higo, Osaka (JP); Shumpei Murata, Osaka (JP); Tomo Araki, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 740 days.

(21) Appl. No.: 17/998,463

(22) PCT Filed: May 12, 2021

(86) PCT No.: PCT/JP2021/018040
§ 371 (c)(1),
(2) Date: Nov. 10, 2022

(87) PCT Pub. No.: WO2021/230286
PCT Pub. Date: Nov. 18, 2021

(65) Prior Publication Data

US 2023/0227824 A1 Jul. 20, 2023

(30) Foreign Application Priority Data

May 12, 2020 (JP) ................................ 2020-083864

(51) Int. Cl.
*C12N 15/113* (2010.01)
*A61K 31/7115* (2006.01)
*A61K 31/7125* (2006.01)
*A61P 25/28* (2006.01)

(52) U.S. Cl.
CPC ........ *C12N 15/113* (2013.01); *A61K 31/7115* (2013.01); *A61K 31/7125* (2013.01); *A61P 25/28* (2018.01); *C12N 2310/11* (2013.01)

(58) Field of Classification Search
CPC .................................................... C12N 15/113
See application file for complete search history.

(56) References Cited

U.S. PATENT DOCUMENTS

2015/0315595 A1 11/2015 Uzcategui et al.
2019/0247420 A1 8/2019 Freier et al.
2022/0002336 A1 1/2022 Sawamoto et al.

FOREIGN PATENT DOCUMENTS

EP 3 351 548 A1 7/2018
EP 3 881 851 A1 9/2021
JP 2015-511821 A 4/2015
JP 2019-534009 A 11/2019
WO WO 2008/018795 A1 2/2008
WO WO 2009/099326 A1 8/2009
(Continued)

OTHER PUBLICATIONS

JP2018-212424 machine translation, pp. 1-215 (Year: 2018).*
(Continued)

*Primary Examiner* — Ekaterina Poliakova-Georgantas
(74) *Attorney, Agent, or Firm* — Finnegan, Henderson, Farabow, Garrett & Dunner, LLP

(57) ABSTRACT

A modified oligonucleotide having an activity of inhibiting Ataxin 3 expression and having any one of the following nucleobase sequences or a nucleobase sequence of 17 contiguous bases contained in the nucleobase sequences:

(1) TCGGGTAAGTAGATTTTC, (SEQ ID NO: 239)
(2) GAAGTATCTGTAGGCCTA, (SEQ ID NO: 240)
(3) GGACTGTATAGGAGATTA, (SEQ ID NO: 241)
(4) GGTTATAGGATGCAGGTA, (SEQ ID NO: 242)
(5) AGGTTATAGGATGCAGGT, (SEQ ID NO: 243)
(6) GAAGCTAAGTAGGTGACT, (SEQ ID NO: 244)
(7) TGAAGCTAAGTAGGTGAC, (SEQ ID NO: 245)
(8) CCTAGTCACTTTGATAGA, (SEQ ID NO: 246)
(9) GGAACATCTTGAGTAGGT, (SEQ ID NO: 247)
(10) GGTGTTCAGGGTAGATGT, (SEQ ID NO: 248)
(11) GGATACTCTGCCCTGTTC, (SEQ ID NO: 249)
(12) GGTGTCAAACGTGTGGTT, (SEQ ID NO: 250)
(13) CCGTGTGCTAGTATTTGT, (SEQ ID NO: 251)
(14) TAGTAGAGTTTTGCTTGG, (SEQ ID NO: 252)
(15) GATGTAGTAGAGTTTTGC, (SEQ ID NO: 253)
(16) TGATGTAGTAGAGTTTTG, (SEQ ID NO: 254)
(17) CTGATGTAGTAGAGTTTT, (SEQ ID NO: 255)

(Continued)

-continued

(19) GCAAGTTGGTTTGTGGTA, (SEQ ID NO: 256)

(20) TCTAGGCAATTGTGGTGG, (SEQ ID NO: 257)

(21) GTAACTCTGCACTTCCCA, (SEQ ID NO: 258)

(22) GTCATCCCTATGTCTTAT, (SEQ ID NO: 259)

(23) GTCATATGGTCAGGGTAT, (SEQ ID NO: 260)

(24) TGTCATATGGTCAGGGTA, (SEQ ID NO: 261)

(25) ATGTCATATGGTCAGGGT, (SEQ ID NO: 262)
and

(26) TATGTCATATGGTCAGGG. (SEQ ID NO: 263)

19 Claims, No Drawings

Specification includes a Sequence Listing.

(56) References Cited

FOREIGN PATENT DOCUMENTS

| | | | |
|---|---|---|---|
| WO | WO 2011/156202 | A1 | 12/2011 |
| WO | WO 2013/138353 | A2 | 9/2013 |
| WO | WO 2013/138353 | A3 | 9/2013 |
| WO | WO 2015/053624 | A2 | 4/2015 |
| WO | WO 2015/053624 | A3 | 4/2015 |
| WO | WO 2017/053781 | A1 | 3/2017 |
| WO | WO 2018/002886 | A1 | 1/2018 |
| WO | WO 2018/089805 | A1 | 5/2018 |
| WO | WO 2019/217708 | A1 | 11/2019 |
| WO | WO 2020/100826 | A1 | 5/2020 |
| WO | WO 2020/172559 | A1 | 8/2020 |

OTHER PUBLICATIONS

Partial Supplementary European Search Report issued Apr. 15, 2024 in European Patent Application No. 21805226.4, 17 pages.

International Search Report issued Jul. 13, 2021 in PCT/JP2021/018040 filed on May 12, 2021, 4 pages.

Takiyama et al., "The gene for Machado-Joseph disease maps to human chromosome 14q", Nature Genetics, vol. 4, 1993, pp. 300-304.

Kawaguchi et al., "CAG expansions in a novel gene for Machado-Joseph disease at chromosome 14q32.1", Nature Genetics, vol. 8, 1994, pp. 221-228.

Takiyama et al., "Machado-Joseph disease: Cerebellar ataxia and autonomic dysfunction in a patient with the shortest known expanded allele (56 CAG repeat units) of the MJD1 gene", Neurology, 49, 1997, pp. 604-606.

Evers et al., "Ataxin-3 Protein and RNA Toxicity in Spinocerebellar Ataxia Type 3: Current Insights and Emerging Therapeutic Strategies", Molecular Neurobiology, 49, 2014, pp. 1513-1531.

Aartsma-Rus, "FDA Approval of Nusinersen for Spinal Muscular Atrophy Makes 2016 the Year of Splice Modulating Oligonucleotides" Nucleic Acid Therapeutics, vol. 27, No. 2, 2017, pp. 67-69.

McLoughlin et al., "Oligonucleotide Therapy Mitigates Disease in Spinocerebellar Ataxia Type 3 Mice", Annals of Neurology, vol. 84, No. 1, 2018, pp. 64-77.

Moore et al., "Evaluation of Antisense Oligonucleotides Targeting ATXN3 in SCA3 Mouse Models", Molecular Therapy Nucleic Acids, Jun. 16, 2017, vol. 7, pp. 200-210.

Extended European Search Report issued Jul. 16, 2024, in corresponding European Patent Application No. 21805226.4, 19 pages.

Database Geneseq, Mar. 8, 2018, "ATXN3 gene editing single-molecule gRNA spacer, SEQ ID:10152.", XP002811816, retrieved from EBI accession No. GSN:BEV05448 Database accession No. BEV05448.

* cited by examiner

COMPOUND, METHOD AND PHARMACEUTICAL COMPOSITION FOR REGULATING EXPRESSION OF ATAXIN 3

CROSS-REFERENCE TO RELATED APPLICATIONS

This application is a national stage application of International Application No. PCT/JP2021/018040, filed May 12, 2021, which is based upon and claims the benefit of priority to Japanese Patent Application No. 2020-083864, filed May 12, 2020. The entire contents of these applications are incorporated herein by reference.

TECHNICAL FIELD

The present invention relates to a compound for reducing at least one of a pre-mRNA level, an mRNA level and a protein level of Ataxin 3 (ATXN3) in an animal, a method using the compound, and a pharmacological composition containing the compound. The method of the prevent invention is useful for treating, preventing, or delaying progression of ATXN3-related diseases, such as spinocerebellar ataxia type 3 (also referred to as SCA3, Machado-Joseph disease, or MJD).

TECHNICAL BACKGROUND

Spinocerebellar degeneration type 3 is a most common type of autosomal dominant hereditary spinocerebellar degeneration. This disease develops at an average age of 36 years, and initially, nystagmus, increased deep tendon reflex, articulation disorder, and the like appear. After that, the condition gradually worsens, and symptoms such as difficulty in walking, dysphagia, eye paralysis, and compound eyes appear, and the patient dies in about 20 years due to aspiration pneumonia, a fall accident, or the like. There is no curative treatment for controlling the progression of the condition. There are only symptomatic treatments for motor dysfunction, extrapyramidal disorders, painful muscle spasms or depression, and fatigue, and rehabilitation treatments for controlling the progression of the condition.

A responsible gene for spinocerebellar ataxia type 3 was reported in 1993 to be linked to $14q_{2}4.3\text{-}q_{3}2$ (Non-Patent Document 1: Takiyama et al., Nature Genetics, 1993, 4, 300-304). Subsequently, in 1994, CAG repeat expansion was observed in a novel gene ATXN3 (or MJD1), and it was identified as a responsible gene (Non-Patent Document 2: Kawaguchi et al., Nature Genetics, 1994, 8, 221-228). This CAG repeat is from 14 to 37 for normal alleles, whereas it is from 61 to 84 for expansion alleles (Non-Patent Document 3: Takiyama et al., Neurology, 1997, 49, 604-606), and it has been reported that there is a negative correlation between CAG repeat expansion and age of onset (Non-Patent Document 2: Kawaguchi et al., Nature Genetics, 1994, 8, 221-228). It is considered that CAG repeat elongation causes motor dysfunction following cerebellar Purkinje cell dysfunction and shedding as a result of various pathological hypotheses such as mitochondrial disorders, transcriptional abnormalities, calcium homeostasis abnormalities, autophagy abnormalities, and axonal transport abnormalities due to its own RNA toxicity or its translation product, polyglutamine (Non-Patent Document 4: M. M. Evers et al., Molecular Neurobiology, 2014, 49, 1513-1531).

Antisense oligonucleotides have been clinically applied one after another as an effective means for regulating expression of certain gene products. In recent years, it has been clarified that it shows a very excellent effect also on central genetic diseases such as spinraza (Non-Patent Document 5: Aartsma-Rus, A., Nucleic Acid Ther., 2017, 27, 67). Antisense oligonucleotides may therefore prove to be useful in several therapeutic, diagnostic, and research applications for regulating ATXN3 mRNA.

So far, attempts have been made to develop a radical treatment for spinocerebellar ataxia type 3 using antisense oligonucleotides. DE KIMPE et al. attempted to selectively reduce expression of abnormal alleles with antisense oligonucleotides targeting a CAG repeat moiety in an ATXN3 coding region (Patent Document 1: WO 2008/018795, and Patent Document 2: WO 2009/099326). Further, UZCATEGUI et al. also attempted to selectively reduce expression of abnormal alleles by preparing an antisense oligonucleotide complementary to a region containing a single nucleotide polymorphism (G987C) common to some patients with spinocerebellar ataxia type 3 (Patent Document 3: WO 2013/138353). VAN ROON-MOM et al. reported an antisense oligonucleotide complementary to ATXN3 mRNA that exon-skips exons 10 and 9 in which CAG repeats are present (Patent Document 4: WO 2015/053624). However, these four reported cases only verified effects of antisense oligonucleotides on a very limited region of ATXN3 mRNA, and no efficacy has been reported in a genetically modified animal model (spinocerebellar ataxia type 3 animal model). In recent years, exploration of antisense oligonucleotides has been performed allele non-selectively with respect to an entire ATXN3 mRNA region, and, for example, allele non-selectively, antisense oligonucleotides have been reported (Patent Document 5: WO 2018/089805, Patent Document 6: WO 2019/217708, and Patent Document 7: WO 2020/172559), and efficacy for a genetically modified animal model (spinocerebellar ataxia type 3 animal model) has been confirmed (Non-Patent Document 6: Hayley S. McLoughlin et al., Annals of Neurology, 2018, 84, 64-77). However, a medicinal dose in this case is 700 μg per mouse, which does not hold a sufficient medicinal potential for clinical applications. As described above, although development of antisense oligonucleotides for a radical treatment of spinocerebellar ataxia type 3 has been vigorously carried out, these have not been sufficiently effective.

RELATED ART

Patent Document

[Patent Document 1] WO 2008/018795
[Patent Document 2] WO 2009/099326
[Patent Document 3] WO 2013/138353
[Patent Document 4] WO 2015/053624
[Patent Document 5] WO 2018/089805
[Patent Document 6] WO 2019/217708
[Patent Document 7] WO 2020/172559

Non-Patent Documents

[Non-Patent Document 1] Takiyama et al., Nature Genetics 1993, 4, 300-304
[Non-Patent Document 2] Kawaguchi et al., Nature Genetics 1994, 8, 221-228.
[Non-Patent Document 3] Takiyama et al., Neurology 1997, 49, 604-606
[Non-Patent Document 4] M. M. Evers et al., Molecular Neurobiology, 2014, 49, 1513-1531
[Non-Patent Document 5] Aartsma-Rus, A. Nucleic Acid Ther., 2017, 27, 67

[Non-Patent Document 6] Hayley S. McLoughlin et al., Annals of Neurology, 2018, 84, 64-77

SUMMARY OF THE INVENTION

Problems to be Solved by the Invention

An object of the present invention is to provide a compound, a method and a pharmaceutical composition for inhibiting ATXN3 expression and/or for treating, preventing, delaying or ameliorating an ATXN3-related disease.

Means for Solving the Problems

The present inventors have conducted intensive studies and found a modified oligonucleotide that strongly inhibits ATXN3 expression, and thus have accomplished the present invention.

A summary of the present invention is as follows.

[1] A modified oligonucleotide having an activity of inhibiting Ataxin 3 (ATXN3) expression, wherein a nucleobase sequence of the modified oligonucleotide is a nucleobase sequence selected from a group consisting of (1) TCGGGTAAGTAGATTTTC (complementary sequence of 2159-2176 of SEQ ID NO: 1) (SEQ ID NO: 239 of the sequence listing), (2) GAAGTATCTGTAGGCCTA (complementary sequence of 2513-2530 of SEQ ID NO: 1) (SEQ ID NO: 240 of the sequence listing), (3) GGACTGTATAGGAGATTA (complementary sequence of 2646-2663 of SEQ ID NO: 1) (SEQ ID NO: 241 of the sequence listing), (4) GGTTATAGGATGCAGGTA (complementary sequence of 5844-5861 of SEQ ID NO: 1) (SEQ ID NO: 242 of the sequence listing), (5) AGGTTATAGGATGCAGGT (complementary sequence of 5845-5862 of SEQ ID NO: 1) (SEQ ID NO: 243 of the sequence listing), (6) GAAGCTAAGTAGGTGACT (complementary sequence of 15115-15132 of SEQ ID NO: 1) (SEQ ID NO: 244 of the sequence listing), (7) TGAAGCTAAGTAGGTGAC (complementary sequence 15116-15133 of SEQ ID NO: 1) (SEQ ID NO: 245 of the sequence listing), (8) CCTAGTCACTTTGATAGA (complementary sequence of 19163-19180 of SEQ ID NO: 1) (SEQ ID NO: 246 of the sequence listing), (9) GGAACATCTTGAGTAGGT (complementary sequence of 19737-19754 of SEQ ID NO: 1) (SEQ ID NO: 247 of the sequence listing),

(10) GGTGTTCAGGGTAGATGT (complementary sequence of 20835-20852 of SEQ ID NO: 1) (SEQ ID NO: 248 of the sequence listing),

(11) GGATACTCTGCCCTGTTC (complementary sequence of 21482-21499 of SEQ ID NO: 1) (SEQ ID NO: 249 of the sequence listing),

(12) GGTGTCAAACGTGTGGTT (complementary sequence of 22200-22217 of SEQ ID NO: 1) (SEQ ID NO: 250 of the sequence listing),

(13) CCGTGTGCTAGTATTTGT (complementary sequence of 27389-27406 of SEQ ID NO: 1) (SEQ ID NO: 251 of the sequence listing),

(14) TAGTAGAGTTTTGCTTGG (complementary sequence of 31570-31587 of SEQ ID NO: 1) (SEQ ID NO: 252 of the sequence listing),

(15) GATGTAGTAGAGTTTTGC (complementary sequence of 31574-31591 of SEQ ID NO: 1) (SEQ ID NO: 253 of the sequence listing),

(16) TGATGTAGTAGAGTTTTG (complementary sequence of 31575-31592 of SEQ ID NO: 1) (SEQ ID NO: 254 of the sequence listing),

(17) CTGATGTAGTAGAGTTTT (complementary sequence of 31576-31593 of SEQ ID NO: 1) (SEQ ID NO: 255 of the sequence listing),

(19) GCAAGTTGGTTTGTGGTA (complementary sequence of 32008-32025 of SEQ ID NO: 1) (SEQ ID NO: 256 of the sequence listing),

(20) TCTAGGCAATTGTGGTGG (complementary sequence of 32127-32144 of SEQ ID NO: 1) (SEQ ID NO: 257 of the sequence listing),

(21) GTAACTCTGCACTTCCCA (complementary sequence of 36411-36428 of SEQ ID NO: 1) (SEQ ID NO: 258 of the sequence listing),

(22) GTCATCCCTATGTCTTAT (complementary sequence of 36607-36624 of SEQ ID NO: 1) (SEQ ID NO: 259 of the sequence listing),

(23) GTCATATGGTCAGGGTAT (complementary sequence of 40453-40470 of SEQ ID NO: 1) (SEQ ID NO: 260 of the sequence listing),

(24) TGTCATATGGTCAGGGTA (complementary sequence of 40454-40471 of SEQ ID NO: 1) (SEQ ID NO: 261 of the sequence listing),

(25) ATGTCATATGGTCAGGGT (complementary sequence of 40455-40472 of SEQ ID NO: 1) (SEQ ID NO: 262 of the sequence listing), and

(26) TATGTCATATGGTCAGGG (complementary sequence of 40456-40473 of SEQ ID NO: 1) (SEQ ID NO: 263 of the sequence listing) (in the present specification, a base sequence is described in an order of from 5' to 3') or a nucleobase sequence of 17 contiguous bases contained in the nucleobase sequence.

[2] The modified oligonucleotide of [1], being single-stranded.

[3] The modified oligonucleotide of [1] or [2], wherein at least one nucleoside forming the modified oligonucleotide contains a modified sugar.

[4] The modified oligonucleotide of [3], wherein the modified sugar is selected from a group consisting of a bicyclic sugar, a 2'-MOE (2'-O-methoxyethyl) modified sugar, and a 2'-OMe modified sugar.

[5] The modified oligonucleotide of [4], wherein the bicyclic sugar is selected from sugar moieties of LNA, GuNA, ALNA[Ms], ALNA[mU], ALNA[ipU], ALNA [Oxz], or ALNA[Trz].

[6] The modified oligonucleotide of any one of [1]-[5], wherein at least one nucleoside forming the modified oligonucleotide contains a modified nucleobase.

[7] The modified oligonucleotide of [6], wherein the modified nucleobase is 5-methylcytosine.

[8] The modified oligonucleotide of any one of [1]-[7], wherein at least one internucleoside linkage forming the modified oligonucleotide is a modified internucleoside linkage.

[9] The modified oligonucleotide of [8], wherein the modified internucleoside linkage is a phosphorothioate internucleoside linkage.

[10] The modified oligonucleotide of any one of [1]-[9], comprising:

(1) a gap segment;

(2) a 5' wing segment; and (3) a 3' wing segment, wherein the gap segment is positioned between the 5' wing segment and the 3' wing segment, and nucleosides forming the 5' wing segment and the 3' wing segment each contain a modified sugar.

[11] A modified oligonucleotide having an activity of inhibiting ATXN3 expression and consisting of 12-24 residues, wherein a nucleobase sequence of the modified oligonucleotide has a complementarity of at least 85% to an equal length portion of a nucleobase sequence of SEQ ID NO: 1 in the sequence listing, and at least one of nucleosides forming the oligonucleotide has a modified sugar selected from sugar moieties of ALNA[Ms], ALNA[mU], ALNA[ipU], ALNA[Oxz], or ALNA[Trz].

[12] A pharmaceutical composition comprising: the modified oligonucleotide of any one of [1]-[11] or a pharmaceutically acceptable salt thereof and a pharmaceutically acceptable carrier thereof.

[13] The pharmaceutical composition of [12], for treating, preventing, or delaying progression of an ATXN3-related disease.

[14] The pharmacological composition of [13], wherein the ATXN3-related disease is a neurodegenerative disease.

[15] The pharmacological composition of [14], wherein the neurodegenerative disease is spinocerebellar ataxia type 3.

[16] A method for treating, preventing or delaying progression of an ATXN3-related disease in a subject, comprising: administering an effective amount of the modified oligonucleotide of any one of [1]-[11] to a subject in need thereof.

[17] Use of the modified oligonucleotide of any one of [1]-[11], in production of a medicament for treating, preventing or delaying progression of an ATXN3-related disease.

[18] The modified oligonucleotide of any one of [1]-[11] for treating, preventing or delaying progression of an ATXN3-related disease.

Effect of the Invention

According to the present invention, a symptom of an ATXN3-related disease, for example, spinocerebellar ataxia type 3, can be ameliorated, and an effective medicament for prevention or treatment of the disease is provided. The modified oligonucleotide of the present invention has an excellent activity of inhibiting ATXN3 expression and has few side effects such as toxicity, and thus, is excellent as an active ingredient for prevention or treatment of an ATXN3-related disease.

MODE FOR CARRYING OUT THE INVENTION

It is to be understood that both the foregoing summary and the following detailed description are exemplary and explanatory only and are not restrictive of the present invention as claimed. In the present specification, unless specifically stated otherwise, the use of a singular form includes a plural form. As used herein, the use of the term "including" and its other forms, such as "includes" and "included," is not limiting. Further, unless specifically stated otherwise, the term "element" or the like includes an element that includes one unit and an element that includes more than one subunit.

Section headings used herein are for organizational purposes only and should not be construed as limiting the subject matter described. All documents or portions of documents cited in this application, including, but not limited to, patents, patent applications, reports, books and articles, are expressly incorporated herein by reference, with respect to the portions of the document discussed herein, and in their entirety.

Definitions

Unless a specific definition is given, the nomenclature used in connection with analytical chemistry, synthetic organic chemistry, and medical chemistry and pharmaceutical chemistry, and their procedures and techniques described herein are those that are well known in the art and are commonly used. Standard techniques can be used for chemical synthesis and chemical analysis as used herein. Where permitted, all patents, patent applications, published patent applications and other publications referred to throughout the disclosure of this specification, and GenBank accession numbers and relevant sequence information as well as other data available through databases such as the National Center for Biotechnology Information (NCBI), are incorporated by reference with respect to portions of the documents discussed herein, and in its entirety.

Further, this specification is filed together with a sequence listing in electronic format. However, the information of the sequence listing described in the electronic format is incorporated herein by reference in its entirety.

Unless otherwise indicated, the following terms have the following meanings.

A "nucleobase" means a heterocyclic moiety that can pair with a base of another nucleic acid.

A "nucleobase sequence" means an order of contiguous nucleobases forming the oligonucleotide of the present invention.

A "nucleoside" means a molecule in which a sugar and a nucleobase are linked. In certain embodiments, a nucleoside is linked to a phosphate group.

A "nucleotide" means a molecule in which a phosphate group is linked to a sugar moiety of a nucleoside. In a naturally occurring nucleotide, a sugar moiety is a ribose or deoxyribose and is covalently linked by a phosphodiester bond via a phosphate group.

An "oligomer compound" or "oligomer" refers to a polymer of linked monomeric subunits that is capable of hybridizing to at least one region of a nucleic acid molecule.

An "oligonucleotide" means a polymer of nucleosides in which nucleosides and internucleoside linkages are linked independently of each other.

An "internucleoside linkage" refers to a chemical bond between nucleosides.

A "naturally occurring internucleoside linkage" means a 3'-5'phosphodiester linkage.

A "modified internucleoside linkage" refers to a substitution or any change from a naturally occurring internucleoside linkage (that is, a phosphodiester internucleoside linkage). For example, there is a phosphorothioate internucleoside linkage, but it is not limited to this.

A "phosphorothioate internucleoside linkage" means an internucleoside linkage in which a phosphodiester linkage is modified by replacing one of non-crosslinked oxygen atoms with a sulfur atom. A phosphorothioate linkage is one example of the modified internucleoside linkage.

A "modified nucleobase" refers to any nucleobase other than adenine, cytosine, guanine, thymidine or uracil. For example, there is a 5-methylcytosine, but it is not limited to this. "Unmodified nucleobases" means purine bases adenine (A) and guanine (G), and pyrimidine bases thymine (T), cytosine (C) and uracil (U).

A "modified oligonucleotide" means an oligonucleotide that contains at least one of the modified nucleoside and/or the modified internucleoside linkage.

"Salt" is a generic term for compounds in which one or more dissociable hydrogen ions contained in an acid are replaced by cations such as metal ions and ammonium ions, and examples of salts of a modified oligonucleotide include, but not limited to, salts (for example, a sodium salt, and a magnesium salt) formed with inorganic ions (for example, sodium ions, and magnesium ions) on phosphorothioates or phosphodiesters or on functional groups (for example, an amino group) in a modified nucleobase.

A "sugar" or a "sugar moiety" means a natural sugar moiety or a modified sugar moiety.

A "modified sugar" refers to a substitution or change from a natural sugar. Examples of modified sugars include a substituted sugar moiety and a bicyclic sugar.

A "substituted sugar moiety" means a furanosyl other than a natural sugar of RNA or DNA.

A "bicyclic sugar" means a furanosyl ring modified by crosslinking of two different carbon atoms present on the same ring. A "bicyclic nucleic acid" refers to a nucleoside or nucleotide in which a furanose moiety of the nucleoside or nucleotide contains a "bicyclic sugar."

A "single-stranded oligonucleotide" means an oligonucleotide that is not hybridized to a complementary strand.

"ATXN3" means a nucleic acid or protein that is also known as Ataxin 3. ATXN3 may include, for example, various splicing variants transcribed from the ATXN3 gene, single nucleotide polymorphism (SNP) or CAG repeat expansion.

"Complementary" means an ability with respect to pairing between nucleobases of a first nucleic acid and a second nucleic acid. In certain embodiments, adenine is complementary to thymidine or uracil. In certain embodiments, cytosine is complementary to guanine. In certain embodiments, 5-methylcytosine is complementary to guanine.

"Fully complementary (also called complementarity)" or "100% complementary (also called complementarity)" means that all nucleobases in a nucleobase sequence of a first nucleic acid have complementary nucleobases in a second nucleobase sequence of a second nucleic acid. In certain embodiments, a first nucleic acid is a modified oligonucleotide and a target nucleic acid is a second nucleic acid.

"Mismatch" or "non-complementary nucleobase" refers to a case where a nucleobase of a first nucleic acid cannot pair with a corresponding nucleobase of a second nucleic acid or a target nucleic acid.

A "target nucleic acid," a "target RNA" and a "target RNA transcript" all refer to a nucleic acid that can be targeted by a modified oligonucleotide. In certain embodiments, a target nucleic acid includes a region of an ATXN3 mRNA or an ATXN3 pre-mRNA.

"Motif" means a combination of chemically distinct regions in a modified oligonucleotide.

"Immediately adjacent" means that there is no intervening element between immediately adjacent elements.

A "pharmaceutically acceptable salt" means a physiologically and pharmaceutically acceptable salt of the modified oligonucleotide of the present invention, that is, a salt that retains a desired biological activity of a modified oligonucleotide and does not impart an undesired toxic effect to the modified oligonucleotide.

"Administering" means providing a drug to an animal, and examples thereof include, but are not limited to, administering by a medical professional or family member, and self-administering.

"Amelioration" refers to a lessening of at least one indicator, sign, or symptom of a related disease, disorder, or condition. Severity of an indicator can be determined by a subjective or objective measure that is known to a person skilled in the art.

"Animals" refers to humans or non-human animals, including, but not limited to, mice, rats, rabbits, dogs, cats, pigs, and non-human primates, including, but not limited to, monkeys and chimpanzees.

An "effective amount" means an amount of the modified oligonucleotide of the present invention that is sufficient to achieve a desired physiological outcome in an individual in need of the drug. The effective amount can vary from individual to individual depending on the health and physical conditions of the individual to be treated, the taxonomic group of the individual to be treated, the formulation of the composition, assessment of the individual's medical condition, and other relevant factors.

An "individual" means a human or non-human animal selected for treatment or therapy.

"Preventing" means delaying or preventing the onset or development of a disease, disorder, unfavorable health condition, or one or more symptoms associated with the disease, disorder or undesired health condition for a period of time from minutes to indefinitely. Preventing also means reducing a risk of developing a disease, disorder, or undesirable health condition.

"Treating" means alleviating or eliminating a disease, disorder, or unfavorable health condition, or one or more symptoms associated with the disease, disorder, or unfavorable condition, or partially eliminating or eradicating one or more causes of the disease, disorder, or unfavorable health condition itself.

Specific Embodiments

Certain specific embodiments described below provide, but are not limited to, a compound for inhibiting expression of ATXN3, a method using the compound, and a pharmaceutical composition containing the compound.

(1) Modified Oligonucleotide

A modified oligonucleotide of the present invention (hereinafter, may be referred to as "the compound of the present invention" or "the modified oligonucleotide of the present invention") is an antisense oligonucleotide of ATXN3 having an activity of inhibiting ATXN3 expression. Inhibiting ATXN3 expression (level) in the present invention means suppressing at least one of a pre-mRNA level transcribed from the ATXN3 gene, an mRNA level spliced from pre-mRNA, and an ATXN3 protein level translated from mRNA. ATXN3 pre-mRNA may contain CAG repeat expansion found in patients with SNP and/or spinocerebellar ataxia type 3. However, an example thereof is that represented by a sequence (SEQ ID NO: 1 in the sequence listing) described in NC_000014.9: c92106621-92058552 *Homo sapiens* chromosome 14, $GRCH_38$.p13 Primary Assembly. ATXN3 mRNA may contain at least one of CAG repeat expansions found in patients with variant, SNP and spinocerebellar ataxia type 3. However, an example thereof is that represented by a sequence (SEQ ID NO: 2 in the sequence listing) described in GenBank accession number NM 004993.5. SEQ ID NOs: 1 and 2 show DNA base sequences.

However, in the case of RNA sequences, T is replaced with U.

A degree of inhibition of ATXN3 expression of the compound of the present invention may be any degree as long as at least one of the pre-mRNA level, the pre-mRNA level and the protein level of ATXN3 is lower than when the compound is not administered, and as a result, prevention and/or amelioration of symptoms associated with an ATXN3-related disease is observed. However, specifically, for example, in an in vitro ATXN3 expression measurement method to be described later, after the compound of the present invention is brought into contact with cells, the ATXN3 expression level is at least 70% or less, preferably 50% or less, more preferably 40% or less, even more preferably 30% or less, and particularly preferably 20% or less as compared to a case of non-contact or contact with a negative control substance.

The compound of the present invention is a modified oligonucleotide consisting of 12-24 residues, preferably 16-18 residues, and more preferably 18 residues and having an activity of inhibiting ATXN3 expression, and may be any compound as long as the compound includes at least 8 contiguous nucleobase sequences complementary to an equal length portion of any one of positions 256-273, positions 404-427, positions 541-558, positions 647-665, positions 697-716, positions 767-784, positions 2043-2066, positions 2092-2109, positions 2159-2177, positions 2502-2530, positions 2646-2667, positions 4011-4029, positions 4038-4063, positions 4259-4292, positions 5179-5196, positions 5762-5777, positions 5843-5870, positions 7203-7225, positions 7535-7553, positions 7602-7617, positions 7741-7758, positions 7788-7810, positions 10273-10288, positions 10997-11014, positions 11642-11672, positions 11734-11759, positions 11799-11825, positions 12710-12727, positions 13136-13156, positions 14325-14340, positions 15114-15139, positions 15703-15723, positions 18108-18123, positions 18749-18766, positions 19061-19078, positions 19163-19181, positions 19355-19372, positions 19736-19756, positions 20833-20854, positions 21059-21077, positions 21482-21502, positions 22109-22126, positions 22192-22220, positions 22913-22930, positions 22998-23013, positions 23046-23074, positions 24651-24670, positions 26470-26485, positions 27388-27412, positions 30559-30582, positions 31570-31595, positions 31841-31858, positions 32006-32029, positions 32127-32144, positions 33630-33647, positions 35710-35729, positions 36411-36441, positions 36607-36624, positions 37690-37705, positions 38556-38576, positions 38587-38624, positions 40452-40492, positions 40539-40557, positions 41281-41300, positions 41392-41410, positions 42805-42820, positions 43091-43106, or positions 45892-45909 from the 5' end of the nucleobase sequence of SEQ ID NO: 1 in the sequence listing (hereinafter this is referred to as an "ATXN3 complementary nucleobase sequence"). Further, the above ATXN3 complementary nucleobase sequence is preferably 8-18 contiguous nucleobase sequences, and more preferably 16, 17 or 18 contiguous nucleobase sequences.

Or, the ATXN3 complementary nucleobase sequence may be 16 or more contiguous nucleobase sequences complementary to an equal length portion of any one of positions 1512-1536, positions 1568-1583, positions 3931-3946, positions 5668-5683, positions 7817-7832, positions 9925-9940, positions 10409-10424, positions 10556-10571, positions 10584-10599, positions 11002-11017, positions 11617-11632, positions 12076-12091, positions 14074-14089, positions 14213-14228, positions 16211-16226, positions 16740-16755, positions 18015-18030, positions 18033-18048, positions 20832-20847, positions 20848-20863, positions 22116-22131, positions 22194-22225, positions 27062-27077, positions 27271-27286, positions 29393-29408, positions 30535-30550, positions 30556-30571, positions 30930-30945, positions 33237-33252, positions 34900-34915, positions 35841-35856, positions 41294-41309, positions 42110-42125, positions 43182-43197, positions 43209-43233, positions 43933-43948, or positions 44050-44065 from the 5' end of the sequence of SEQ ID NO: 1 in the sequence listing.

Here, the modified oligonucleotide of the present invention may have, in addition to the above ATXN3 complementary nucleobase sequence, an additional sequence on the 5' end side and/or the 3' end side as long as its total length is in a range of 12-24 residues, preferably 16-18 residues, and more preferably 18 residues and the full-length nucleobase sequence has a complementarity of at least 85% to an equal length portion of the nucleobase sequence of SEQ ID NO: 1 in the sequence listing. Further, the addition sequence may be any sequence as long as the modified oligonucleotide of the present invention has an activity of inhibiting ATXN3 expression.

The full-length nucleobase sequence of the modified oligonucleotide has a complementarity of at least 85% to an equal length portion of SEQ ID NO: 1 in the sequence listing. However, the complementarity is preferably 90%, more preferably 95%, and even more preferably 100%. Here, an equal length portion means a portion detected as a portion having homology between the nucleobase sequence of the modified oligonucleotide of the present invention and a nucleobase sequence of ATXN3 pre-mRNA or mRNA when the nucleobase sequences are aligned, for example, using software such as BLAST, Genetyx software (GENETYX CORPORATION). That is, the nucleobase sequence of the oligonucleotide of the present invention is desirably fully complementary to an equal length portion of a nucleobase sequence of ATXN3 pre-mRNA or mRNA, but may have one or more mismatched nucleobases, and those having a complementarity of 85% or more, 90% or more, and preferably 95% or more are used.

The mismatched nucleobases may be contiguous or may be interspersed with an ATXN3 complementary nucleobase sequence. Percent complementarity of the antisense oligonucleotide of the present invention with respect to ATXN3 pre-mRNA or mRNA can be determined conventionally, for example, using the BLAST program (basic local alignment search tools) and the PowerBLAST program (Altschul et al., J. Mol. Biol., 1990, 215, 403 410; Zhang and Madden, Genome Res., 1997, 7, 649 656), and the Genetyx software (GENETYX CORPORATION), which are known in the art. Percent homology, sequence identity, or complementarity, can be determined, for example, by the Gap program (Wisconsin Sequence Analysis Package, Version 8 for Unix, Genetics Computer Group, University Research Park, Madison Wis.), by using default settings using the algorithm of Smith and Waterman (Adv. Appl. Math., 1981, 2, 482 489), and by using the Genetyx software (GENETYX CORPORATION). For example, 18 of 20 nucleobases of a modified oligonucleotide are complementary to an equal length portion of ATXN3 pre-mRNA, and when hybridized, the modified oligonucleotide has a 90 percent complementarity.

A method for verifying the activity of the compound of the present invention may be any method as long as the method can verify that the compound of the present invention inhibits ATXN3 expression. However, specifically, for example, the in vitro ATXN3 expression measurement method to be described later is used.

Examples of thus selected modified oligonucleotide of the present invention include those consisting of a sequence complementary to a nucleobase sequence selected from any one of positions 256-273, positions 404-421, positions 405-422, positions, 407-424, positions 408-425, positions 409-426, positions 410-427, positions 541-558, positions 647-664, positions 648-665, positions 697-714, positions 698-715, positions 699-716, positions 767-784, positions 1512-1527, positions 1521-1536, positions 1568-1583, positions 2043-2060, positions, 2045-2062, positions 2046-2063, positions 2047-2064, positions, 2048-2065, positions 2051-2066, positions 2092-2109, positions 2159-2176, positions, 2162-2177, positions 2502-2519, positions 2513-2530, positions, 2646-2663, positions 2650-2667, positions 3931-3946, positions 4011-4028, positions 4012-4029, positions 4038-4053, positions 4041-4058, positions 4046-4063, positions 4259-4274, positions 4267-4284, positions 4268-4285, positions 4269-4286, positions 4277-4292, positions 5179-5196, positions 5668-5683, positions 5762-5777, positions 5843-5860, positions 5844-5861, positions, 5845-5862, positions 5853-5870, positions 7203-7220, positions 7208-7225, positions 7535-7552, positions 7536-7553, positions 7602-7617, positions 7741-7758, positions 7788-7805, positions 7792-7809, positions 7793-7810, positions 7817-7832, positions 9925-9940, positions 10273-10288, positions 10409-10424, positions 10556-10571, positions 10584-10599, positions 10997-11014, positions 11002-11017, positions 11617-11632, positions 11642-11659, positions 11643-11660, positions 11644-11661, positions 11645-11662, positions 11646-11663, positions 11648-11665, positions 11649-11666, positions 11650-11665, positions 11650-11667, positions 11651-11668, positions 11654-11669, positions 11655-11672, positions 11734-11751, positions 11735-11752, positions 11738-11753, positions 11741-11758, positions 11744-11759, positions 11799-11816, positions 11800-11817, positions 11810-11825, positions 12076-12091, positions 12710-12727, positions 13136-13153, positions 13141-13156, positions 14074-14089, positions 14213-14228, positions 14325-14340, positions 15114-15129, positions 15115-15132, positions 15116-15133, positions 15124-15139, positions 15703-15720, positions 15704-15721, positions 15705-15722, positions, 15706-15723, positions 16211-16226, positions 16740-16755, positions, 18015-18030, positions 18033-18048, positions 18108-18123, positions 18749-18766, positions 19061-19078, positions 19163-19180, positions 19166-19181, positions 19355-19372, positions 19736-19753, positions 19737-19754, positions 19738-19755, positions 19739-19756, positions 20832-20847, positions 20833-20850, positions 20835-20852, positions 20836-20853, positions 20837-20854, positions 20838-20855, positions 20839-20854, positions 20848-20863, positions 21059-21076, positions 21060-21077, positions 21482-21499, positions 21483-21500, positions 21487-21502, positions 22109-22126, positions 22116-22131, positions 22192-22209, positions 22193-22210, positions 22194-22209, positions 22194-22211, positions 22195-22212, positions 22196-22213, positions 22197-22214, positions 22197-22214, positions 22198-22215, positions 22198-22215, positions 22199-22214, positions 22199-22216, positions 22200-22217, positions 22201-22218, positions 22202-22219, positions 22203-22220, positions 22203-22218, positions 22210-22225, positions 22913-22930, positions 22998-23013, positions 23046-23063, positions 23047-23064, positions 23048-23065, positions 23049-23066, positions, 23050-23067, positions 23055-23072, positions 23056-23073, positions, 23057-23074, positions 24651-24668, positions 24652-24669, positions 24653-24670, positions 26470-26485, positions 27062-27077, positions 27271-27286, positions 27388-27405, positions 27389-27406, positions 27391-27408, positions 27392-27409, positions 27393-27410, positions 27394-27411, positions 27395-27412, positions 29393-29408, positions 30535-30550, positions 30556-30571, positions 30559-30576, positions 30560-30577, positions 30561-30578, positions 30564-30581, positions 30565-30582, positions 30930-30945, positions 31570-31587, positions 31574-31591, positions 31575-31592, positions 31576-31591, positions 31576-31593, positions 31577-31594, positions 31578-31595, positions 31580-31595, positions 31841-31858, positions 32006-32021, positions 32006-32023, positions 32007-32024, positions 32008-32025, positions 32009-32026, positions 32010-32027, positions 32011-32028, positions 32012-32029, positions 32127-32144, positions 33237-33252, positions 33630-33647, positions 34900-34915, positions 35710-35725, positions 35711-35728, positions 35712-35729, positions 35841-35856, positions 36411-36428, positions 36412-36429, positions 36413-36428, positions 36413-36430, positions 36417-36432, positions 36426-36441, positions 36607-36624, positions 36609-36624, positions 37690-37705, positions 38556-38571, positions 38559-38576, positions 38587-38604, positions 38588-38605, positions 38589-38606, positions 38590-38607, positions 38593-38610, positions 38594-38611, positions 38596-38613, positions 38597-38614, positions 38598-38615, positions 38599-38616, positions 38600-38617, positions 38601-38618, positions, 38604-38621, positions 38606-38623, positions 38607-38624, positions 40452-40467, positions 40453-40470, positions 40454-40471, positions 40455-40472, positions 40456-40473, positions 40470-40485, positions 40475-40492, positions 40539-40556, positions 40540-40557, positions 41281-41298, positions 41285-41300, positions 41294-41309, positions 41392-41409, positions 41393-41410, positions 42110-42125, positions 42805-42820, positions 43091-43106, positions 43182-43197, positions 43209-43224, positions 43218-43233, positions 43933-43948, positions 44050-44065 or positions 45892-45909, preferably a nucleobase sequence selected from any one of positions 2159-2176, positions 5668-5683, positions 5845-5862, positions 11650-11665, positions 12076-12091, positions 14213-14228, positions 15115-15132, positions 16740-16755, positions 18033-18048, positions 22199-22214, positions 22203-22218, positions 27062-27077, positions 31575-31592, positions 31576-31591, positions 31576-31593, positions 32006-32021, positions 35841-35856, positions 36607-36624, positions 36609-36624, positions 37690-37705, positions 40453-40470, positions 40454-40471, positions 40455-40472, positions 40456-40473, positions 40470-40485 or positions 41294-41309, more preferably a nucleobase sequence selected from any one of positions 12076-12091, positions 22199-22214, positions, 22203-22218, positions 27062-27077, positions, 31576-31591, positions 32006-32021, positions 35841-35856, positions 36609-36624, positions 40453-40470 or positions 41294-41309, from the 5' end of the nucleobase sequence of SEQ ID NO: 1 in the sequence listing, or those consisting of a sequence complementary to a nucleobase sequence of 16 or 17 contiguous bases contained in the nucleobase sequence. Here, when a full-length nucleobase sequence of a modified oligonucleotide has 100% complementarity to an equal-length portion of the nucleobase sequence of SEQ ID NO: 1 in the sequence listing, it may have an additional sequence of 1 or 2 residues on a 5' end side and/or a 3' end side thereof.

Examples of nucleobase sequences of modified oligonucleotides, which are among the thus selected modified oligonucleotides and inhibit an ATXN3 mRNA level to 70% or less when the modified oligonucleotides are added to SH-SY5Y cells so as to have a final concentration of 3 μM using a gymnosis method as compared to a case of non-contact with the modified oligonucleotides, include those consisting of a sequence complementary to a nucleobase sequence selected from any one of positions 698-715, positions 699-716, positions 2043-2060, positions 2046-2063, positions 2047-2064, positions 2092-2109, positions 2159-2176, positions 2513-2530, positions 2646-2663, positions 2650-2667, positions 4041-4058, positions 5843-5860, positions 5844-5861, positions 5845-5862, positions 7792-7809, positions 11642-11659, positions 11643-11660, positions 11644-11661, positions 11645-11662, positions 11649-11666, positions 11650-11667, positions 11655-11672, positions 11734-11751, positions 11735-11752, positions 12710-12727, positions 13136-13153, positions 15115-15132, positions 15116-15133, positions 15704-15721, positions 15706-15723, positions 19163-19180, positions 19737-19754, positions 20835-20852, positions 20836-20853, positions 20837-20854, positions 21482-21499, positions 21483-21500, positions 22192-22209, positions 22194-22211, positions 22199-22216, positions 22200-22217, positions 22201-22218, positions 22202-22219, positions 23056-23073, positions 27388-27405, positions 27389-27406, positions 27392-27409, positions 27393-27410, positions 27394-27411, positions 30559-30576, positions 30560-30577, positions 30564-30581, positions 31570-31587, positions 31574-31591, positions 31575-31592, positions 31576-31593, positions 31577-31594, positions 31578-31595, positions 31841-31858, positions 32006-32023, positions 32007-32024, positions 32008-32025, positions 32009-32026, positions 32011-32028, positions 32127-32144, positions 35711-35728, positions 35712-35729, positions 36411-36428, positions 36412-36429, positions 36607-36624, positions 38559-38576, positions 38587-38604, positions 38588-38605, positions 38589-38606, positions 38590-38607, positions 38593-38610, positions 38594-38611, positions 38604-38621, positions 38607-38624, positions 40453-40470, positions 40454-40471, positions 40455-40472, positions 40456-40473, positions 40475-40492, positions 41281-41298, positions 41392-41409, positions 41393-41410, positions or positions 45892-45909 from the 5' end of the nucleobase sequence of SEQ ID NO: 1 in the sequence listing, or those consisting of a sequence complementary to a nucleobase sequence of 16 or 17 contiguous bases contained in the nucleobase sequence.

A specific example of the nucleobase sequence of the modified oligonucleotide of the present invention is a nucleobase sequence described in

- TCGGGTAAGTAGATTTTC (complementary sequence of 2159-2176 of SEQ ID NO: 1) (SEQ ID NO: 239 of the sequence listing),
- GAAGTATCTGTAGGCCTA (complementary sequence of 2513-2530 of SEQ ID NO: 1) (SEQ ID NO: 240 of the sequence listing),
- GGACTGTATAGGAGATTA (complementary sequence of 2646-2663 of SEQ ID NO: 1) (SEQ ID NO: 241 of the sequence listing),

- GGTTATAGGATGCAGGTA (complementary sequence of 5844-5861 of SEQ ID NO: 1) (SEQ ID NO: 242 of the sequence listing),
- AGGTTATAGGATGCAGGT (complementary sequence of 5845-5862 of SEQ ID NO: 1) (SEQ ID NO: 243 of the sequence listing),
- GAAGCTAAGTAGGTGACT (complementary sequence of 15115-15132 of SEQ ID NO: 1) (SEQ ID NO: 244 of the sequence listing),
- TGAAGCTAAGTAGGTGAC (complementary sequence 15116-15133 of SEQ ID NO: 1) (SEQ ID NO: 245 of the sequence listing),
- CCTAGTCACTTTGATAGA (complementary sequence of 19163-19180 of SEQ ID NO: 1) (SEQ ID NO: 246 of the sequence listing),
- GGAACATCTTGAGTAGGT (complementary sequence of 19737-19754 of SEQ ID NO: 1) (SEQ ID NO: 247 of the sequence listing),
- GGTGTTCAGGGTAGATGT (complementary sequence of 20835-20852 of SEQ ID NO: 1) (SEQ ID NO: 248 of the sequence listing),
- GGATACTCTGCCCTGTTC (complementary sequence of 21482-21499 of SEQ ID NO: 1) (SEQ ID NO: 249 of the sequence listing),
- GGTGTCAAACGTGTGGTT (complementary sequence of 22200-22217 of SEQ ID NO: 1) (SEQ ID NO: 250 of the sequence listing),
- CCGTGTGCTAGTATTTGT (complementary sequence of 27389-27406 of SEQ ID NO: 1) (SEQ ID NO: 251 of the sequence listing),
- TAGTAGAGTTTTGCTTGG (complementary sequence of 31570-31587 of SEQ ID NO: 1) (SEQ ID NO: 252 of the sequence listing),
- GATGTAGTAGAGTTTTGC (complementary sequence of 31574-31591 of SEQ ID NO: 1) (SEQ ID NO: 253 of the sequence listing),
- TGATGTAGTAGAGTTTTG (complementary sequence of 31575-31592 of SEQ ID NO: 1) (SEQ ID NO: 254 of the sequence listing),
- CTGATGTAGTAGAGTTTT (complementary sequence of 31576-31593 of SEQ ID NO: 1) (SEQ ID NO: 255 of the sequence listing),
- GCAAGTTGGTTTGTGGTA (complementary sequence of 32008-32025 of SEQ ID NO: 1) (SEQ ID NO: 256 of the sequence listing),
- TCTAGGCAATTGTGGTGG (complementary sequence of 32127-32144 of SEQ ID NO: 1) (SEQ ID NO: 257 of the sequence listing),
- GTAACTCTGCACTTCCCA (complementary sequence of 36411-36428 of SEQ ID NO: 1) (SEQ ID NO: 258 of the sequence listing),
- GTCATCCCTATGTCTTAT (complementary sequence of 36607-36624 of SEQ ID NO: 1) (SEQ ID NO: 259 of the sequence listing),
- GTCATATGGTCAGGGTAT (complementary sequence of 40453-40470 of SEQ ID NO: 1) (SEQ ID NO: 260 of the sequence listing),
- TGTCATATGGTCAGGGTA (complementary sequence of 40454-40471 of SEQ ID NO: 1) (SEQ ID NO: 261 of the sequence listing),
- ATGTCATATGGTCAGGGT (complementary sequence of 40455-40472 of SEQ ID NO: 1) (SEQ ID NO: 262 of the sequence listing), or
- TATGTCATATGGTCAGGG (complementary sequence of 40456-40473 of SEQ ID NO: 1) (SEQ ID NO: 263 of the sequence listing)

or a nucleobase sequence of 17 contiguous bases contained in the nucleobase sequence.

A specific example of the nucleobase sequence of the modified oligonucleotide of the present invention is preferably a nucleobase sequence described in TCGGGTAAGTAGATTTTC (complementary sequence of 2159-2176 of SEQ ID NO: 1) (SEQ ID NO: 239 of the sequence listing), AGGTTATAGGATGCAGGT (complementary sequence of 5845-5862 of SEQ ID NO: 1) (SEQ ID NO: 243 of the sequence listing), GAAGCTAAGTAGGTGACT (complementary sequence of 15115-15132 of SEQ ID NO: 1) (SEQ ID NO: 244 of the sequence listing), GTCATCCCTATGTCTTAT (complementary sequence of 36607-36624 of SEQ ID NO: 1) (SEQ ID NO: 259 of the sequence listing), GTCATATGGTCAGGGTAT (complementary sequence of 40453-40470 of SEQ ID NO: 1) (SEQ ID NO: 260 of the sequence listing), TGTCATATGGTCAGGGTA (complementary sequence of 40454-40471 of SEQ ID NO: 1) (SEQ ID NO: 261 of the sequence listing), ATGTCATATGGTCAGGGT (complementary sequence of 40455-40472 of SEQ ID NO: 1) (SEQ ID NO: 262 of the sequence listing), or TATGTCATATGGTCAGGG (complementary sequence of 40456-40473 of SEQ ID NO: 1) (SEQ ID NO: 263 of the sequence listing)

or a nucleobase sequence of 17 contiguous bases contained in the nucleobase sequence, and is more preferably a nucleobase sequence described in GTCATATGGTCAGGGTAT (complementary sequence of 40453-40470 of SEQ ID NO: 1) (SEQ ID NO: 260 of the sequence listing), or a nucleobase sequence of 17 contiguous bases contained in the nucleobase sequence.

Of these sequences, one or more cytosines may be 5-methylcytosine of a modified nucleobase to be described later. Specific examples include sequences shown in SEQ ID NO: 23, SEQ ID NO: 38, SEQ ID NO: 63, SEQ ID NO: 131, SEQ ID NO: 148, SEQ ID NO: 149, SEQ ID NO: 150 and SEQ ID NO: 151, and a preferred example is the sequence shown in SEQ ID NO: 148.

Further, examples of 16-base nucleobase sequences of the modified oligonucleotide of the present invention include sequences shown in SEQ ID NO: 264, SEQ ID NO: 179, SEQ ID NO: 265, SEQ ID NO: 266, SEQ ID NO: 192, SEQ ID NO: 267, SEQ ID NO: 268, SEQ ID NO: 204, SEQ ID NO: 269, SEQ ID NO: 214, SEQ ID NO: 220, SEQ ID NO: 270, SEQ ID NO: 271, SEQ ID NO: 228 and SEQ ID NO: 230, and preferred examples thereof include the sequences shown in SEQ ID NO: 265, SEQ ID NO: 268, SEQ ID NO: 204, SEQ ID NO: 269, SEQ ID NO: 214, SEQ ID NO: 220, SEQ ID NO: 270, SEQ ID NO: 271 and SEQ ID NO: 230.

Of these sequences, one or more cytosines may be 5-methylcytosine of a modified nucleobase to be described later. Specific examples include sequences shown in SEQ ID NO: 168, SEQ ID NO: 184, SEQ ID NO: 187, SEQ ID NO: 194, SEQ ID NO: 203, SEQ ID NO: 208, SEQ ID NO: 224, and SEQ ID NO: 225, and preferred examples include the sequences shown in SEQ ID NO: 184, SEQ ID NO: 203, SEQ ID NO: 208, SEQ ID NO: 224 and SEQ ID NO: 225.

The modified oligonucleotide of the present invention may be a double-stranded modified oligonucleotide, but a single-stranded modified oligonucleotide is preferably used.

(Modified Sugar)

As the modified oligonucleotide of the present invention, a modified oligonucleotide in which at least one nucleoside forming the modified oligonucleotide contains a modified sugar is preferably used. In the present invention, the term "modified sugar" refers to a sugar in which a sugar moiety is modified, and a modified oligonucleotide containing one or more such modified sugars has advantageous characteristics such as enhanced nuclease stability and increased binding affinity. At least one of modified sugars is preferably selected from a group consisting of a bicyclic sugar, a 2'-MOE modified sugar, and a 2'-OMe modified sugar. Examples of bicyclic sugars include, as illustrated below, sugar moieties of LNA, GuNA, ALNA[Ms], ALNA[mU], ALNA[ipU], ALNA[Oxz], or ALNA[Trz], and the sugar moiety of ALNA[Ms] is preferably used.

Examples of substituted sugar moieties include, but are not limited to, nucleosides containing 5'-vinyl, 5'-methyl (R or S), 4'-S, 2'-F, 2'-$OCH_3$(2'-OMe), 2'-$OCH_2CH_3$, 2'-$OCH_2CH_2F$, and 2'-O $(CH_2)_2OCH_3$(2'-MOE) substituent groups. The substituent at the 2' position can be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$ and O—$CH_2$—C(═O)—$N(R_l)$—$(CH_2)_2$—$N(R_m)(R_n)$ (wherein $R_l$, $R_m$ and $R_n$ are each independently H or substituted or unsubstituted $C_1$-$C_{10}$ alkyl).

Examples of nucleosides having a bicyclic sugar include, but are not limited to, nucleosides that contain a crosslink between the 4' and the 2' ribosyl ring atoms. In certain embodiments, an oligonucleotide provided herein includes a nucleoside having one or more bicyclic sugars, in which a crosslink includes one of the following formulas: 4'-$(CH_2)$—O-2' (LNA); 4'-$(CH_2)$—S-2; 4'-$(CH_2)_2$—O-2' (ENA); 4'-$CH(CH_3)$—O-2' and 4'-$CH(CH_2OCH_3)$—O-2' (and analogs thereof, see U.S. Pat. No. 7,399,845); 4'-C$(CH_3)(CH_3)$—O-2' (and analogs thereof, see WO 2009/006478); 4'-$CH_2$—$N(OCH_3)$-2' (and analogs thereof; see WO 2008/150729); 4'-$CH_2$—O—$N(CH_3)$-2' (and analogs thereof; see US 2004-0171570); 4'-$CH_2$—N(R)—O-2' (wherein R is H, $C_1$-$C_{12}$ alkyl or a protecting group) (see U.S. Pat. No. 7,427,672); 4'-$CH_2$—$C(H)(CH_3)$-2' (and analogs thereof; see Chattopadhyaya et al., J. Org. Chem., 2009, 74, 118-134); and 4'-$CH_2$—C(═$CH_2$)-2' (and analogues thereof; see WO 2008/154401).

Additional nucleosides having a bicyclic sugar are reported in published literatures (see, for example: Srivastava et al., J. Am. Chem. Soc., 2007, 129 (26) 8362-8379; Frieden et al., Nucleic Acids Research, 2003, 21, 6365-6372; Elayadi et al., Curr. Opinion Invens. Drugs, 2001, 2, 558-61; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A., 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al.; U.S. Pat. Nos. 7,399,845; 6,770,748; 6,525,191; 6,268,490; US 2008-0039618; US 2007-0287831; US 2004-0171570; US 2009-0012281; WO 2010/036698; WO 2009/067647; WO 2009/067647; WO 2007/134181; WO 2005/021570; WO 2004/106356; WO 94/14226; WO 2009/006478; WO 2008/154401; and WO 2008/150729). The above-described nucleosides having a bicyclic sugar each can be prepared having one or more optically active sugar configurations including, for example, an α-L-ribofuranose and a β-D-ribofuranose.

GuNA, a nucleoside having a bicyclic sugar, has been reported as an artificial nucleoside having a guanidine crosslink (see WO 2014/046212 and WO 2017/047816). Bicyclic nucleosides ALNA[Ms], ALNA[mU], ALNA[ipU], ALNA[Trz] and ALNA[Oxz] have been reported as cross-linked artificial nucleic acid amino LNA (ALNA) (see International Application PCT/JP 2019/044182 (WO 2020/100826)).

In certain embodiments, a nucleoside having a bicyclic sugar includes a crosslink between 4' and 2' carbon atoms of a pentofuranosyl sugar moiety, and a crosslink is included that contains 1 or 1 to 4 linking groups that are each independently selected from, but are not limited to, —[C$(R_a)(R_b)]_n$—, —$C(R_a)$═$C(R_b)$—, —$C(R_a)$═N—, —C(═$NR_a$)—, —C(═O)—, —C(═S)—, —$N(R_a)$—, —O—, —$Si(R_a)_2$— and —$S(═O)_x$—, wherein: X is 0, 1, or 2; n is 1, 2, 3, or 4; $R_a$ and $R_b$ are each, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, an aromatic ring group, a substituted aromatic ring group, a heterocyclic group, a substituted heterocyclic group, a $C_5$-$C_7$ alicyclic group, a substituted $C_5$-$C_7$ alicyclic group, halogen, $OJ_1$, $NJ_1J_2$, $SJ_1$, $N_3$, $COOJ_1$, acyl (C(═O)—H), substituted acyl, CN, sulfonyl ($S(═O)_2$-$J_1$) or sulfoxyl (S(═O)-$J_1$), $J_1$ and $J_2$ are each independently H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, an aromatic ring group, a substituted aromatic ring group, acyl (C(═O)—H), substituted acyl, a heterocyclic group, a substituted heterocyclic group, $C_1$-$C_{12}$ aminoalkyl, substituted $C_1$-$C_{12}$ aminoalkyl or a protecting group.

In certain embodiments, the crosslink of the bicyclic sugar moiety is $[C(R_a)(R_b)]_n$—, —$[CR_a)$ $(R_b)]_n$—O—, —$C(R_aR_b)$—N(R)—O— or —$C(R_aR_b)$—O—N(R)—. In certain embodiments, the crosslink is 4'-$CH_2$-2', 4'-$(CH_2)_2$-2', 4'-$(CH_2)_3$-2', 4'-$CH_2$—O-2' (the nucleoside having a bicyclic sugar in this case is also referred to as LNA), 4'-$(CH_2)_2$—O-2', 4'-$CH_2$—O—N(R)-2' and 4'-$CH_2$—N(R)—O-2'-, wherein each R is, independently, H, a protecting group or $C_1$-$C_{12}$ alkyl.

In certain embodiments, the crosslink of the bicyclic sugar moiety is 4'-$CH_2$—O-2'-(LNA) or —$CH_2$—N(R)—, wherein each R is independently —$SO_2$—$CH_3$ (ALNA[Ms]), —CO—NH—$CH_3$ (ALNA[mU]), 1,5-dimethyl-1,2,4-triazol-3-yl (ALNA[Trz]), —CO—NH—$CH(CH_3)_2$ (ALNA[ipU]), or 5-methyl-2,4-oxadiazol-3-yl (ALNA[Oxz]) (International Application PCT/JP 2019/044182 (WO 2020/100826)).

In certain embodiments, a nucleoside having a bicyclic sugar is further defined by an isomeric steric configuration. For example, a nucleoside containing a 4'-$(CH_2)$—O-2' crosslink may exist in an α-L-steric configuration or a β-D-steric configuration.

In certain embodiments, nucleosides having a bicyclic sugar include those having a 4'-2' crosslink, and examples of such crosslinks include, but are not limited to, α-L-4'-$(CH_2)$—O-2', β-D-4'-$CH_2$—O-2', 4'-$(CH_2)_2$—O-2', 4'-$CH_2$—O—N(R)-2', 4'-$CH_2$—N(R)—O-2', 4'-$CH(CH_3)$—O-2', 4'-$CH_2$—S-2', 4'-$CH_2$—$CH(CH_3)$-2', and 4'-$(CH_2)_3$-2' (wherein, R is H, a protecting group, $C_1$-$C_{12}$ alkyl, or urea or guanidine that may be substituted with $C_1$-$C_{12}$ alkyl).

In certain embodiments, a nucleoside having a bicyclic sugar has the following formula:

[Chemical Formula 1]

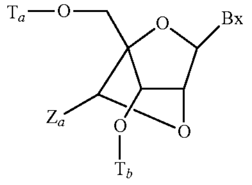

wherein

Bx is a heterocyclic base moiety;

$T_a$ and $T_b$ are each independently a hydrogen atom, a protecting group of a hydroxyl group, a phosphate group that may be substituted, a phosphorus moiety, a covalent attachment to a support, or the like; and $Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In certain embodiments, the substituents are each independently monosubstituted or polysubstituted with a substituent independently selected from halogen, oxo, hydroxyl, $OJ_c$, $NJ_cJ_d$, $SJ_c$, $N_3$, OC(═X)$J_c$ and $NJ_e$C(═X)$NJ_cJ_d$ (wherein $J_c$, $J_d$ and $J_e$ are each independently H, $C_1$-$C_6$ alkyl or substituted $C_1$-$C_6$ alkyl; and X is O or $NJ_c$).

In certain embodiments, a nucleoside having a bicyclic sugar has the following formula:

[Chemical Formula 2]

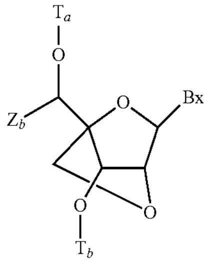

wherein

Bx is a heterocyclic base moiety;

$T_a$ and $T_b$ are each independently a hydrogen atom, a protecting group of a hydroxyl group, a phosphate group that may be substituted, a phosphorus moiety, a covalent attachment to a support, or the like; and $Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(═O)—).

In certain embodiments, a nucleoside having a bicyclic sugar has the following formula:

[Chemical Formula 3]

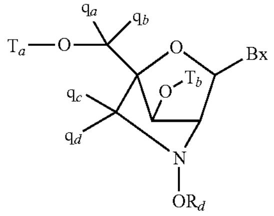

wherein

Bx is a heterocyclic base moiety;

$T_a$ and $T_b$ are each independently a hydrogen atom, a protecting group of a hydroxyl group, a phosphate group that may be substituted, a phosphorus moiety, a covalent attachment to a support, or the like;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and $q_a$, $q_b$, $q_c$ and $q_d$ are each independently H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl.

In certain embodiments, a nucleoside having a bicyclic sugar has the following formula:

[Chemical Formula 4]

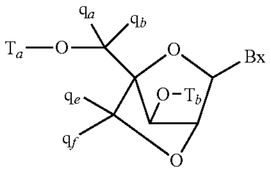

wherein

Bx is a heterocyclic base moiety;

$T_a$ and $T_b$ are each independently a hydrogen atom, a protecting group of a hydroxyl group, a phosphate group that may be substituted, a phosphorus moiety, a covalent attachment to a support, or the like; and $q_a$, $q_b$, $q_e$ and $q_f$ are each independently hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)-NJ_jJ_k$ or $N(H)C(=S)NJ_jJ_k$;

or $q_e$ and $q_f$ are both $=C(q_g)(q_h)$; and $q_g$ and $q_h$ are each independently H, halogen, $C_1$-$C_{12}$ alkyl or substituted $C_1$-$C_{12}$ alkyl.

Synthesis and preparation of adenine, cytosine, guanine, 5-methyl-cytosine, thymine and uracil bicyclic nucleoside (also referred to as LNA), which have 4'-$CH_2$—O-2' bridges, are described along with their oligomerization and nucleic acid recognition properties (Koshkin et al., Tetrahedron, 1998, 54, 3607-3630). Synthesis of a nucleoside having a bicyclic sugar is also described in WO 98/39352 and WO 99/14226.

Various analogs of bicyclic nucleosides having 4'-2' bridging groups such as 4'-$CH_2$—O-2' (the bicyclic nucleoside in this case is also referred to as LNA) and 4'-$CH_2$—S-2' have also been prepared (Kumar et al., Bioorg. Med. Chem. Lett., 1998, 8, 2219-2222). Preparation of oligodeoxyribonucleotide duplexes containing bicyclic nucleosides for use as substrates for nucleic acid polymerases has also been described (Wengel et al., WO 99/14226). Further, synthesis of 2'-amino-LNA (the bicyclic nucleoside in this case is also referred to as ALNA), that is, a conformationally restricted high-affinity oligonucleotide analog, has been described in the art (Singh et al., J. Org. Chem., 1998, 63, 10035-10039). Further, 2'-amino- and 2'-methylamino-LNAs have been prepared and thermal stability of duplexes with complementary RNA and DNA strands has been previously reported.

In certain embodiments, a nucleoside having a bicyclic sugar has the following formula:

[Chemical Formula 5]

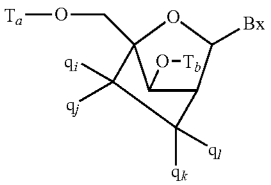

wherein

Bx is a heterocyclic base moiety;

$T_a$ and $T_b$ are each independently a hydrogen atom, a protecting group of a hydroxyl group, a phosphate group that may be substituted, a phosphorus moiety, a covalent attachment to a support, or the like; and $q_i$, $q_j$, $q_k$ and $q_l$ are each independently H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

$q_i$ and $q_j$ or $q_l$ and $q_k$ are both $=C(q_g)(q_h)$, wherein $q_g$ and $q_h$ are each independently H, halogen, $C_1$-$C_{12}$ alkyl or substituted $C_1$-$C_{12}$ alkyl.

One carbocyclic bicyclic nucleoside having a 4'-$(CH_2)_3$-2' crosslink and the alkenyl analog crosslink 4'-CH═CH—$CH_2$-2' have been described (Frier et al., Nucleic Acids Research, 1997, 25 (22), 4429-4443, and Albaek et al., J. Org. Chem., 2006, 71, 7731-7740). Synthesis and preparation of carbocyclic bicyclic nucleosides is also described, along with their oligomerization and biochemical studies (Srivastava et al., J. Am. Chem. Soc. 2007, 129 (26), 8362-8379).

In certain embodiments, examples of nucleosides having a bicyclic sugar include, but are not limited to, compounds such as those shown below.

[Chemical Formula 6]

(A)

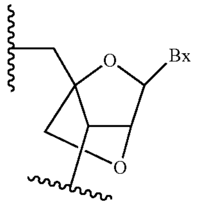

(B)

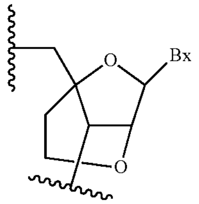

-continued (C)

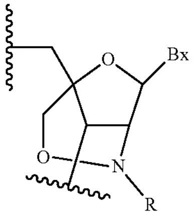

(D)

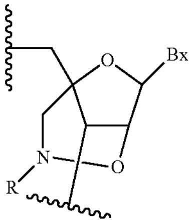

(E)

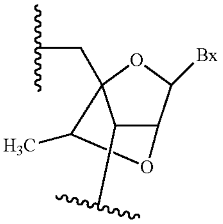

(F)

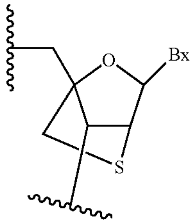

(G)

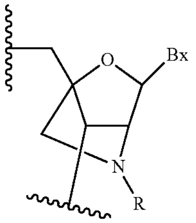

(H)

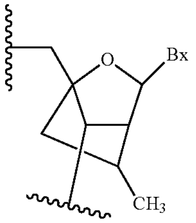

-continued (I)

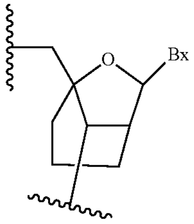

(J)

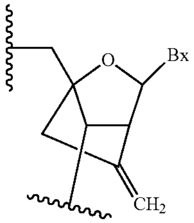

wherein Bx is a base moiety; and R is independently a protecting group, $C_1$-$C_6$ alkyl or $C_1$-$C_6$ alkoxy.

In certain embodiments (LNA), examples of a nucleoside having a bicyclic sugar include nucleosides represented by the following formula:

[Chemical Formula 7]

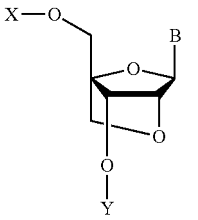

[wherein

B is a nucleobase; and

X and Y are each independently a hydrogen atom, a protecting group of a hydroxyl group, a phosphate group that may be substituted, a phosphorus moiety, a covalent attachment to a support, or the like] (see WO 98/39352]. A typical example is a nucleotide represented by the following formula:

[Chemical Formula 8]

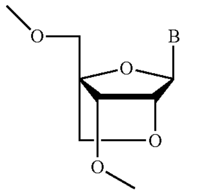

In certain embodiments (GuNA), a nucleoside containing a bicyclic sugar is a nucleoside represented by the following general formula:

[Chemical Formula 9]

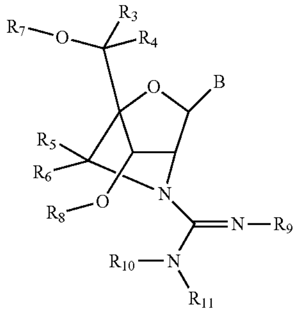

[wherein B is a nucleobase; $R_3$, $R_4$, $R_5$, and $R_6$ are each independently a hydrogen atom or a $C_{1-6}$ alkyl group that may be substituted with one or more substituents;

$R_7$ and $R_8$ are each independently a hydrogen atom, a protecting group of a hydroxyl group, a phosphate group that may be substituted, a phosphorus moiety, a covalent attachment to a support, or the like; and $R_9$, $R_{10}$, and $R_{11}$ are each independently a hydrogen atom, a $C_{1-6}$ alkyl group that may be substituted with one or more substituents, or a protecting group of an amino group] (see, for example, WO 2014/046212, and WO 2017/047816).

In certain embodiments (ALNA [mU]), a nucleoside containing a bicyclic sugar is a nucleoside represented by the following general formula (I):

[Chemical Formula 10]

(I)

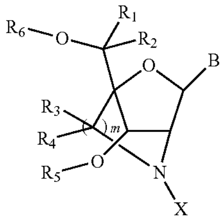

[wherein

B is a nucleobase;

$R_1$, $R_2$, $R_3$, and $R_4$ are each independently a hydrogen atom or a $C_{1-6}$ alkyl group that may be substituted with one or more substituents;

$R_5$ and $R_6$ are each independently a hydrogen atom, a protecting group of a hydroxyl group, a phosphate group that may be substituted, a phosphorus moiety, a covalent attachment to a support, or the like;

m is 1 or 2; and

X is a group represented by the following formula (II-1):

[Chemical Formula 11]

(II-1)

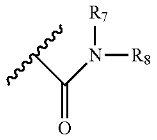

the symbol

[Chemical Formula 12]

described in the formula (II-1) represents a point of attachment to a 2'-amino group; and one of $R_7$ and $R_8$ is a hydrogen atom and the other is a methyl group that may be substituted with one or more substituents] (see, for example, International Application PCT/JP2019/044182 (WO 2020/100826)). A typical specific example is a nucleoside in which one of $R_7$ and $R_8$ is a hydrogen atom and the other is an unsubstituted methyl group.

In certain embodiments (ALNA[ipU]), a nucleoside containing a bicyclic sugar is a nucleoside having the general formula (I) as defined in ALNA[mU] above, wherein X is a group represented by the following formula (II-1):

[Chemical Formula 13]

(II-1)

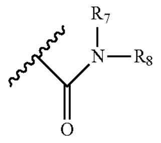

one of $R_7$ and $R_8$ is a hydrogen atom and the other is an isopropyl group that may be substituted with one or more substituents (see, for example, International Application PCT/JP2019/044182 (WO 2020/100826)). A typical specific example is a nucleoside in which one of $R_7$ and $R_8$ is a hydrogen atom and the other is an unsubstituted isopropyl group.

In certain embodiments (ALNA [Trz]), a nucleoside containing a bicyclic sugar is a nucleoside having the above general formula (I), wherein X is a group represented by the following formula (II-2):

[Chemical Formula 14]

(II-2)

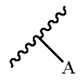

wherein A is a triazolyl group that may be substituted with one or more substituents (see, for example, International Application PCT/JP2019/044182 (WO 2020/100826)). A typical example of ALNA [Trz] is a nucleoside in which A is a triazolyl group that may have one or more methyl groups, more specifically, a 1,5-dimethyl-1,2,4-triazol-3-yl group.

In certain embodiments (ALNA[Oxz]), it is a nucleoside having the general formula (I) defined in ALNA[mU] above, wherein X is a group represented by the following formula (II-2):

[Chemical Formula 15]

(II-2)

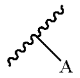

and A is an oxadiazolyl group that may be substituted with one or more substituents (see, for example, International Application PCT/JP2019/044182 (WO 2020/100826)). A typical specific example is a nucleoside or nucleotide in which A is an oxadiazolyl group that may have one or more methyl groups, more specifically, a 5-methyl-1,2,4-oxadiazol-3-yl group.

In certain embodiments (ALNA [Ms]), a nucleoside containing a bicyclic sugar is a nucleoside having the above general formula (I), wherein X is a group represented by the following general formula (II-3):

[Chemical Formula 16]

(II-3)

and M is a sulfonyl group substituted with a methyl group that may be substituted with one or more substituents (see, for example, International Application PCT/JP2019/044182 (WO 2020/100826)). A typical specific example of ALNA[Ms] is a nucleoside in which Mis a sulfonyl group substituted with an unsubstituted methyl group.

In certain embodiments, a nucleoside is modified by replacement of a ribosyl ring with a sugar surrogate. Examples of such modifications include, but are not limited to, replacements of a ribosyl ring with a substitute ring system (sometimes referred to as a DNA analog), for example, a morpholino ring, a cyclohexenyl ring, a cyclohexyl ring or a tetrahydropyranyl ring, and, for example, those having one of the following formulas:

[Chemical Formula 17]

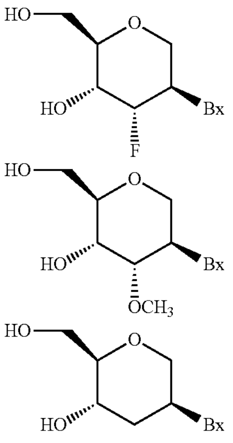

In certain embodiments, a sugar surrogate having the following formula is selected:

[Chemical Formula 18]

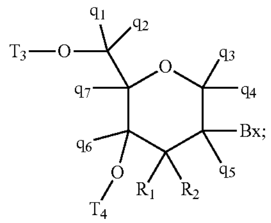

wherein

Bx is a heterocyclic base moiety;

$T_3$ and $T_4$ are each independently an internucleoside linking group linking a tetrahydropyran nucleoside analog to an oligomeric compound; or one of $T_3$ and $T_4$ is an internucleoside linking group linking a tetrahydropyran nucleoside analog to an oligomeric compound or an oligonucleotide, and the other of $T_3$ and $T_4$ is H, a hydroxyl protecting group, a linking conjugate group or a 5' or 3'-terminal group;

$q_1$, $q_2$, $q_3$, $q_4$, $q_5$, $q_6$ and $q_7$ are each independently H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is hydrogen, and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN (wherein X is O, S or $NJ_1$; and $J_1$, $J_2$ and $J_3$ are each independently H or $C_1$-$C_6$ alkyl).

In certain embodiments, $q_1$, $q_2$, $q_3$, $q_4$, $q_5$, $q_6$, and $q_7$ are each H. In certain embodiments, at least one of $q_1$, $q_2$, $q_3$, $q_4$, $q_5$, $q_6$, and $q_7$ is other than H. In certain embodiments, at least one of $q_1$, $q_2$, $q_3$, $q_4$, $q_5$, $q_6$, and $q_7$ is methyl. In certain embodiments, a THP nucleoside is provided in which one of $R_1$ and $R_2$ is F. In certain embodiments, $R_1$ is fluoro and $R_2$ is H; $R_1$ is methoxy and $R_2$ is H; and $R_1$ is methoxyethoxy and $R_2$ is H.

Examples of such sugar substitutes include, but are not limited to, those known in the art as hexitol nucleic acid (HNA), altitol nucleic acid (ANA) and mannitol nucleic acid (MNA) (see Leumann, C. J., Bioorg. & Med. Chem., 2002, 10, 841-854).

In certain embodiments, a sugar surrogate includes a ring having more than 5 atoms and more than one heteroatom. For example, a nucleoside containing a morpholino sugar moiety and use thereof in an oligomeric compound have been reported (see, for example, Braasch et al., Biochemistry, 2002, 41, 4503-4510; and U.S. Pat. Nos. 5,698,685; 5,166,315; 5,185,444; and 5,034,506).

As used herein, the term "morpholino" means a sugar surrogate having the following structure:

[Chemical Formula 19]

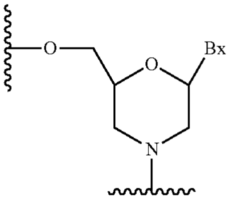

In certain embodiments, a morpholino can be modified, for example, by adding or changing various substituents from the above morpholino structure. Such a sugar surrogate is referred to herein as a "modified morpholino."

In certain embodiments, an oligonucleotide includes one or more modified cyclohexenyl nucleosides, which are nucleosides having a 6-membered cyclohexenyl in place of a pentofuranosyl residue of a naturally occurring nucleoside. Examples of modified cyclohexenyl nucleosides include, but are not limited to, those described in the art (see, for example, according to sharing, WO 2010/036696 published on Apr. 10, 2010, Robeyns et al., J. Am. Chem. Soc., 2008, 130 (6), 1979-1984; Horvath et al., Tetrahedron Letters, 2007, 48, 3621-3623; Nauwelaerts et al., J. Am. Chem. Soc., 2007, 129 (30), 9340-9348; Gu et al., Nucleosides, Nucleotides & Nucleic Acids, 2005, 24 (5-7), 993-998; Nauwelaerts et al., Nucleic Acids Research, 2005, 33 (8), 2452-2463; Robeyns et al., Acta Crystallographica, Section F: Structural Biology and Crystallization Communications, 2005, F61 (6), 585-586; Gu et al., Tetrahedron, 2004, 60 (9), 2111-2123; Gu et al., Oligonucleotides, 2003, 13 (6), 479-489; Wang et al., J. Org. Chem., 2003, 68, 4499-4505; Verbeure et al., Nucleic Acids Research, 2001, 29 (24), 4941-4947; Wang et al., J. Org. Chem., 2001, 66, 8478-82; Wang et al., Nucleosides, Nucleotides & Nucleic Acids, 2001, 20 (4-7), 785-788; Wang et al., J. Am. Chem., 2000, 122, 8595-8602; WO 06/047842; and WO 01/049687; text of each of these is incorporated herein by reference in its entirety).

Certain modified cyclohexenyl nucleosides have the following formula:

[Chemical Formula 20]

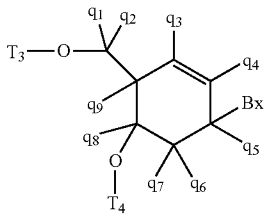

wherein

Bx is a heterocyclic base moiety;

$T_3$ and $T_4$ are each independently an internucleoside linking group linking a cyclohexenyl nucleoside analog to an oligonucleotide compound; or one of $T_3$ and $T_4$ is an internucleoside linking group linking a tetrahydropyran nucleoside analog to an oligonucleotide compound, and the other of $T_3$ and $T_4$ is H, a hydroxyl protecting group, a linking conjugate group or a 5'- or 3'-terminal group; and $q_1$, $q_2$, $q_3$, $q_4$, $q_5$, $q_6$, $q_7$, $q_8$ and $q_9$ are each independently H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent.

Many other bicyclic and tricyclic sugar substitute ring systems are known in the art that can be used to modify a nucleoside for incorporation into an oligonucleotide (see, for example, a review: Leumann, Christian J., Bioorg. & Med. Chem., 2002, 10, 841-854). Such ring systems can undergo various additional substitutions for activity enhancement.

A method for preparing a modified sugar is well known to a person skilled in the art. Some representative U.S. patents that teach preparation of such modified sugars include, but are not limited to: U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032, as well as WO 2005/121371, and each of these is incorporated herein by reference in its entirety.

In a nucleotide having a modified sugar moiety, a nucleobase moiety (natural, modified or a combination thereof) is maintained during hybridization with an appropriate nucleic acid target.

Preferred modified sugars are sugar moieties of ALNA [Ms], ALNA[mU], ALNA[ipU], ALNA[Oxz], or ALNA [Trz], and among these, the sugar moiety of ALNA[Ms] is more preferable. These modified sugars are novel, and a modified oligonucleotide for ATXN3 containing these modified sugars may hybridize to any region of ATXN3.

That is, in certain embodiments, the modified oligonucleotide of the present embodiment is a modified oligonucleotide having an activity of inhibiting ATXN3 expression and consisting of 12-24 residues, preferably 16, 17 or 18 residues, wherein a nucleobase sequence of the modified oligonucleotide has a complementarity of at least 85%, at least 90%, or at least 95% to an equal length portion of the nucleobase sequence of SEQ ID NO: 1 in the sequence listing, and at least one of nucleosides forming the oligonucleotide has a modified sugar selected from sugar moieties of ALNA[Ms], ALNA[mU], ALNA[ipU], ALNA[Oxz], or ALNA[Trz].

(Modified Nucleobases)

Modification or substitution of a nucleobase (or base) is structurally distinguishable from a naturally occurring or synthetic unmodified nucleobase and is further functionally interchangeable with such an unmodified nucleobase. Both natural and modified nucleobases are capable of participating in hydrogen bonding. Such a nucleobase modification can impart nuclease stability, binding affinity or some other beneficial biological properties to an oligonucleotide compound. As the modified oligonucleotide of the present invention, a modified oligonucleotide in which at least one nucleoside forming the modified oligonucleotide contains a modified nucleobase is preferably used. An example of the modified nucleobase is a 5-methylcytosine (5-me-C). The 5-methylcytosine means a cytosine modified with a methyl group attached to a 5-position. Certain nucleobase substitutions, including a 5-methylcytosine substitution, are particularly useful for increasing the binding affinity of an oligonucleotide. For example, 5-methylcytosine substitution has been shown to increase nucleic acid duplex stability by 0.6-1.2° C. (Sanghvi, Y. S., Crooke, S. T., and Lebleu, B., eds., Antisense Research and Applications, CRC Press, Boca Raton, 1993, pp. 276-278).

Additional modified nucleobases include 5-hydroxymethylcytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azouracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, especially 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and 3-deazaguanine and 3-deazaadenine.

Heterocyclic base moieties can also include those in which a purine or pyrimidine base is replaced with other heterocycles, for example 7-deaza-adenine, 7-deazaguanosine, 2-aminopyridine and 2-pyridone. Examples of nucleobases that are particularly useful for increasing the binding affinity of a modified oligonucleotide include 5-substituted pyrimidines, 6-azapyrimidines and N-2, N-6 and 0-6 substituted purines (including 2 aminopropyladenine, 5-propynyluracil and 5-propynylcytosine).

(Modified Internucleoside Linkage)

A naturally occurring internucleoside linkage of RNA and DNA is a 3'-5' phosphodiester linkage. An oligonucleotide having one or more modified, that is, non-naturally occurring, internucleoside linkages is often preferred over an oligonucleotide having a naturally occurring internucleoside linkage because of properties such as, for example, enhanced cellular uptake, enhanced affinity for a target nucleic acid, and increased stability in the presence of nucleases.

An oligonucleotide having modified internucleoside linkages include internucleoside linkages that retain a phosphorus atom and internucleoside linkages that do not have a phosphorus atom. Representative phosphorus containing internucleoside linkages include, but are not limited to, one of more of phosphodiesters, phosphotriesters, methylphosphonates, phosphoramidate, and phosphorothioates. Methods for preparing phosphorous-containing and non-phosphorous-containing linkages are well known.

An internucleoside linkage of the modified oligonucleotide of the present invention may be any internucleoside linkage as long as the modified oligonucleotide has an activity of inhibiting ATXN3 expression. However, those in which at least one internucleoside linkage contains a phosphorothioate internucleoside linkage are preferably used. For example, all internucleoside linkages may be phosphorothioate internucleoside linkages.

(Modified Oligonucleotide Motif)

In certain embodiments, the modified oligonucleotide of the present invention can have a gapmer motif in order to obtain an increased resistance to degradation by nuclease, an increased cellular uptake, an increased binding affinity for a target nucleic acid, and/or an increased ATXN3 expression inhibitory activity.

A “gapmer” means a modified oligonucleotide in which an internal region having multiple nucleosides that support RNase H cleavage is positioned between external regions having one or more nucleosides. An internal region can be referred to as a “gap segment” and an external region can be referred to as a “wing segment.” A wing segment existing on a 5' side of a gap segment can be referred to as a “5' wing segment,” and a wing segment existing in a 3' side of a gap segment can be referred to as a “3' wing segment.” In a gapmer, sugar moieties of nucleosides of wings that are close to a gap (a nucleoside of a 5' wing on a most 3'-side and a nucleoside of a 3' wing on a most 5'-side) are different from sugar moieties of adjacent gap nucleosides. For example, the sugar moieties of the nucleoside of the 5' wing on the most 3'-side and the nucleoside of the 3' wing on the most 5'-side are modified sugars, and the sugar moieties of the adjacent gap nucleosides are natural DNA sugar moieties.

A wing-gap-wing motif can be described as “X-Y-Z,” where “X” represents a sequence length of a 5' wing region, “Y” represents a sequence length of a gap region, and “Z” represents a sequence length of a 3' wing region.

In certain embodiments, the modified oligonucleotide of the present invention includes: (1) a gap segment; (2) a 5' wing segment; and (3) a 3' wing segment wherein the gap segment is positioned between the 5' wing segment and the 3' wing segment, and nucleosides of the 5' wing segment and the 3' wing segment each contain a modified sugar. Sugar moieties of nucleosides of a gap segment may be natural DNA sugar moieties only, or may include one or more modified sugars. The modified sugars are preferably selected from a group consisting of bicyclic sugars, 2'-MOE-modified sugars, and 2'-OMe-modified sugars. Examples of the bicyclic sugars include, for example, at least one sugar moiety of LNA, GuNA, ALNA[Ms], ALNA[mU], ALNA [ipU], ALNA[Oxz] and ALNA[Trz].

The number of nucleosides contained in each of a gap segment, a 5' wing segment, and a 3' wing segment may be any number as long as it has an ATXN3 expression inhibitory activity. However, for example, it is 12 for the gap segment, 3 for the 5' wing segment, and 3 for the 3' wing segment, or it is 10 for the gap segment, 3 for the 5' wing segment, and 3 for the 3' wing segment. More preferably, it is 12 for the gap segment, 3 for the 5' wing segment, and 3 for the 3' wing segment.

In certain embodiments, a cap structure is included at one end or each of both ends of a modified oligonucleotide to enhance properties such as nuclease stability. Preferred cap structures include 4',5'-methylene nucleotide, 1-(β-D-erythrofuranosyl) nucleotide, 4'-thionucleotide, carbocyclic nucleotide, 1,5-anhydrohexitol nucleotide, L-nucleotide, α-nucleotide, modified base nucleotide, phosphorodithioate bond, threo-pentoflanosyl nucleotide, acyclic 3',4'-seco-nucleotide, acyclic 3,4-dihydroxybutyl nucleotide, acyclic 3,5-dihydroxypentyl nucleotide, 3'-3'-inverted nucleotide moiety, 3'-3'-inverted debasement part, 3'-2'-inverted nucleotide moiety, 3'-2'-inverted debasement moiety, 1,4-butanediol phosphate, 3'-phosphoruamidate, hexyl phosphate, aminohexyl phosphate, 3'-phosphate, 3'-phospholothioate, phosphorodithioate, crosslinked methylphosphonate and non-crosslinked methylphosphonate moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 5'-5'-inverted nucleotide moiety, 5'-5'-inverted debasement moiety, 5'-phosphorumidate, 5'-phosphorothioate, 5'-amino, cross-linked and/or non-cross-linked 5'-phospholumidate, phosphorothioate, and 5'-mercapto moiety.

(Method for Evaluating the Compound of the Present Invention)

A method for evaluating the compound of the present invention may be any method as long as the method can very that the compound of the present invention inhibits an intracellular expression level of ATXN3. However, specifically, for example, the in vitro and in vivo ATXN3 expression measurement methods to be described below are used.

An in vitro ATXN3 expression measurement method for evaluating inhibition of intracellular ATXN3 expression by the compound of the present invention can use any cells in which ATXN3 is expressed (hereinafter, such cells may be referred to as “ATXN3-expressing cells”). However, for example, SH-SY5Y cells (human neuroblastoma cells, for example, ATCC CRL-2266) can be used.

A method for causing the compound of the present invention to be in contact with ATXN3-expressing cells is also not particularly limited. However, an example thereof is a method that is generally used for introducing a nucleic acid into cells. Specific examples thereof include a lipofection method, an electroporation method, a Gymnosis method, and the like. In the Gymnosis method, the compounds of the present invention can be treated, for example, at a final concentration of 0.3, 1, 3, 10 or 30 μM.

An intracellular mRNA level of ATXN3 can be assayed using various methods known in the art. Specific examples include Northern blot analysis, competitive polymerase chain reaction (PCR) or quantitative real-time PCR, and the like.

An intracellular protein level of ATXN3 can be assayed using various methods known in the art. Specific examples thereof include immunoprecipitation, Western blot analysis (immunoblotting), enzyme-linked immunosorbent assay (ELISA), quantitative protein assay, protein activity assay (for example, caspase activity assay), immunohistochemistry, immunocytochemistry or fluorescence activated cell sorting (FACS), and the like.

An example of an in vivo ATXN3 expression measurement method for evaluating inhibition of intracellular ATXN3 expression by the compound of the present invention is a method in which the compound of the present invention is administered to an animal expressing ATXN3 and the above-described ATXN3 expression level analysis is performed with respect to the cells.

The compound of the present invention can be synthesized using a phosphoramidite method using commercially available amidites (including also LNA) for DNA and RNA synthesis. Artificial nucleic acids ALNA[Ms], ALNA[mU], ALNA[ipU], ALNA[Oxz] and ALNA[Trz] can synthesize an oligomer using a method described in International Application PCT/JP 2019/044182 (WO 2020/100826) (see a reference example to be described below).

(Treatment of ATXN3-Related Diseases with the Compound of the Present Invention)

The compound of the present invention can treat ATXN3-related diseases by inhibiting ATXN3-expression. An ATXN3-related disease is not particularly limited as long as it is a disease caused by an ATXN3 abnormality. However, an example thereof is a neurodegenerative disease.

Further, the compound of the present invention can ameliorate one or more symptoms of a neurodegenerative disease. Examples of the symptoms include ataxia, neuropathy and aggregate formation. An example of a neurodegenerative disease is spinocerebellar ataxia type 3.

In spinocerebellar ataxia type 3, occurrence of CAG repeat expansion in ATXN3 causes mitochondrial disorders, transcriptional abnormalities, calcium homeostasis abnormalities, autophagy abnormalities, axonal transport abnormalities and the like due to RNA toxicity or its translation product, polyglutamine, and motor dysfunction occurs following cerebellar Purkinje cell dysfunction and shedding. It is known that motor dysfunction is suppressed by administration of antisense oligonucleotide of ATXN3, which causes inhibition of ATXN3 mRNA expression, to spinocerebellar ataxia type 3 model animals that express CAG repeat expansion of ATXN3. Therefore, the modified oligonucleotide of the present invention that strongly inhibits ATXN3 expression can treat, prevent, or delay progression of spinocerebellar ataxia type 3.

Therefore, the present invention provides: a modified oligonucleotide for use in treating, preventing or delaying progression of ATXN3-related diseases; a pharmaceutical composition for use in treating, preventing or delaying progression of ATXN3-related diseases; use of a modified oligonucleotide for treating, preventing or delaying progression of ATXN3-related diseases; use of a modified oligonucleotide in producing a medicament for treating, preventing or delaying progression of ATXN3-related diseases; a modified oligonucleotide for use in producing a medicament for treating, preventing or delaying progression of ATXN3-related diseases; and a method for treating, preventing or delaying progression of ATXN3-related diseases, including administering an effective amount of a modified oligonucleotide to a subject in need thereof.

(2) Pharmacological Composition Containing a Modified Oligonucleotide

The compound of the present invention, or a pharmaceutically acceptable salt thereof, and the compound of the present invention containing a pharmaceutically acceptable carrier can be used as pharmaceutical compositions. For preparation of a pharmaceutical composition, the modified oligonucleotide can be mixed with one or more pharmaceutically acceptable active or inactive substances. A composition and a method for formulating a pharmaceutical composition can be selected according to several criteria including a route of administration, a severity of a disease, or a dose to be administered.

For example, as a composition for parenteral administration, for example, an injection is used. Such an injection is prepared according to a method commonly known per se, for example, by dissolving, suspending or emulsifying the modified oligonucleotide in a sterile aqueous or oily solution usually used for injections. As an aqueous solution for injection, for example, phosphate buffered saline, physiological saline, an isotonic solution containing glucose or other adjuvants, and the like are used, and may be used in combination with a suitable solubilizing agent, for example, alcohol (for example, ethanol), polyalcohol (for example, propylene glycol, polyethylene glycol), nonionic surfactant [for example, poly solvate 80, HCO-50 (polyoxyethylene (50 mol) adduct of hydrogenated castor oil)], and the like. Further, a buffering agent, a pH adjusting agent, an isotonizing agent, a soothing agent, a preservative, a stabilizer, and the like can be contained. Such compositions are produced using commonly known methods.

Examples of parenteral administration include, but are not limited to, subcutaneous administration, intravenous administration, intramuscular administration, intraarterial administration, intraperitoneal administration, intracranial administration, intrathecal administration, and intracerebroventricular administration. Administration may be continuous or long-term, or may be short-term or intermittent.

Examples of compositions for oral administration include solid or liquid dosage forms, specifically, tablets (including sugar-coated tablets and film-coated tablets), pills, granules, powders, capsules (including soft capsules), syrups, emulsions, suspensions, and the like. Such compositions are produced using methods commonly known and contain carriers, diluents or excipients commonly used in the pharmaceutical field. As carriers and excipients for tablets, for example, lactose, starch, sucrose, magnesium stearate, and the like are used, and as a diluent, for example, physiological saline is used.

Further, the pharmacological composition of the present invention can include a nucleic acid introduction reagent. As the nucleic acid introduction reagent, liposome, lipofectin, lipofectamine, DOGS (transfectum), DOPE, DOTAP, DDAB, DHDEAB, HDEAB, polybrene, or cationic lipids such as poly (ethyleneimine) (PEI), or the like can be used.

Further, the modified oligonucleotide contained in the pharmaceutical composition of the present invention is preferably conjugated with conjugate groups of protein, biotin, phenazine, vitamin, peptide, folate, phenanthridine, anthraquinone, acridine, fluorescein, rhodamine, coumarin and pigments, which have affinity for in vivo molecules such as fatty acids, cholesterol, carbohydrates, phospholipids, and antibodies, at one or more sites. The conjugated modified oligonucleotide can be produced using a commonly known method, and can be selected to enhance its activity, tissue distribution, cell distribution or cell uptake.

The conjugate group is directly attached to the modified oligonucleotide, or the conjugate group is attached to the modified oligonucleotide by a linking moiety selected from amino, hydroxy, carboxylic acid, thiol, unsaturated moiety (for example, a double or triple bond), 8-amino-3,6-dioxaoctanoic acid (ADO), succinimidyl 4-(N-maleimidemethyl) cyclohexane-1-carboxylate (SMCC), 6-aminocaproic acid (AHEX or AHA), azide, substituted $C_1$-$C_{10}$ alkyl, substituted or unsubstituted $C_2$-$C_{10}$ alkenyl, and substituted or unsubstituted $C_2$-$C_{10}$ alkynyl. Here, a substituent is selected from amino, alkoxy, carboxy, zazide, benzyl, phenyl, nitro, thiol, thioalkoxy, halogen, alkyl, aryl, alkenyl and alkynyl.

An administration form of the pharmaceutical composition of the present invention may be systemic administration such as oral administration, intravenous administration, or intraarterial administration, or may be local administration such as intracranial administration, intrathecal administration, or intracerebroventricular administration, but is not limited to these. Dosage of the pharmaceutical composition of the present invention can be changed as appropriate depending on a purpose of use, severity of the disease, age, body weight, gender, and the like of a patient. However, an amount of the modified oligonucleotide can usually be selected from a range of 0.1 ng-100 mg/kg/day, preferably 1 ng-10 mg/kg/day.

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references described in this application is incorporated herein by reference in its entirety.

Example 1

Synthesis and Purification of Modified Oligonucleotide Compound for In Vitro Evaluation Using ALNA[Ms] amidites (synthesized using a method described in International Application PCT/JP 2019/044182 (WO 2020/100826)), a modified oligonucleotide compound was synthesized using a DNA/RNA oligonucleotide automatic synthesizer nS-8II (manufactured by GeneDesign, Inc.) on a 0.5 μmol scale using a CPG or a polystyrene carrier. All the amidites were prepared in a 0.1 M acetonitrile solution; a coupling time in unnatural nucleosides was 10 minutes; and other steps were performed under standard conditions of nS-8II. Activator 42 (Sigma-Aldrich) was used as an activator, Sulfurizing Reagent II (Gren Research Corporation) was used for thiolation, and Oxidizer (Sigma-Aldrich) was used for oxidation. A synthesized oligonucleotide was excised from the carrier and a base moiety was deprotected by adding a 28% aqueous ammonia solution and causing the mixture to react at 85° C. for 8 hours. After ammonia was concentrated and distilled off, simple purification with NAP10 was performed, and then reverse phase HPLC purification was performed.

The synthesized modified oligonucleotide compounds are shown in Table 1 (18-residue modified oligonucleotides) and Table 2 (16-residue modified oligonucleotides). In the notation of the compounds, each nucleotide is represented by three letters. However, a 3'-end nucleotide is represented by two letters since there is no internucleoside linkage.

1) The first letter is capitalized and indicates the following nucleobases:

A=adenine, T=thymine, G=guanine, C=cytosine, U=uracil, M=5-methylcytosine;

2) The second letter indicates the following sugar moieties:

m=ALNA[Ms], and d=2'-deoxyribose; and

3) The third letter indicates the following internucleoside linkage:

s=phosphorothioate, p=phosphodiester.

A target starting position indicates an ATXN3 pre-mRNA 5' target site of a modified oligonucleotide (a position of SEQ ID NO: 1 in the sequence listing corresponding to a 3' end of the modified oligonucleotide), and a target ending position indicates an ATXN3 pre-mRNA 3' target site of a modified oligonucleotide (a position of SEQ ID NO: 1 in the sequence listing corresponding to a 5' end of the modified oligonucleotide).

Example 2

Purification and Purity Confirmation of Modified Oligonucleotide Compound

Purification and purity confirmation of a synthesized modified oligonucleotide compound were performed by reverse phase HPLC under the following conditions.

Reversed Phase HPLC (Purification)

Mobile Phase:

Solution A: 400 mM hexafluoroisopropanol, 15 mM triethylamine

Solution B: methanol

Gradient: A:B=83:17→70:30 (10 min)

Columns Used:

Preparative isolation Waters XBridge @ Oligonucleotide BEH C18 OBDTM Prep Column, 130 Å, 2.5 μm, 10 mm*50 mm Flow Rate:

Preparative isolation 5 mL/min

Column temperature: 60° C.

Detection: UV (260 nm)

Reversed Phase HPLC (Purity Confirmation)

Mobile Phase:

Solution A: 400 mM hexafluoroisopropanol, 15 mM triethylamine aqueous solution

Solution B: methanol

Gradient: A:B=82:18→73.5:26.5 (5 min)

Columns Used:

Waters XBridge@ Oligonucleotide BEH C18 OBDTM Prep Column, 130 Å, 2.5 μm, 4.6 mm*50 mm Flow rate: 1 mL/min Column temperature: 60° C.

Detection: UV (260 nm)

Example 3

In Vitro ATXN3 Expression Ratio Test (Gymnosis Method)

At the same time as seeding $3\times10^3$ SH-SY5Y cells per well, a synthesized modified oligonucleotide was added at a final concentration of 3 or 10 μmol/L and incubated in a $CO_2$ incubator for 3 days. After RNA was extracted from the cells, a reverse transcription reaction was performed to obtain cDNA. Using the obtained cDNA, quantitative real-time PCR with primers and probes for ATXN3 or GAPDH was performed. An ATXN3 mRNA level was obtained by calculating an amount ratio with respect to GAPDH. An ATXN3 expression ratio was calculated as a percentage by comparing an ATXN3 mRNA level in cells to which the modified oligonucleotide was added to an ATXN3 mRNA level in cells to which the modified oligonucleotide was not added. Tables 1 and 3 show the results of the ATXN3 expression ratios when 18-residue modified oligonucleotides were added at a final concentration of 3 μmol/L, and Table 2 shows the results of the ATXN3 expression ratios when 16-residue modified oligonucleotides were added at a final concentration of 10 μmol/L.

Example 4

In Vitro ATXN3 Expression Ratio Test (Gymnosis Method)

650528, which is a representative modified oligonucleotide described in WO 2018/089805, 1100673, which is a representative modified oligonucleotide described in WO 2019/217708, or 1287095, which is a representative modified oligonucleotide described in WO 2020/172559, was synthesized. Target starting positions and target ending positions of these modified oligonucleotides are as shown in Table 4. Synthesis was performed using 2'-MOE (2'-O-methoxyethyl) amidite in the same way as in Examples 1 and 2. At the same time as seeding $3\times10^3$ SH-SY5Y cells per well, a synthesized modified oligonucleotide was added at a final concentration of 3 or 10 μmol/L and incubated in a $CO_2$ incubator for 3 days. After RNA was extracted from the cells, a reverse transcription reaction was performed to obtain cDNA. Using the obtained cDNA, quantitative real-time PCR with primers and probes for ATXN3 or GAPDH was performed. An ATXN3 mRNA level was obtained by calculating an amount ratio with respect to GAPDH. An ATXN3 expression ratio was calculated as a percentage by comparing an ATXN3 mRNA level in cells to which the modified oligonucleotide was added to an ATXN3 mRNA level in cells to which the modified oligonucleotide was not added. The results are shown in Table 4.

TABLE 1

| Compound ID | SEQ ID | Target starting position | Target ending position | Sequence | ATXN3 expression ratio (3 μM) |
|---|---|---|---|---|---|
| 1 | 3 | 256 | 273 | GmsMmsGmsTdsAdsGdsGdsTdsGdsAdsTdsGdsMdsTdsMdsMmsMmsMm | 80.0 |
| 2 | 4 | 404 | 421 | AmsGmsGmsAdsAdsTdsMdsMdsTdsMdsMdsGdsAdsAdsAdsAmsGmsMm | 75.6 |
| 3 | 5 | 405 | 422 | AmsAmsGmsGdsAdsAdsTdsMdsMdsTdsMdsMdsGdsAdsAdsAmsAmsGm | 86.9 |
| 4 | 6 | 407 | 424 | TmsGmsAmsAdsGdsGdsAdsAdsTdsMdsMdsTdsMdsMdsGdsAmsAmsAm | 90.2 |
| 5 | 7 | 408 | 425 | GmsTmsGmsAdsAdsGdsGdsAdsAdsTdsMdsMdsTdsMdsMdsGmsAmsAm | 74.5 |
| 6 | 8 | 409 | 426 | GmsGmsTmsGdsAdsAdsGdsGdsAdsAdsTdsMdsMdsTdsMdsMmsGmsAm | 84.8 |
| 7 | 9 | 410 | 427 | GmsGmsGmsTdsGdsAdsAdsGdsGdsAdsAdsTdsMdsMdsTdsMmsMmsGm | 82.2 |
| 8 | 10 | 541 | 558 | GmsAmsMmsTdsMdsMdsAdsAdsTdsAdsTdsAdsGdsAdsAdsTmsTmsGm | 76.1 |
| 9 | 11 | 647 | 664 | GmsTmsMmsAdsGdsGdsMdsMdsMdsTdsAdsMdsAdsGdsTdsGmsGmsGm | 73.1 |
| 10 | 12 | 648 | 665 | TmsGmsTmsMdsAdsGdsGdsMdsMdsMdsTdsAdsMdsAdsGdsTmsGmsGm | 79.6 |
| 11 | 13 | 697 | 714 | MmsGmsAmsMdsTdsTdsMdsMdsMdsTdsGdsTdsTdsTdsAdsGmsGmsGm | 79.2 |
| 12 | 14 | 698 | 715 | AmsMmsGmsAdsMdsTdsTdsMdsMdsMdsTdsGdsTdsTdsTdsAmsGmsGm | 68.8 |
| 13 | 15 | 699 | 716 | GmsAmsMmsGdsAdsMdsTdsTdsMdsMdsMdsTdsGdsTdsTdsTmsAmsGm | 64.4 |
| 14 | 16 | 767 | 784 | GmsMmsMmsTdsGdsMdsTdsMdsMdsGdsGdsAdsAdsAdsGdsAmsTmsGm | 78.3 |
| 15 | 17 | 2043 | 2060 | AmsGmsTmsAdsGdsTdsGdsTdsGdsGdsAdsAdsMdsAdsTdsGmsTmsTm | 65.7 |
| 16 | 18 | 2045 | 2062 | GmsAmsAmsGdsTdsAdsGdsTdsGdsTdsGdsGdsAdsAdsMdsAmsTmsGm | 75.4 |
| 17 | 19 | 2046 | 2063 | GmsGmsAmsAdsGdsTdsAdsGdsTdsGdsTdsGdsGdsAdsAdsMmsAmsTm | 67.5 |
| 18 | 20 | 2047 | 2064 | AmsGmsGmsAdsAdsGdsTdsAdsGdsTdsGdsTdsGdsGdsAdsAmsMmsAm | 69.0 |
| 19 | 21 | 2048 | 2065 | MmsAmsGmsGdsAdsAdsGdsTdsAdsGdsTdsGdsTdsGdsGdsAmsAmsMm | 71.2 |
| 20 | 22 | 2092 | 2109 | GmsTmsMmsMdsMdsAdsAdsMdsTdsAdsGdsGdsTdsAdsAdsMmsAmsAm | 68.8 |
| 21 | 23 | 2159 | 2176 | TmsMmsGmsGdsGdsTdsAdsAdsGdsTdsAdsGdsAdsTdsTdsTmsTmsMm | 51.2 |
| 22 | 24 | 2502 | 2519 | AmsGmsGmsMdsMdsTdsAdsTdsAdsMdsAdsMdsAdsTdsGdsMmsTmsGm | 79.9 |
| 23 | 25 | 2513 | 2530 | GmsAmsAmsGdsTdsAdsTdsMdsTdsGdsTdsAdsGdsGdsMdsMmsTmsAm | 57.9 |
| 24 | 26 | 2646 | 2663 | GmsGmsAmsMdsTdsGdsTdsAdsTdsAdsGdsGdsAdsGdsAdsTmsTmsAm | 55.0 |
| 25 | 27 | 2650 | 2667 | GmsAmsAmsTdsGdsGdsAdsMdsTdsGdsTdsAdsTdsAdsGdsGmsAmsGm | 63.2 |

TABLE 1-continued

| Compound ID | SEQ ID | Target starting position | Target ending position | Sequence | ATXN3 expression ratio (3 μM) |
|---|---|---|---|---|---|
| 26 | 28 | 4011 | 4028 | MmsMmsTmsMdsTdsTdsAdsGdsTdsGdsMdsTdsMdsTdsMdsMmsGmsAm | 75.2 |
| 27 | 29 | 4012 | 4029 | TmsMmsMmsTdsMdsTdsTdsAdsGdsTdsGdsMdsTdsMdsTdsMmsMmsGm | 73.3 |
| 28 | 30 | 4041 | 4058 | AmsAmsGmsMdsTdsGdsTdsMdsAdsAdsTdsMdsTdsAdsGdsMmsAmsGm | 65.2 |
| 29 | 31 | 4046 | 4063 | GmsGmsGmsAdsMdsAdsAdsGdsMdsTdsGdsTdsMdsAdsAdsTmsMmsTm | 80.1 |
| 30 | 32 | 4267 | 4284 | TmsAmsGmsGdsMdsMdsMdsAdsGdsAdsMdsTdsTdsMdsAdsTmsTmsGm | 77.6 |
| 31 | 33 | 4268 | 4285 | TmsTmsAmsGdsGdsMdsMdsMdsAdsGdsAdsMdsTdsTdsMdsAmsTmsTm | 76.0 |
| 32 | 34 | 4269 | 4286 | TmsTmsTmsAdsGdsGdsMdsMdsMdsAdsGdsAdsMdsTdsTdsMmsAmsTm | 72.0 |
| 33 | 35 | 5179 | 5196 | MmsAmsAmsTdsGdsAdsMdsAdsAdsTdsGdsAdsGdsMdsMdsMmsAmsMm | 78.7 |
| 34 | 36 | 5843 | 5860 | GmsTmsTmsAdsTdsAdsGdsGdsAdsTdsGdsMdsAdsGdsGdsTmsAmsAm | 63.9 |
| 35 | 37 | 5844 | 5861 | GmsGmsTmsTdsAdsTdsAdsGdsGdsAdsTdsGdsMdsAdsGdsGmsTmsAm | 54.2 |
| 36 | 38 | 5845 | 5862 | AmsGmsGmsTdsTdsAdsTdsAdsGdsGdsAdsTdsGdsMdsAdsGmsGmsTm | 45.8 |
| 37 | 39 | 5853 | 5870 | AmsTmsAmsAdsTdsGdsGdsGdsAdsGdsGdsTdsTdsAdsTdsAmsGmsGm | 70.3 |
| 38 | 40 | 7203 | 7220 | GmsAmsAmsTdsAdsAdsGdsTdsAdsGdsMdsTdsTdsGdsGdsAmsGmsMm | 75.9 |
| 39 | 41 | 7208 | 7225 | GmsTmsAmsAdsGdsGdsAdsAdsTdsAdsAdsGdsTdsAdsGdsMmsTmsTm | 75.2 |
| 40 | 42 | 7535 | 7552 | GmsAmsMmsAdsMdsMdsAdsGdsGdsTdsTdsTdsGdsMdsMdsMmsMmsTm | 70.9 |
| 41 | 43 | 7536 | 7553 | AmsGmsAmsMdsAdsMdsMdsAdsGdsGdsTdsTdsTdsGdsMdsMmsMmsMm | 73.3 |
| 42 | 44 | 7741 | 7758 | AmsTmsGmsGdsGdsAdsGdsGdsTdsAdsGdsGdsTdsAdsMdsAmsAmsMm | 77.6 |
| 43 | 45 | 7788 | 7805 | GmsGmsAmsMdsTdsGdsMdsAdsMdsMdsMdsAdsAdsGdsMdsTmsMmsAm | 72.2 |
| 44 | 46 | 7792 | 7809 | AmsGmsAmsGdsGdsGdsAdsMdsTdsGdsMdsAdsMdsMdsMdsAmsAmsGm | 68.4 |
| 45 | 47 | 7793 | 7810 | AmsAmsGmsAdsGdsGdsGdsAdsMdsTdsGdsMdsAdsMdsMdsMmsAmsAm | 70.3 |
| 46 | 48 | 10997 | 11014 | MmsMmsMmsMdsAdsMdsTdsMdsTdsAdsAdsTdsAdsTdsGdsAmsAmsGm | 70.4 |
| 47 | 49 | 11642 | 11659 | GmsTmsMmsGdsMdsTdsMdsAdsGdsGdsAdsGdsAdsGdsGdsTmsTmsMm | 62.2 |
| 48 | 50 | 11643 | 11660 | GmsGmsTmsMdsGdsMdsTdsMdsAdsGdsGdsAdsGdsAdsGdsGmsTmsTm | 68.3 |
| 49 | 51 | 11644 | 11661 | AmsGmsGmsTdsMdsGdsMdsTdsMdsAdsGdsGdsAdsGdsAdsGmsGmsTm | 63.0 |
| 50 | 52 | 11645 | 11662 | TmsAmsGmsGdsTdsMdsGdsMdsTdsMdsAdsGdsGdsAdsGdsAmsGmsGm | 66.3 |
| 51 | 53 | 11646 | 11663 | AmsTmsAmsGdsGdsTdsMdsGdsMdsTdsMdsAdsGdsGdsAdsGmsAmsGm | 74.9 |
| 52 | 54 | 11651 | 11668 | MmsAmsGmsAdsGdsAdsTdsAdsGdsGdsTdsMdsGdsMdsTdsMmsAmsGm | 72.9 |
| 53 | 55 | 11655 | 11672 | TmsMmsTmsGdsMdsAdsGdsAdsGdsAdsTdsAdsGdsGdsTdsMmsGmsMm | 62.2 |
| 54 | 56 | 11734 | 11751 | MmsGmsGmsTdsAdsAdsAdsGdsMdsAdsMdsTdsAdsGdsAdsTmsGmsGm | 62.9 |
| 55 | 57 | 11735 | 11752 | AmsMmsGmsGdsTdsAdsAdsAdsGdsMdsAdsMdsTdsAdsGdsAmsTmsGm | 58.8 |
| 56 | 58 | 11741 | 11758 | AmsGmsTmsGdsGdsMdsAdsMdsGdsGdsTdsAdsAdsAdsGdsMmsAmsMm | 73.4 |
| 57 | 59 | 11799 | 11816 | AmsGmsTmsGdsMdsTdsGdsGdsGdsMdsMdsTdsAdsMdsTdsMmsTmsGm | 81.2 |
| 58 | 60 | 11800 | 11817 | AmsAmsGmsTdsGdsMdsTdsGdsGdsGdsMdsMdsTdsAdsMdsTmsMmsTm | 86.4 |
| 59 | 61 | 12710 | 12727 | GmsMmsTmsAdsTdsGdsTdsTdsAdsGdsTdsTdsGdsTdsGdsTmsAmsMm | 59.0 |
| 60 | 62 | 13136 | 13153 | AmsAmsMmsGdsTdsMdsTdsMdsTdsGdsMdsGdsMdsAdsGdsMdsAdsGmsMmsTm | 67.0 |
| 61 | 63 | 15115 | 15132 | GmsAmsAmsGdsMdsTdsAdsAdsGdsTdsAdsGdsGdsTdsGdsAmsMmsTm | 48.7 |
| 62 | 64 | 15116 | 15133 | TmsGmsAmsAdsGdsMdsTdsAdsAdsGdsTdsAdsGdsGdsTdsGmsAmsMm | 58.9 |
| 63 | 65 | 15703 | 15720 | AmsGmsAmsGdsGdsTdsGdsAdsTdsTdsMdsMdsMdsAdsMdsTmsMmsGm | 78.7 |

TABLE 1-continued

| Compound ID | SEQ ID | Target starting position | Target ending position | Sequence | ATXN3 expression ratio (3 μM) |
|---|---|---|---|---|---|
| 64 | 66 | 15704 | 15721 | TmsAmsGmsAdsGdsGdsTdsGdsAdsTdsTdsMdsMdsMdsAdsMmsTmsMm | 66.8 |
| 65 | 67 | 15705 | 15722 | MmsTmsAmsGdsAdsGdsGdsTdsGdsAdsTdsTdsMdsMdsMdsAmsMmsTm | 75.9 |
| 66 | 68 | 15706 | 15723 | MmsMmsTmsAdsGdsAdsGdsGdsTdsGdsAdsTdsTdsMdsMdsMmsAmsMm | 68.4 |
| 67 | 69 | 18749 | 18766 | GmsGmsTmsAdsAdsTdsAdsGdsMdsTdsAdsAdsGdsMdsAdsAmsGmsAm | 86.4 |
| 68 | 70 | 19061 | 19078 | GmsMmsTmsAdsMdsTdsMdsTdsGdsGdsTdsAdsMdsAdsGdsGmsAmsAm | 71.4 |
| 69 | 71 | 19163 | 19180 | MmsMmsTmsAdsGdsTdsMdsAdsMdsTdsTdsTdsGdsAdsTdsAmsGmsAm | 64.3 |
| 70 | 72 | 19355 | 19372 | GmsMmsAmsMdsTdsAdsAdsAdsGdsGdsMdsTdsMdsAdsTdsMmsTmsGm | 90.2 |
| 71 | 73 | 19736 | 19753 | GmsAmsAmsMdsAdsTdsMdsTdsTdsGdsAdsGdsTdsAdsGdsGmsTmsGm | 95.8 |
| 72 | 74 | 19737 | 19754 | GmsGmsAmsAdsMdsAdsTdsMdsTdsTdsGdsAdsGdsTdsAdsGmsGmsTm | 63.1 |
| 73 | 75 | 19738 | 19755 | AmsGmsGmsAdsAdsMdsAdsTdsMdsTdsTdsGdsAdsGdsTdsAmsGmsGm | 76.5 |
| 74 | 76 | 19739 | 19756 | MmsAmsGmsGdsAdsAdsMdsAdsTdsMdsTdsTdsGdsAdsGdsTmsAmsGm | 83.0 |
| 75 | 77 | 20833 | 20850 | TmsGmsTmsTdsMdsAdsGdsGdsGdsTdsAdsGdsAdsTdsGdsTmsMmsAm | 79.8 |
| 76 | 78 | 20835 | 20852 | GmsGmsTmsGdsTdsTdsMdsAdsGdsGdsGdsTdsAdsGdsAdsTmsGmsTm | 58.5 |
| 77 | 79 | 20836 | 20853 | AmsGmsGmsTdsGdsTdsTdsMdsAdsGdsGdsGdsTdsAdsGdsAmsTmsGm | 60.6 |
| 78 | 80 | 21059 | 21076 | GmsGmsGmsTdsGdsGdsGdsAdsMdsAdsTdsAdsAdsMdsAdsGmsGmsMm | 91.8 |
| 79 | 81 | 21060 | 21077 | AmsGmsGmsGdsTdsGdsGdsGdsAdsMdsAdsTdsAdsAdsMdsAmsGmsGm | 97.5 |
| 80 | 82 | 21482 | 21499 | GmsGmsAmsTdsAdsMdsTdsMdsTdsGdsMdsMdsMdsTdsGdsTmsTmsMm | 54.4 |
| 81 | 83 | 21483 | 21500 | TmsGmsGmsAdsTdsAdsMdsTdsMdsTdsGdsMdsMdsMdsTdsGmsTmsTm | 65.1 |
| 82 | 84 | 22109 | 22126 | AmsAmsGmsMdsTdsAdsGdsAdsTdsGdsMdsTdsAdsMdsAdsMmsAmsMm | 82.0 |
| 83 | 85 | 22195 | 22212 | MmsAmsAmsAdsMdsGdsTdsGdsTdsGdsGdsTdsTdsTdsGdsMmsAmsTm | 70.1 |
| 84 | 86 | 22196 | 22213 | TmsMmsAmsAdsAdsMdsGdsTdsGdsTdsGdsGdsTdsTdsTdsGmsMmsAm | 95.4 |
| 85 | 87 | 22197 | 22214 | GmsTmsMmsAdsAdsAdsMdsGdsTdsGdsTdsGdsGdsTdsTdsTmsGmsMm | 82.2 |
| 86 | 88 | 22198 | 22215 | TmsGmsTmsMdsAdsAdsAdsMdsGdsTdsGdsTdsGdsGdsTdsTmsTmsGm | 85.4 |
| 87 | 89 | 22200 | 22217 | GmsGmsTmsGdsTdsMdsAdsAdsAdsMdsGdsTdsGdsTdsGdsGmsTmsTm | 55.3 |
| 88 | 90 | 22913 | 22930 | GmsTmsAmsMdsMdsTdsTdsMdsMdsTdsGdsTdsGdsAdsTdsGmsGmsTm | 70.1 |
| 89 | 91 | 23046 | 23063 | MmsAmsGmsGdsMdsTdsAdsMdsTdsMdsAdsMdsTdsTdsAdsMmsTmsGm | 76.0 |
| 90 | 92 | 23047 | 23064 | GmsMmsAmsGdsGdsMdsTdsAdsMdsTdsMdsAdsMdsTdsTdsAmsMmsTm | 90.4 |
| 91 | 93 | 23048 | 23065 | AmsGmsMmsAdsGdsGdsMdsTdsAdsMdsTdsMdsAdsMdsTdsTmsAmsMm | 70.9 |
| 92 | 94 | 23049 | 23066 | GmsAmsGmsMdsAdsGdsGdsMdsTdsAdsMdsTdsMdsAdsMdsTmsTmsAm | 86.9 |
| 93 | 95 | 23050 | 23067 | TmsGmsAmsGdsMdsAdsGdsGdsMdsTdsAdsMdsTdsMdsAdsMmsTmsTm | 84.8 |
| 94 | 96 | 23055 | 23072 | TmsTmsGmsAdsMdsTdsGdsAdsGdsMdsAdsGdsGdsMdsTdsAmsMmsTm | 70.5 |
| 95 | 97 | 23056 | 23073 | MmsTmsTmsGdsAdsMdsTdsGdsAdsGdsMdsAdsGdsGdsMdsTmsAmsMm | 65.6 |
| 96 | 98 | 23057 | 23074 | AmsMmsTmsTdsGdsAdsMdsTdsGdsAdsGdsMdsAdsGdsGdsMmsTmsAm | 74.4 |
| 97 | 99 | 24651 | 24668 | MmsAmsGmsGdsMdsMdsMdsTdsTdsMdsMdsAdsTdsAdsGdsTmsGmsTm | 72.4 |
| 98 | 100 | 24652 | 24669 | MmsMmsAmsGdsGdsMdsMdsMdsTdsTdsMdsMdsAdsTdsAdsGmsTmsGm | 80.1 |
| 99 | 101 | 24653 | 24670 | TmsMmsMmsAdsGdsGdsMdsMdsMdsTdsTdsMdsMdsAdsTdsAmsGmsTm | 77.4 |
| 100 | 102 | 27388 | 27405 | MmsGmsTmsGdsTdsGdsMdsTdsAdsGdsTdsAdsTdsTdsTdsGmsTmsTm | 56.2 |
| 101 | 103 | 27389 | 27406 | MmsMmsGmsTdsGdsTdsGdsMdsTdsAdsGdsTdsAdsTdsTdsTmsGmsTm | 60.0 |

TABLE 1-continued

| Compound ID | SEQ ID | Target starting position | Target ending position | Sequence | ATXN3 expression ratio (3 µM) |
|---|---|---|---|---|---|
| 102 | 104 | 27391 | 27408 | GmsGmsMmsMdsGdsTdsGdsTdsGdsMdsTdsAdsGdsTdsAdsTmsTmsTm | 83.6 |
| 103 | 105 | 27392 | 27409 | TmsGmsGmsMdsMdsGdsTdsGdsTdsGdsMdsTdsAdsGdsTdsAmsTmsTm | 67.8 |
| 104 | 106 | 27393 | 27410 | TmsTmsGmsGdsMdsMdsGdsTdsGdsTdsGdsMdsTdsAdsGdsTmsAmsTm | 61.9 |
| 105 | 107 | 27394 | 27411 | AmsTmsTmsGdsGdsMdsMdsGdsTdsGdsTdsGdsMdsTdsAdsGmsTmsAm | 66.8 |
| 106 | 108 | 27395 | 27412 | GmsAmsTmsTdsGdsGdsMdsMdsGdsTdsGdsTdsGdsMdsTdsAmsGmsTm | 83.2 |
| 107 | 109 | 30559 | 30576 | AmsAmsGmsGdsTdsTdsGdsMdsMdsTdsGdsAdsMdsMdsMdsTmsGmsTm | 69.8 |
| 108 | 110 | 30560 | 30577 | MmsAmsAmsGdsGdsTdsTdsGdsMdsMdsTdsGdsAdsMdsMdsMmsTmsGm | 64.5 |
| 109 | 111 | 30561 | 30578 | AmsMmsAmsAdsGdsGdsTdsTdsGdsMdsMdsTdsGdsAdsMdsMmsMmsTm | 75.1 |
| 110 | 112 | 30564 | 30581 | GmsGmsTmsAdsMdsAdsAdsGdsGdsTdsTdsGdsMdsMdsTdsGmsAmsMm | 64.3 |
| 111 | 113 | 30565 | 30582 | GmsGmsGmsTdsAdsMdsAdsAdsGdsGdsTdsTdsGdsMdsMdsTmsGmsAm | 73.8 |
| 112 | 114 | 31570 | 31587 | TmsAmsGmsTdsAdsGdsAdsGdsTdsTdsTdsTdsGdsMdsTdsTmsGmsGm | 54.3 |
| 113 | 115 | 31574 | 31591 | GmsAmsTmsGdsTdsAdsGdsTdsAdsGdsAdsGdsTdsTdsTdsTmsGmsMm | 57.3 |
| 114 | 116 | 31575 | 31592 | TmsGmsAmsTdsGdsTdsAdsGdsTdsAdsGdsAdsGdsTdsTdsTmsTmsGm | 49.3 |
| 115 | 117 | 31576 | 31593 | MmsTmsGmsAdsTdsGdsTdsAdsGdsTdsAdsGdsAdsGdsTdsTmsTmsTm | 44.1 |
| 116 | 118 | 31841 | 31858 | GmsTmsGmsGdsTdsGdsGdsMdsTdsMdsAdsAdsGdsTdsAdsTmsTmsAm | 58.2 |
| 117 | 119 | 32007 | 32024 | MmsAmsAmsGdsTdsTdsGdsGdsTdsTdsTdsGdsTdsGdsGdsTmsAmsMm | 65.1 |
| 118 | 120 | 32008 | 32025 | GmsMmsAmsAdsGdsTdsTdsGdsGdsTdsTdsTdsGdsTdsGdsGmsTmsAm | 56.4 |
| 119 | 121 | 32009 | 32026 | TmsGmsMmsAdsAdsGdsTdsTdsGdsGdsTdsTdsTdsGdsTdsGmsGmsTm | 56.1 |
| 120 | 122 | 32010 | 32027 | MmsTmsGmsMdsAdsAdsGdsTdsTdsGdsGdsTdsTdsTdsGdsTmsGmsGm | 72.1 |
| 121 | 123 | 32011 | 32028 | MmsMmsTmsGdsMdsAdsAdsGdsTdsTdsGdsGdsTdsTdsTdsGmsTmsGm | 62.0 |
| 122 | 124 | 32012 | 32029 | TmsMmsMmsTdsGdsMdsAdsAdsGdsTdsTdsGdsGdsTdsTdsTmsGmsTm | 76.6 |
| 123 | 125 | 32127 | 32144 | TmsMmsTmsAdsGdsGdsMdsAdsAdsTdsTdsGdsTdsGdsGdsTmsGmsGm | 60.5 |
| 124 | 126 | 33630 | 33647 | GmsMmsAmsTdsGdsGdsMdsTdsAdsAdsTdsGdsAdsTdsGdsMmsAmsMm | 83.5 |
| 125 | 127 | 35711 | 35728 | TmsGmsTmsGdsAdsAdsGdsGdsTdsAdsGdsMdsGdsAdsAdsMmsAmsTm | 65.3 |
| 126 | 128 | 35712 | 35729 | GmsTmsGmsTdsGdsAdsAdsGdsGdsTdsAdsGdsMdsGdsAdsAmsMmsAm | 68.9 |
| 127 | 129 | 36411 | 36428 | GmsTmsAmsAdsMdsTdsMdsTdsGdsMdsAdsMdsTdsTdsMdsMmsMmsAm | 64.9 |
| 128 | 130 | 36413 | 36430 | AmsAmsGmsTdsAdsAdsMdsTdsMdsTdsGdsMdsAdsMdsTdsTmsMmsMm | 74.7 |
| 129 | 131 | 36607 | 36624 | GmsTmsMmsAdsTdsMdsMdsMdsTdsAdsTdsGdsTdsMdsTdsTmsAmsTm | 47.4 |
| 130 | 132 | 38559 | 38576 | GmsMmsAmsAdsMdsAdsGdsTdsMdsTdsGdsGdsAdsTdsTdsMmsTmsMm | 52.8 |
| 131 | 133 | 38587 | 38604 | GmsAmsGmsGdsTdsGdsTdsMdsMdsTdsTdsGdsTdsTdsAdsMmsTmsGm | 65.6 |
| 132 | 134 | 38588 | 38605 | GmsGmsAmsGdsGdsTdsGdsTdsMdsMdsTdsTdsGdsTdsTdsAmsMmsTm | 58.0 |
| 133 | 135 | 38589 | 38606 | TmsGmsGmsAdsGdsGdsTdsGdsTdsMdsMdsTdsTdsGdsTdsTmsAmsMm | 61.6 |
| 134 | 136 | 38590 | 38607 | GmsTmsGmsGdsAdsGdsGdsTdsGdsTdsMdsMdsTdsTdsGdsTmsTmsAm | 63.6 |
| 135 | 137 | 38593 | 38610 | AmsTmsTmsGdsTdsGdsGdsAdsGdsGdsTdsGdsTdsMdsMdsTmsTmsGm | 62.1 |
| 136 | 138 | 38594 | 38611 | MmsAmsTmsTdsGdsTdsGdsGdsAdsGdsGdsTdsGdsTdsMdsMmsTmsTm | 64.2 |
| 137 | 139 | 38596 | 38613 | GmsAmsMmsAdsTdsTdsGdsTdsGdsGdsAdsGdsGdsTdsGdsTmsMmsMm | 82.5 |
| 138 | 140 | 38597 | 38614 | GmsGmsAmsMdsAdsTdsTdsGdsTdsGdsGdsAdsGdsGdsTdsGmsTmsMm | 86.2 |
| 139 | 141 | 38598 | 38615 | MmsGmsGmsAdsMdsAdsTdsTdsGdsTdsGdsGdsAdsGdsGdsTmsGmsTm | 85.8 |

TABLE 1-continued

| Compound ID | SEQ ID | Target starting position | Target ending position | Sequence | ATXN3 expression ratio (3 μM) |
|---|---|---|---|---|---|
| 140 | 142 | 38599 | 38616 | AmsMmsGmsGdsAdsMdsAdsTdsTdsGdsTdsGdsGdsAdsGdsGmsTmsGm | 93.2 |
| 141 | 143 | 38600 | 38617 | MmsAmsMmsGdsGdsAdsMdsAdsTdsTdsGdsTdsGdsGdsAdsGmsGmsTm | 87.0 |
| 142 | 144 | 38601 | 38618 | MmsMmsAmsMdsGdsGdsAdsMdsAdsTdsTdsGdsTdsGdsGdsAmsGmsGm | 73.1 |
| 143 | 145 | 38604 | 38621 | MmsMmsTmsMdsMdsAdsMdsGdsGdsAdsMdsAdsTdsTdsGdsTmsGmsGm | 61.6 |
| 144 | 146 | 38606 | 38623 | GmsGmsMmsMdsTdsMdsMdsAdsMdsGdsGdsAdsMdsAdsTdsTmsGmsTm | 72.0 |
| 145 | 147 | 38607 | 38624 | TmsGmsGmsMdsMdsTdsMdsMdsAdsMdsGdsGdsAdsMdsAdsTmsTmsGm | 68.9 |
| 146 | 148 | 40453 | 40470 | GmsTmsMmsAdsTdsAdsTdsGdsGdsTdsMdsAdsGdsGdsGdsTmsAmsTm | 21.6 |
| 147 | 149 | 40454 | 40471 | TmsGmsTmsMdsAdsTdsAdsTdsGdsGdsTdsMdsAdsGdsGdsGmsTmsAm | 51.7 |
| 148 | 150 | 40455 | 40472 | AmsTmsGmsTdsMdsAdsTdsAdsTdsGdsGdsTdsMdsAdsGdsGmsGmsTm | 46.9 |
| 149 | 151 | 40456 | 40473 | TmsAmsTmsGdsTdsMdsAdsTdsAdsTdsGdsGdsTdsMdsAdsGmsGmsGm | 51.3 |
| 150 | 152 | 40475 | 40492 | TmsGmsMmsMdsMdsAdsGdsGdsAdsGdsTdsAdsTdsAdsGdsAmsTmsGm | 69.5 |
| 151 | 153 | 40539 | 40556 | TmsAmsMmsAdsGdsMdsAdsMdsTdsTdsAdsMdsGdsGdsAdsGmsTmsGm | 71.3 |
| 152 | 154 | 40540 | 48557 | TmsTmsAmsMdsAdsGdsMdsAdsMdsTdsTdsAdsMdsGdsGdsAmsGmsTm | 82.7 |
| 153 | 155 | 41281 | 41298 | GmsMmsTmsAdsTdsGdsGdsAdsTdsGdsTdsAdsMdsTdsAdsMmsAmsGm | 56.9 |
| 154 | 156 | 41392 | 41409 | AmsAmsGmsAdsMdsMdsMdsTdsTdsTdsGdsAdsGdsGdsMdsTmsTmsTm | 63.6 |
| 155 | 157 | 41393 | 41410 | TmsAmsAmsGdsAdsMdsMdsMdsTdsTdsTdsGdsAdsGdsGdsMmsTmsTm | 58.3 |
| 156 | 158 | 45892 | 45909 | GmsTmsAmsGdsMdsTdsMdsTdsTdsGdsGdsMdsAdsMdsTdsAmsGmsMm | 57.0 |

TABLE 2

| Compound ID | SEQ ID | Target starting position | Target ending position | Sequence | ATXN3 expression ratio (10 μM) |
|---|---|---|---|---|---|
| 157 | 159 | 1512 | 1527 | TmsMmsMmsGdsAdsGdsAdsTdsGdsTdsTdsTdsTdsMmsTmsAm | 47.8 |
| 158 | 160 | 1521 | 1536 | TmsMmsAmsAdsAdsAdsGdsTdsTdsTdsCdsCdsGdsAmsGmsAm | 56.4 |
| 159 | 161 | 1568 | 1583 | MmsAmsAmsCdsTdsAdsTdsAdsCdsGdsAdsCdsTdsGmsAmsGm | 74.6 |
| 160 | 162 | 2051 | 2066 | TmsMmsAmsGdsGdsAdsAdsGdsTdsAdsGdsTdsGdsTmsGmsGm | 62.1 |
| 161 | 163 | 2162 | 2177 | TmsTmsMmsGdsGdsGdsTdsAdsAdsGdsTdsAdsGdsAmsTmsTm | 49.4 |
| 162 | 164 | 3931 | 3946 | GmsMmsAmsCdsTdsAdsTdsCdsTdsGdsCdsCdsAdsGmsGmsGm | 63.6 |
| 163 | 165 | 4038 | 4053 | GmsTmsMmsAdsAdsTdsCdsTdsAdsGdsCdsAdsGdsMmsAmsTm | 65.3 |
| 164 | 166 | 4259 | 4274 | MmsTmsTmsCdsAdsTdsTdsGdsTdsGdsTdsTdsGdsGmsGmsMm | 83.8 |
| 165 | 167 | 4277 | 4292 | TmsAmsTmsGdsAdsTdsTdsTdsTdsAdsGdsGdsCdsMmsMmsAm | 66.9 |
| 166 | 168 | 5668 | 5683 | TmsMmsAmsGdsTdsTdsTdsGdsGdsAdsGdsTdsTdsTmsAmsMm | 34.2 |
| 167 | 169 | 5762 | 5777 | GmsAmsTmsTdsTdsGdsTdsGdsTdsGdsCdsTdsCdsMmsTmsMm | 35.7 |
| 168 | 170 | 7602 | 7617 | GmsMmsTmsTdsTdsCdsCdsCdsAdsTdsGdsCdsTdsAmsMmsMm | 81.8 |
| 169 | 171 | 7817 | 7832 | GmsMmsTmsCdsAdsCdsTdsCdsCdsTdsGdsGdsAdsMmsAmsAm | 85.0 |
| 170 | 172 | 9925 | 9940 | AmsMmsGmsTdsGdsCdsGdsAdsTdsAdsAdsTdsCdsTmsTmsMm | 85.1 |
| 171 | 173 | 10273 | 10288 | AmsGmsAmsAdsAdsTdsGdsTdsAdsAdsGdsCdsCdsGmsGmsGm | 68.3 |
| 172 | 174 | 10409 | 10424 | GmsTmsMmsAdsTdsTdsAdsGdsCdsGdsTdsGdsCdsAmsTmsAm | 80.1 |
| 173 | 175 | 10556 | 10571 | TmsGmsGmsGdsAdsTdsGdsTdsAdsAdsGdsCdsAdsAmsMmsAm | 85.5 |

TABLE 2-continued

| Compound ID | SEQ ID | Target starting position | Target ending position | Sequence | ATXN3 expression ratio (10 μM) |
|---|---|---|---|---|---|
| 174 | 176 | 10584 | 10599 | GmsAmsMmsTdsAdsTdsTdsGdsAdsAdsAdsGdsGdsMmsTmsGm | 56.6 |
| 175 | 177 | 11002 | 11017 | AmsTmsGmsCdsCdsCdsCdsAdsCdsTdsCdsTdsAdsAmsTmsAm | 52.9 |
| 176 | 178 | 11617 | 11632 | TmsMmsTmsGdsGdsAdsTdsAdsCdsAdsAdsCdsTdsMmsAmsMm | 64.2 |
| 177 | 179 | 11650 | 11665 | AmsGmsAmsTdsAdsGdsGdsTdsCdsGdsCdsTdsCdsAmsGmsGm | 29.3 |
| 178 | 180 | 11654 | 11669 | GmsMmsAmsGdsAdsGdsAdsTdsAdsGdsGdsTdsCdsGmsMmsTm | 64.9 |
| 179 | 181 | 11738 | 11753 | MmsAmsMmsGdsGdsTdsAdsAdsAdsGdsCdsAdsCdsTmsAmsGm | 57.9 |
| 180 | 182 | 11744 | 11759 | MmsAmsGmsTdsGdsGdsCdsAdsCdsGdsGdsTdsAdsAmsAmsGm | 55.5 |
| 181 | 183 | 11810 | 11825 | GmsAmsAmsAdsCdsGdsCdsCdsAdsAdsGdsTdsGdsMmsTmsGm | 80.0 |
| 182 | 184 | 12076 | 12091 | TmsAmsAmsGdsTdsTdsCdsTdsCdsCdsCdsTdsGdsGmsGmsMm | 26.2 |
| 183 | 185 | 13141 | 13156 | AmsTmsGmsAdsAdsCdsGdsTdsCdsTdsCdsTdsGdsMmsAmsGm | 67.8 |
| 184 | 186 | 14074 | 14089 | TmsTmsGmsAdsCdsAdsCdsTdsAdsTdsTdsTdsCdsAmsGmsGm | 40.8 |
| 185 | 187 | 14213 | 14228 | AmsTmsAmsGdsCdsTdsTdsGdsCdsTdsCdsAdsAdsGmsAmsMm | 30.4 |
| 186 | 188 | 14325 | 14340 | GmsMmsTmsGdsCdsAdsTdsGdsTdsAdsTdsCdsAdsMmsTmsAm | 58.2 |
| 187 | 189 | 15114 | 15129 | GmsMmsTmsAdsAdsGdsTdsAdsGdsGdsTdsGdsAdsMmsTmsTm | 57.9 |
| 188 | 190 | 15124 | 15139 | TmsTmsAmsGdsGdsAdsTdsGdsAdsAdsGdsCdsTdsAmsAmsGm | 72.5 |
| 189 | 191 | 16211 | 16226 | MmsTmsGmsCdsAdsCdsTdsCdsGdsGdsCdsCdsCdsTmsAmsAm | 57.0 |
| 190 | 192 | 16740 | 16755 | AmsGmsAmsTdsTdsCdsCdsAdsAdsTdsTdsGdsTdsGmsAmsGm | 29.4 |
| 191 | 193 | 18015 | 18030 | AmsGmsMmsCdsTdsAdsTdsCdsAdsCdsCdsAdsCdsGmsTmsMm | 42.5 |
| 192 | 194 | 18033 | 18048 | MmsAmsGmsCdsGdsTdsCdsAdsCdsCdsCdsAdsAdsAmsTmsMm | 30.2 |
| 193 | 195 | 18108 | 18123 | TmsAmsMmsTdsTdsAdsGdsAdsAdsGdsGdsGdsCdsTmsGmsMm | 79.8 |
| 194 | 196 | 19166 | 19181 | GmsMmsMmsTdsAdsGdsTdsCdsAdsCdsTdsTdsTdsGmsAmsTm | 50.7 |
| 195 | 197 | 20832 | 20847 | TmsMmsAmsGdsGdsGdsTdsAdsGdsAdsTdsGdsTdsMmsAmsAm | 38.1 |
| 196 | 198 | 20839 | 20854 | TmsAmsGmsGdsTdsGdsTdsTdsCdsAdsGdsGdsGdsTmsAmsGm | 37.0 |
| 197 | 199 | 20848 | 20863 | AmsGmsTmsCdsAdsAdsAdsGdsCdsTdsAdsGdsGdsTmsGmsTm | 48.2 |
| 198 | 200 | 21487 | 21502 | AmsAmsTmsGdsGdsAdsTdsAdsCdsTdsCdsTdsGdsMmsMmsMm | 55.6 |
| 199 | 201 | 22116 | 22131 | TmsMmsMmsCdsCdsAdsAdsGdsCdsTdsAdsGdsAdsTmsGmsMm | 66.0 |
| 200 | 202 | 22194 | 22209 | AmsMmsGmsTdsGdsTdsGdsGdsTdsTdsTdsGdsCdsAmsTmsMm | 39.3 |
| 201 | 203 | 22199 | 22214 | GmsTmsMmsAdsAdsAdsCdsGdsTdsGdsTdsGdsGdsTmsTmsTm | 22.6 |
| 202 | 204 | 22203 | 22218 | AmsGmsGmsTdsGdsTdsCdsAdsAdsAdsCdsGdsTdsGmsTmsGm | 22.1 |
| 203 | 205 | 22210 | 22225 | MmsTmsAmsTdsTdsTdsAdsAdsGdsGdsTdsGdsTdsMmsAmsAm | 70.6 |
| 204 | 206 | 22998 | 23013 | AmsTmsMmsAdsGdsAdsCdsTdsGdsCdsCdsTdsGdsMmsAmsTm | 66.8 |
| 205 | 207 | 26470 | 26485 | GmsMmsAmsCdsTdsTdsAdsCdsAdsAdsGdsGdsCdsTmsGmsGm | 59.3 |
| 206 | 208 | 27062 | 27077 | GmsGmsTmsGdsCdsTdsGdsCdsTdsAdsAdsTdsAdsTmsAmsMm | 27.6 |
| 207 | 209 | 27271 | 27286 | GmsMmsAmsCdsTdsAdsAdsTdsAdsAdsGdsCdsAdsMmsTmsAm | 48.9 |
| 208 | 210 | 29393 | 29408 | TmsMmsAmsTdsGdsCdsAdsGdsCdsCdsTdsGdsTdsTmsAmsMm | 42.4 |
| 209 | 211 | 30535 | 30550 | AmsAmsGmsCdsAdsCdsTdsAdsGdsTdsTdsAdsTdsTmsGmsMm | 62.8 |
| 210 | 212 | 30556 | 30571 | TmsGmsMmsCdsTdsGdsAdsCdsCdsCdsTdsGdsTdsTmsTmsAm | 45.4 |
| 211 | 213 | 30930 | 30945 | AmsGmsMmsTdsTdsGdsAdsTdsAdsAdsCdsCdsTdsTmsAmsGm | 50.0 |

TABLE 2-continued

| Compound ID | SEQ ID | Target starting position | Target ending position | Sequence | ATXN3 expression ratio (10 μM) |
|---|---|---|---|---|---|
| 212 | 214 | 31576 | 31591 | GmsAmsTmsGdsTdsAdsGdsTdsAdsGdsAdsGdsTdsTmsTmsTm | 13.7 |
| 213 | 215 | 31580 | 31595 | AmsGmsMmsTdsGdsAdsTdsGdsTdsAdsGdsTdsAdsGmsAmsGm | 51.7 |
| 214 | 216 | 32006 | 32021 | GmsTmsTmsGdsGdsTdsTdsTdsGdsTdsGdsGdsTdsAmsMmsTm | 17.1 |
| 215 | 217 | 33237 | 33252 | GmsTmsAmsGdsGdsAdsTdsTdsCdsTdsGdsGdsTdsTmsAmsMm | 43.9 |
| 216 | 218 | 34900 | 34915 | AmsTmsAmsAdsGdsTdsAdsCdsCdsTdsTdsTdsGdsAmsTmsMm | 57.7 |
| 217 | 219 | 35710 | 35725 | GmsAmsAmsGdsGdsTdsAdsGdsCdsGdsAdsAdsCdsAmsTmsGm | 41.7 |
| 218 | 220 | 35841 | 35856 | GmsGmsTmsAdsAdsCdsTdsGdsCdsTdsCdsCdsTdsTmsAmsAm | 21.2 |
| 219 | 221 | 36413 | 36428 | GmsTmsAmsAdsCdsTdsCdsTdsGdsCdsAdsCdsTdsTmsMmsMm | 36.7 |
| 220 | 222 | 36417 | 36432 | GmsAmsAmsAdsGdsTdsAdsAdsCdsTdsCdsTdsGdsMmsAmsMm | 49.2 |
| 221 | 223 | 36426 | 36441 | MmsGmsAmsGdsAdsCdsCdsTdsGdsGdsAdsAdsAdsGmsTmsAm | 51.8 |
| 222 | 224 | 36609 | 36624 | GmsTmsMmsAdsTdsCdsCdsCdsTdsAdsTdsGdsTdsMmsTmsTm | 18.7 |
| 223 | 225 | 37690 | 37705 | GmsTmsGmsTdsTdsTdsTdsGdsGdsCdsTdsGdsTdsAmsMmsTm | 33.0 |
| 224 | 226 | 38556 | 38571 | AmsGmsTmsCdsTdsGdsGdsAdsTdsTdsCdsTdsCdsTmsAmsMm | 47.5 |
| 225 | 227 | 40452 | 40467 | AmsTmsAmsTdsGdsGdsTdsCdsAdsGdsGdsGdsTdsAmsTmsGm | 48.0 |
| 226 | 228 | 40470 | 40485 | GmsAmsGmsTdsAdsTdsAdsGdsAdsTdsGdsCdsTdsAmsTmsGm | 33.6 |
| 227 | 229 | 41285 | 41300 | AmsTmsGmsCdsTdsAdsTdsGdsGdsAdsTdsGdsTdsAmsMmsTm | 75.8 |
| 228 | 230 | 41294 | 41309 | GmsAmsGmsTdsAdsTdsTdsAdsCdsAdsTdsGdsCdsTmsAmsTm | 22.0 |
| 229 | 231 | 42110 | 42125 | TmsTmsTmsCdsTdsAdsTdsTdsTdsGdsAdsGdsCdsAmsMmsGm | 38.2 |
| 230 | 232 | 42805 | 42820 | GmsTmsAmsTdsAdsCdsAdsGdsTdsTdsGdsAdsAdsGmsGmsGm | 69.2 |
| 231 | 233 | 43091 | 43106 | GmsMmsTmsGdsTdsAdsAdsGdsGdsTdsTdsTdsTdsGmsAmsTm | 49.4 |
| 232 | 234 | 43182 | 43197 | GmsGmsAmsGdsAdsCdsTdsTdsGdsCdsCdsTdsGdsMmsAmsTm | 38.7 |
| 233 | 235 | 43209 | 43224 | GmsTmsAmsCdsGdsTdsAdsTdsGdsTdsTdsTdsAdsGmsTmsMm | 66.5 |
| 234 | 236 | 43218 | 43233 | TmsMmsAmsTdsGdsGdsTdsGdsGdsGdsTdsAdsCdsGmsTmsAm | 51.5 |
| 235 | 237 | 43933 | 43948 | GmsTmsGmsTdsAdsAdsGdsGdsGdsAdsAdsAdsCdsTmsTmsMm | 49.5 |
| 236 | 238 | 44050 | 44065 | MmsTmsTmsGdsAdsGdsGdsAdsGdsTdsAdsGdsTmsAmsMm | 59.2 |

TABLE 3

| Compound ID | SEQ ID | Target starting position | Target ending position | Sequence | ATXN3 expression ratio (3 μM) |
|---|---|---|---|---|---|
| 237 | 272 | 11648 | 11665 | AmsGmsAmsTdsAdsGdsGdsTdsMdsGdsMdsTdsMdsAdsGdsGmsAmsGm | 73.3 |
| 238 | 273 | 11649 | 11666 | GmsAmsGmsAdsTdsAdsGdsGdsTdsMdsGdsMdsTdsMdsAdsGmsGmsAm | 56.1 |
| 239 | 274 | 11650 | 11667 | AmsGmsAmsGdsAdsTdsAdsGdsGdsTdsMdsGdsMdsTdsMdsAmsGmsGm | 64.6 |
| 240 | 275 | 20837 | 20854 | TmsAmsGmsGdsTdsGdsTdsTdsMdsAdsGdsGdsGdsTdsAdsGmsAmsTm | 62.1 |
| 241 | 276 | 20838 | 20855 | MmsTmsAmsGdsGdsTdsGdsTdsTdsMdsAdsGdsGdsGdsTdsAmsGmsAm | 77.3 |
| 242 | 277 | 22192 | 22209 | AmsMmsGmsTdsGdsTdsGdsGdsTdsTdsTdsGdsMdsAdsTdsMmsMmsMm | 57.7 |
| 243 | 278 | 22193 | 22210 | AmsAmsMmsGdsTdsGdsTdsGdsGdsTdsTdsTdsGdsMdsAdsTmsMmsMm | 74.5 |
| 244 | 279 | 22194 | 22211 | AmsAmsAmsMdsGdsTdsGdsTdsGdsGdsTdsTdsTdsGdsMdsAmsTmsMm | 70.0 |

TABLE 3-continued

| Compound ID | SEQ ID | Target starting position | Target ending position | Sequence | ATXN3 expression ratio (3 µM) |
|---|---|---|---|---|---|
| 245 | 280 | 22199 | 22216 | GmsTmsGmsTdsMdsAdsAdsAdsMdsGdsTdsGdsTdsGdsGdsTmsTmsTm | 54.2 |
| 246 | 281 | 22201 | 22218 | AmsGmsGmsTdsGdsTdsMdsAdsAdsAdsMdsGdsTdsGdsTdsGmsGmsTm | 48.9 |
| 247 | 282 | 22202 | 22219 | AmsAmsGmsGdsTdsGdsTdsMdsAdsAdsAdsMdsGdsTdsGdsTmsGmsGm | 54.6 |
| 248 | 283 | 22203 | 22220 | TmsAmsAmsGdsGdsTdsGdsTdsMdsAdsAdsAdsMdsGdsTdsGmsTmsGm | 74.8 |
| 249 | 284 | 32006 | 32023 | AmsAmsGmsTdsTdsGdsGdsTdsTdsTdsGdsTdsGdsGdsTdsAmsMmsTm | 65.9 |
| 250 | 285 | 36412 | 36429 | AmsGmsTmsAdsAdsMdsTdsMdsTdsGdsMdsAdsMdsTdsTdsMmsMmsMm | 65.5 |

TABLE 4

| | compound ID | Target starting position | Target ending position | 3 µM | 10 µM |
|---|---|---|---|---|---|
| WO2018/089805 | 650528 | 44828 | 44845 | 82.0 | 61.8 |
| WO2019/217708 | 1100673 | 43010 | 43029 | 52.4 | 35.4 |
| WO2020/172559 | 1287095 | 44221 | 44240 | 41.7 | 29.0 |

REFERENCE EXAMPLE

Scheme of methods for synthesizing ALNA[Ms]-containing nucleosides, ALNA[mU]-containing nucleosides, ALNA[ipU]-containing nucleosides, ALNA[Trz]-containing nucleosides, and ALNA[Oxz]-containing nucleosides are shown below. The starting compounds (1a, 1d, and 1g) can be synthesized using a method described in WO 2017/047816.

Synthesis of ALNA[Ms]-T

[Chemical Formula 21]

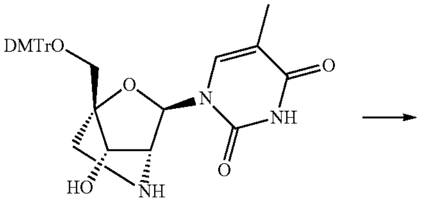

1a

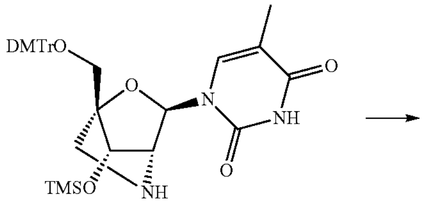

2Ta

-continued

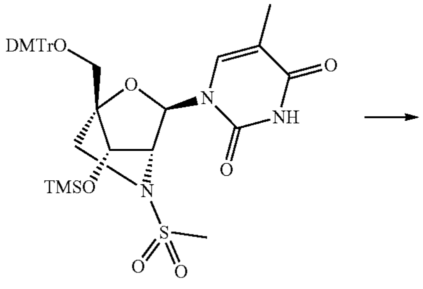

2Tb

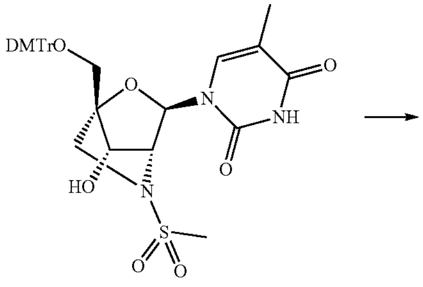

2Tc

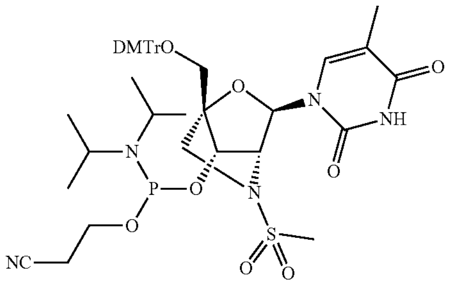

2Td

Synthesis of ALNA[Ms]-mC
[Chemical Formula 22]
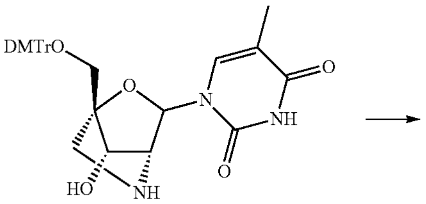
1a
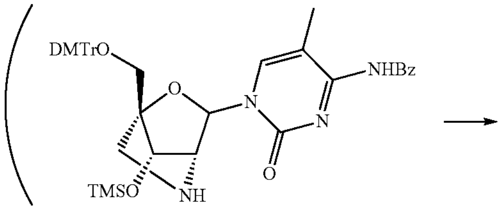
2mCa
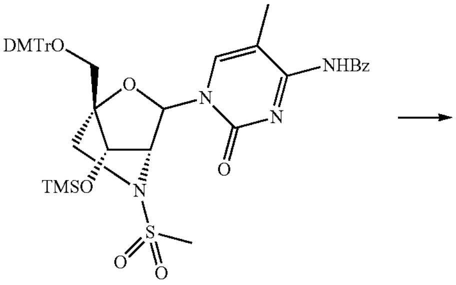
2mCb
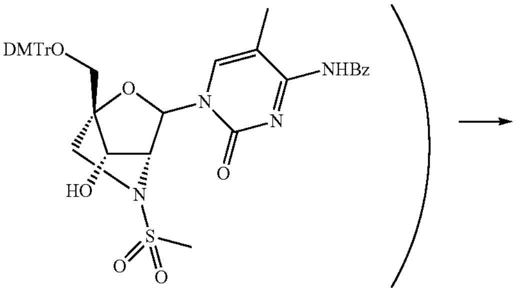
2mCc
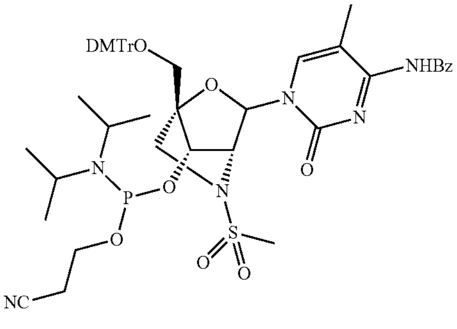
2mCd
Synthesis of ALNA[Ms]-G
[Chemical Formula 23]
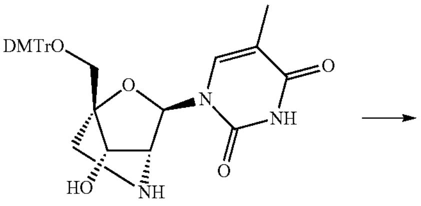
1a
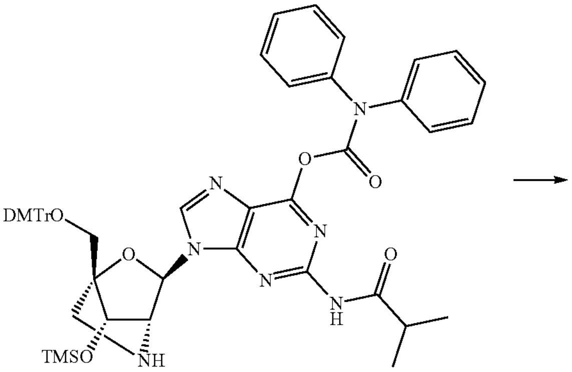
2Ga
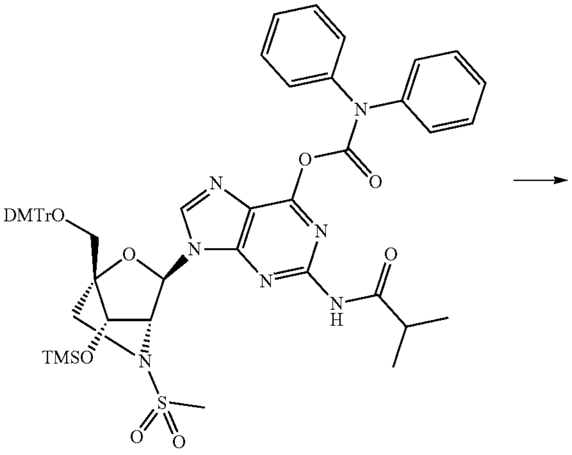
2Gb
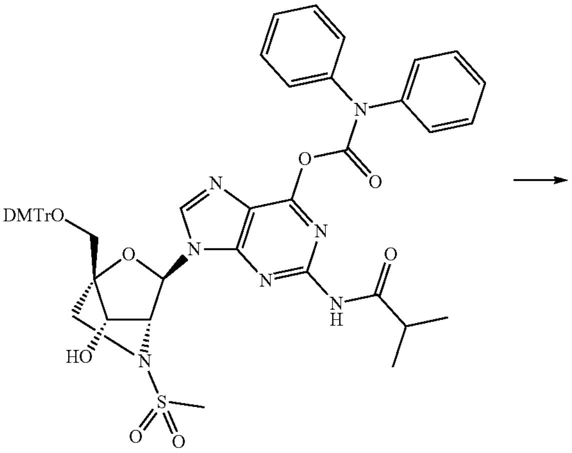
2Gc -continued
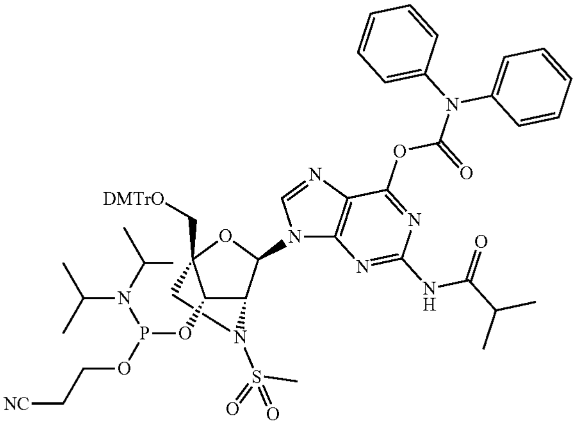
2Gd
Synthesis of ALNA[Ms]-A
[Chemical Formula 24]
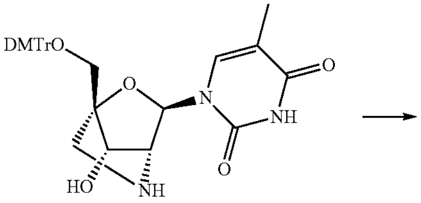
1a
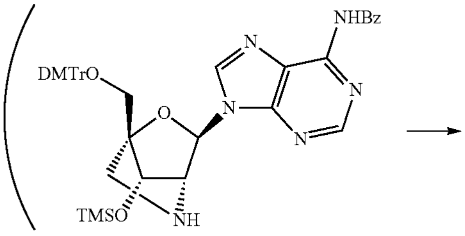
2Aa
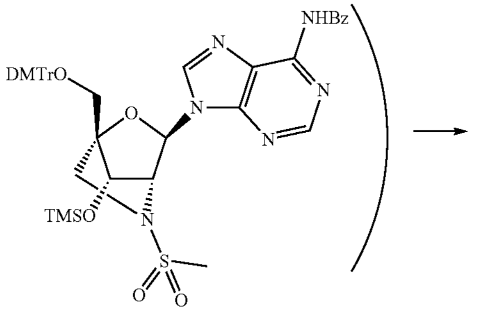
2Ab
-continued
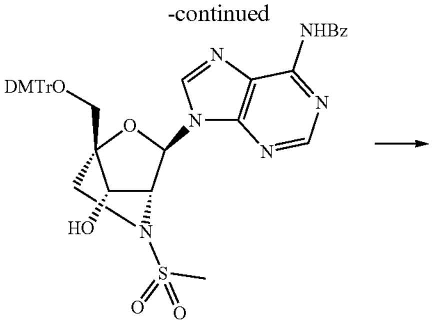
2Ac
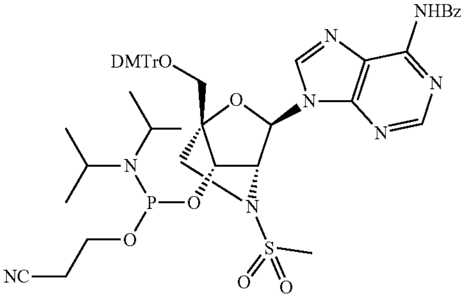
2Ad
Synthesis of ALNA[mU]-T
[Chemical Formula 25]
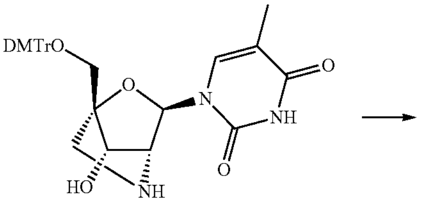
1a
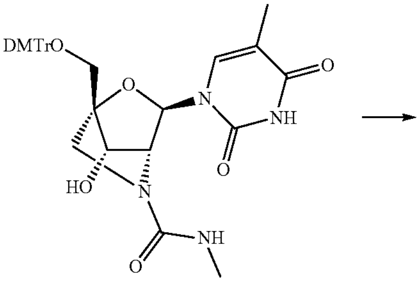
4Tc
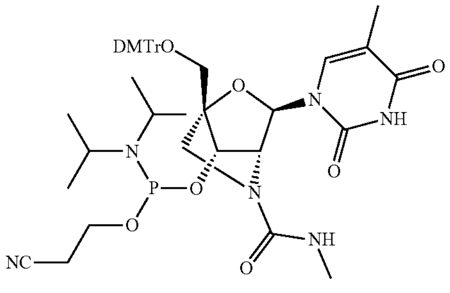
4Td Synthesis of ALNA[mU]-mC
[Chemical Formula 26]
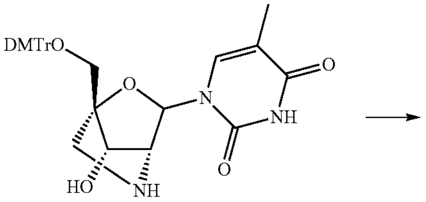
1a
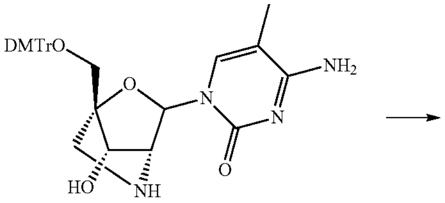
4mCa
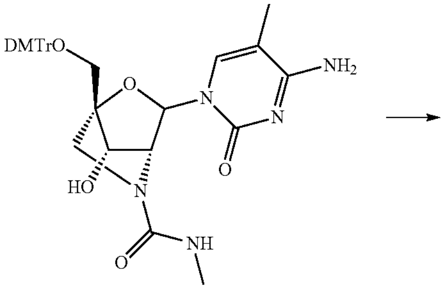
4mCb
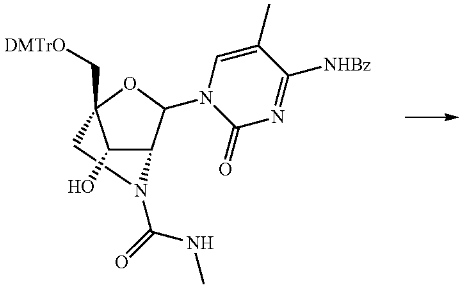
4mCc
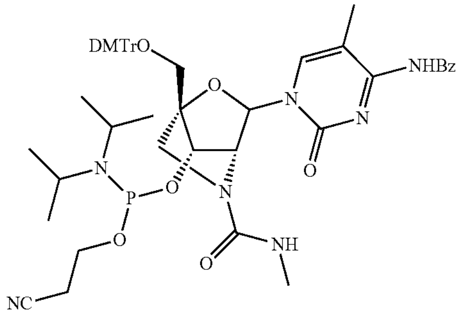
4mCd
Synthesis of ALNA[mU]-G
[Chemical Formula 27]
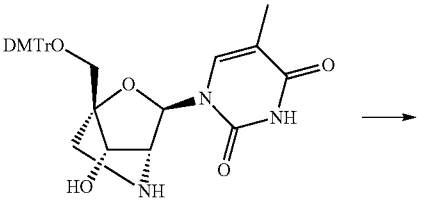
1a
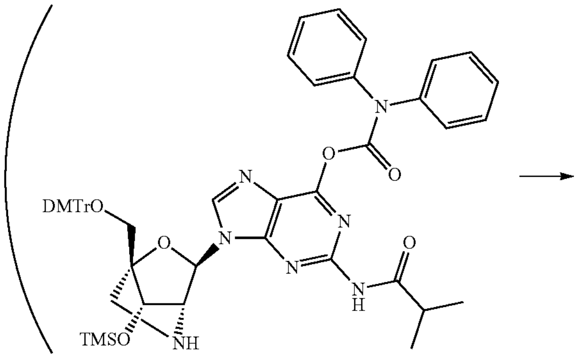
4Ga
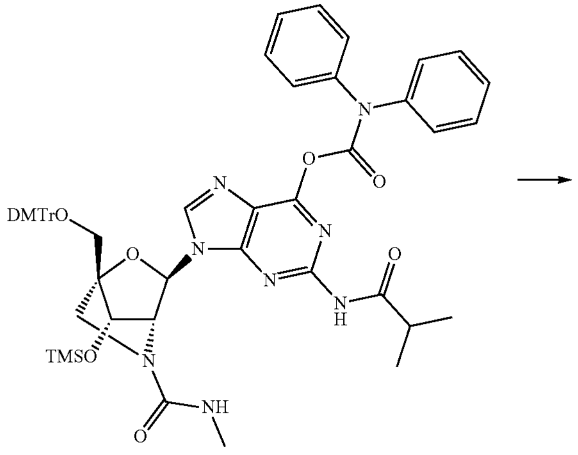
4Gb
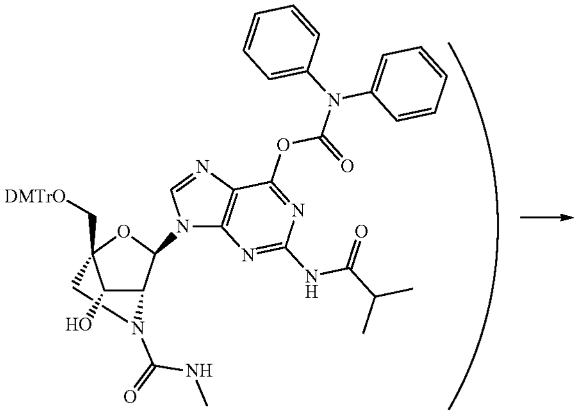
4Gc -continued
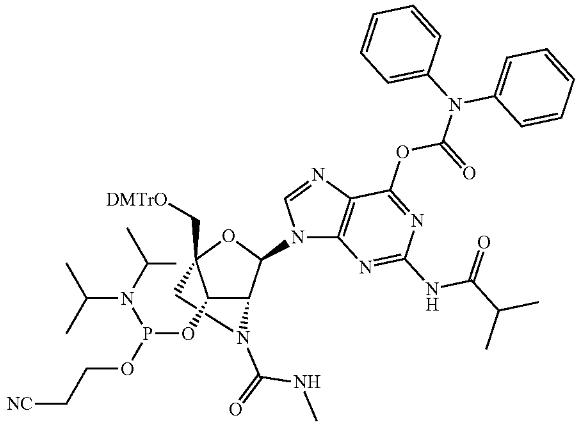
4Gd
Synthesis of ALNA [mU]-A
[Chemical Formula 28]
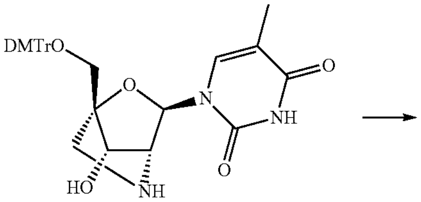
1a
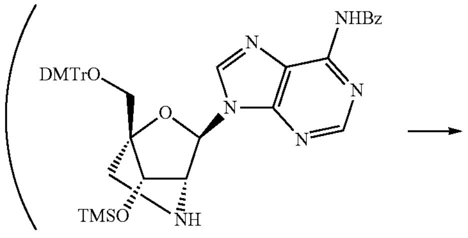
4Aa
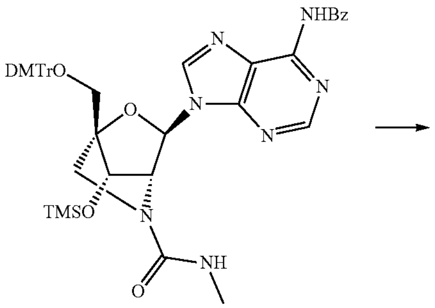
4Ab
-continued
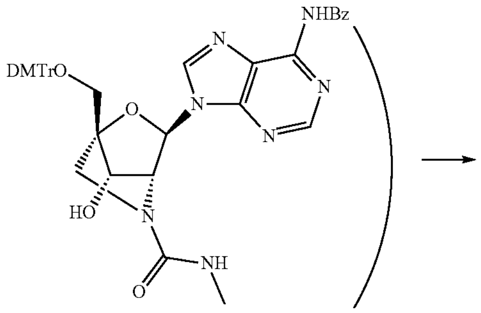
4Ac
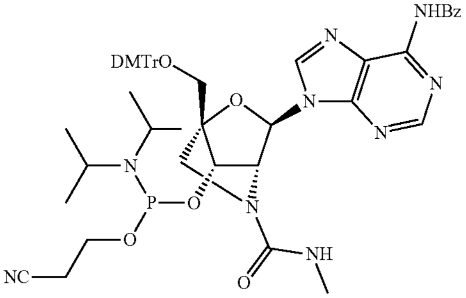
4Ad
Synthesis of ALNA [ipU]-T
[Chemical Formula 29]
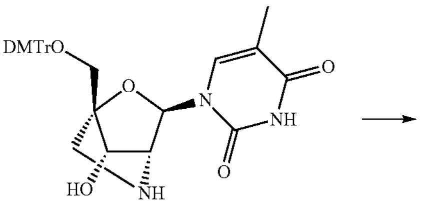
1a
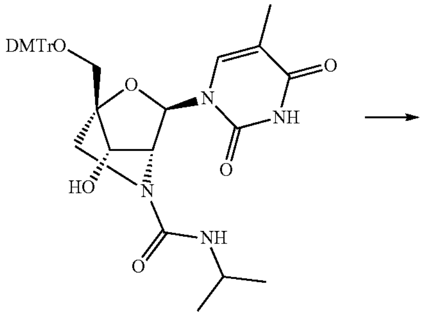
5Tc -continued
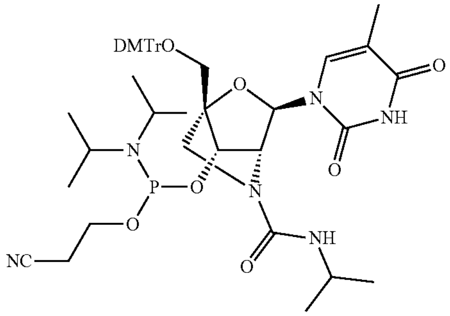
5Td
Synthesis of ALNA[ipU]-mC
[Chemical Formula 30]
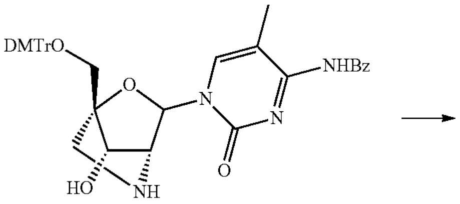
1c
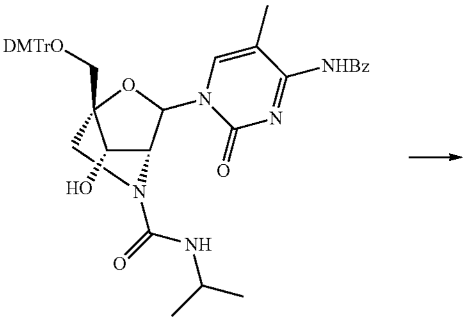
5mCc
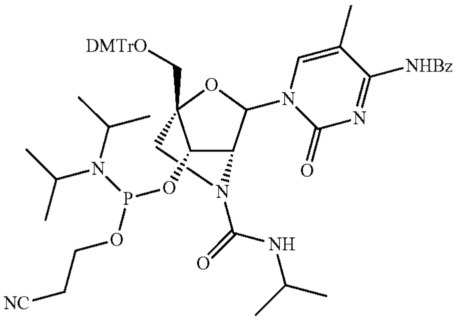
5mCd
Synthesis ALNA[ipU]-G
[Chemical Formula 31]
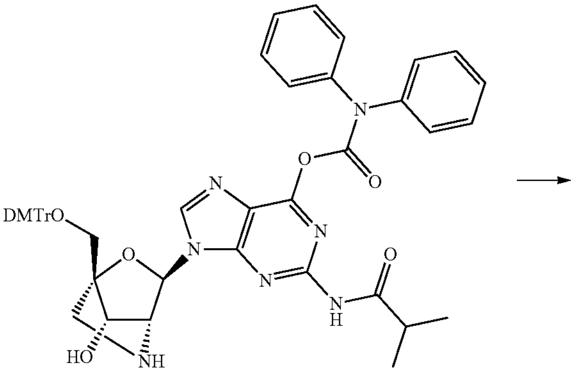
1d
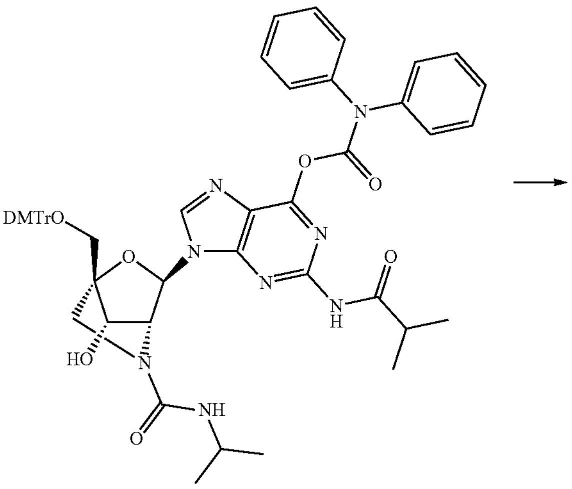
5Gc
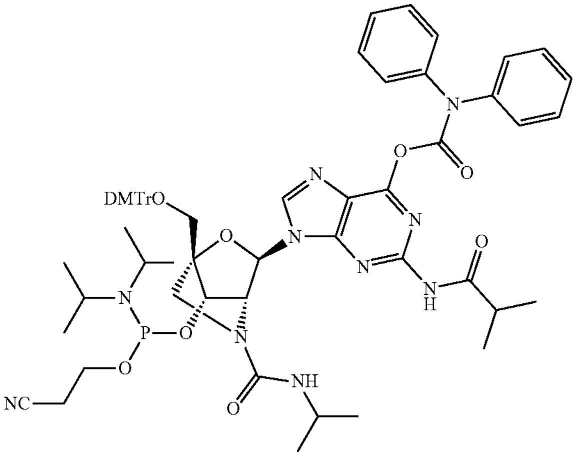
5Gd Synthesis of ALNA[ipU]-A
[Chemical Formula 32]
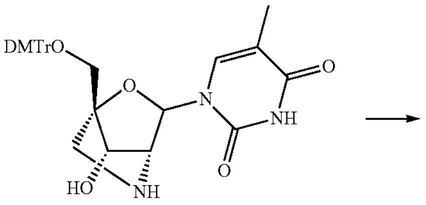
1a
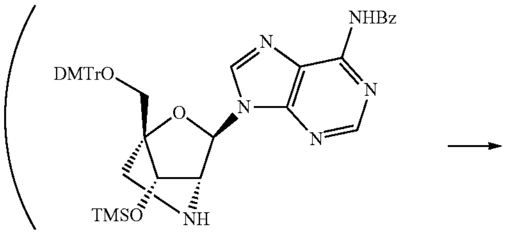
5Aa
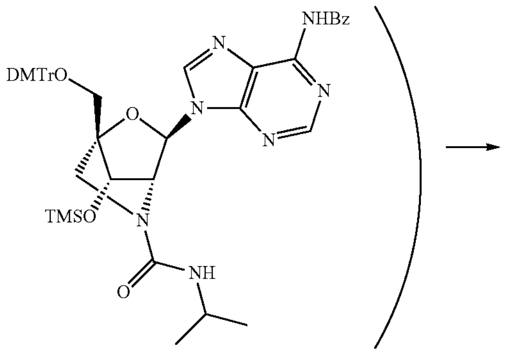
5Ab
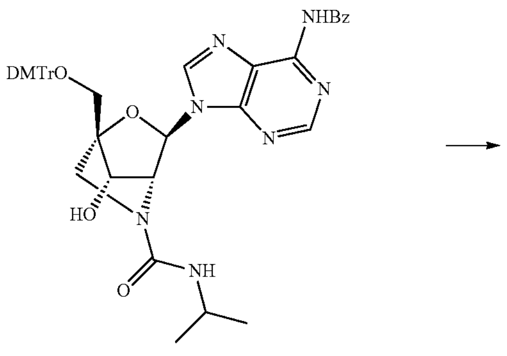
5Ac
-continued
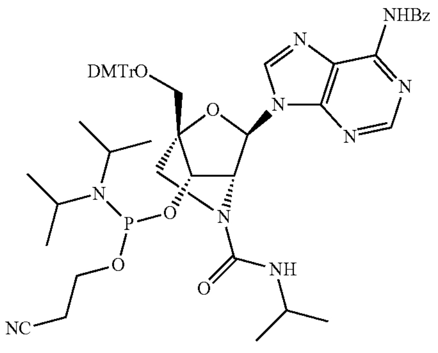
5Ad
Synthesis of ALNA[Trz]-T
[Chemical Formula 33]
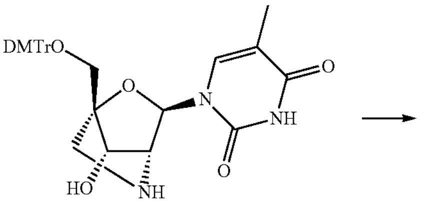
1a
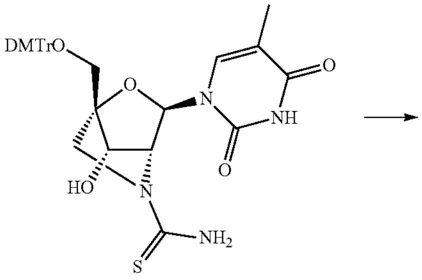
14Ta
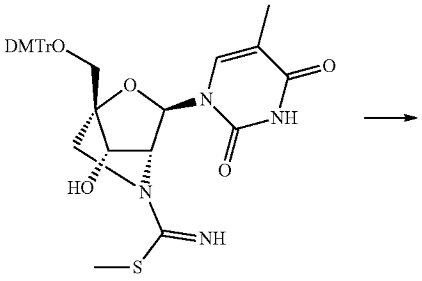
14Tb -continued
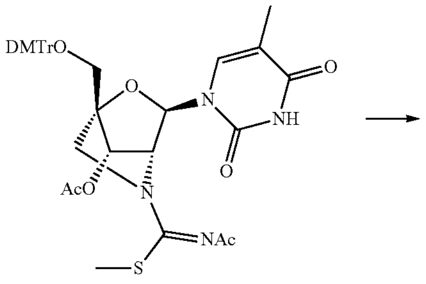
14Tc
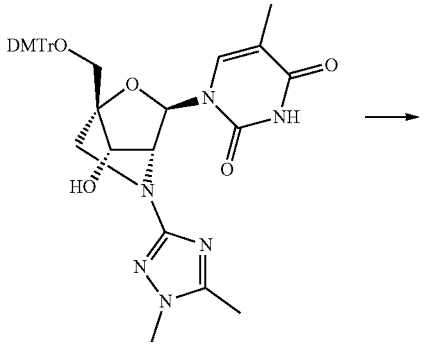
14Td
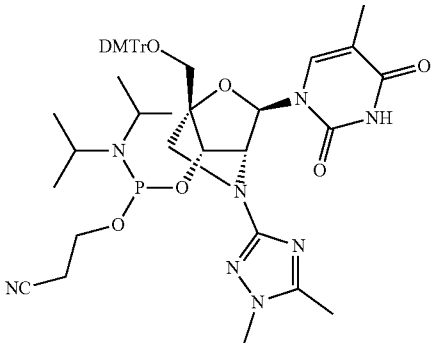
14Te
Synthesis of ALNA[Trz]-mC
[Chemical Formula 34]
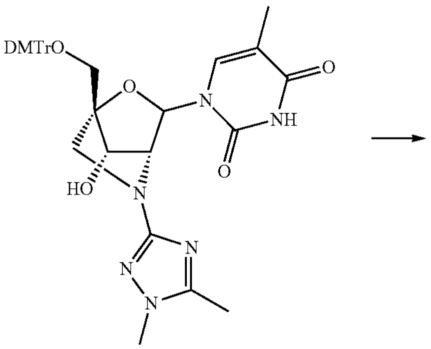
14Td
-continued
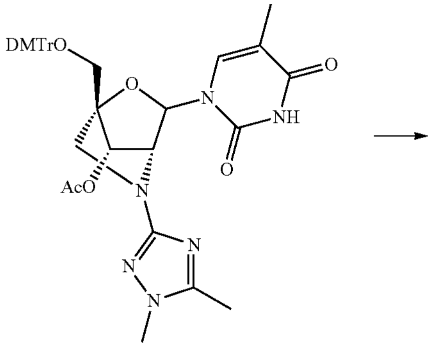
14Ca
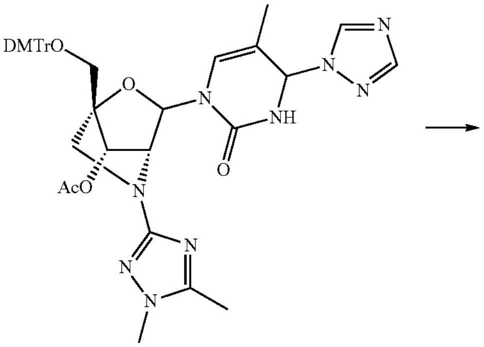
14Cb
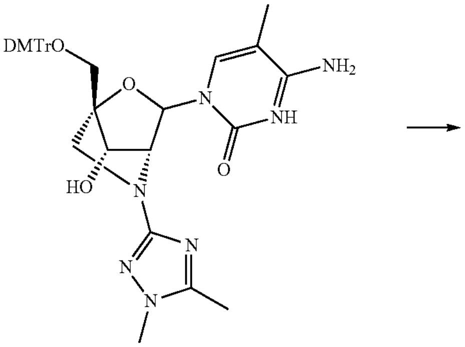
14Cc
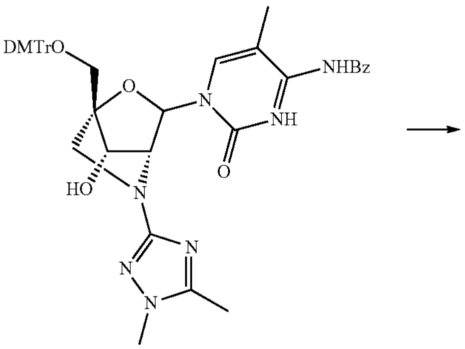
14Cd -continued
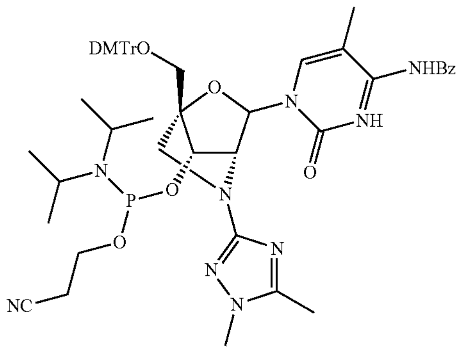
14Ce
Synthesis ALNA[Trz]-G
[Chemical Formula 35]
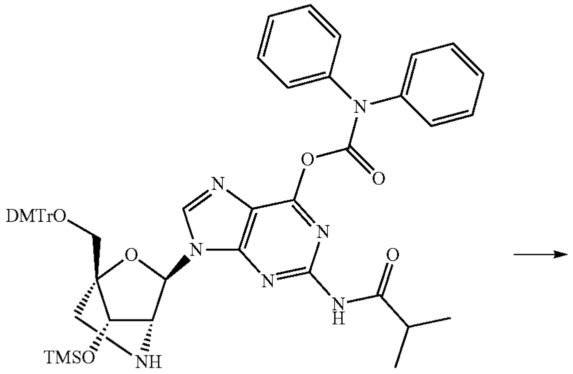
1g
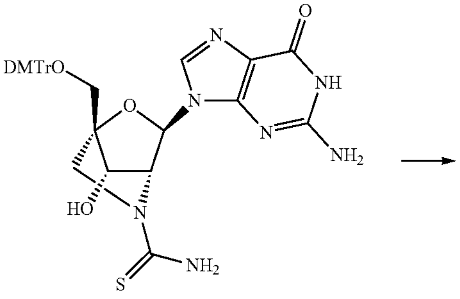
14Ga
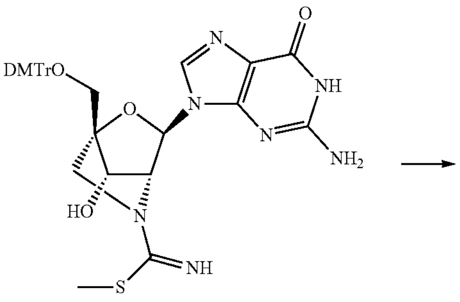
14Gb
-continued
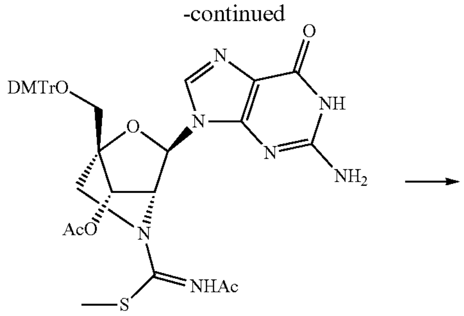
14Gc
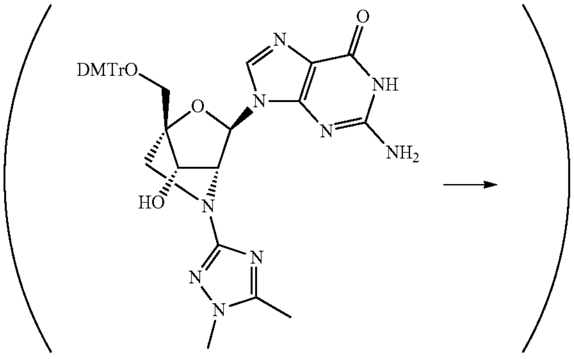
14Gd
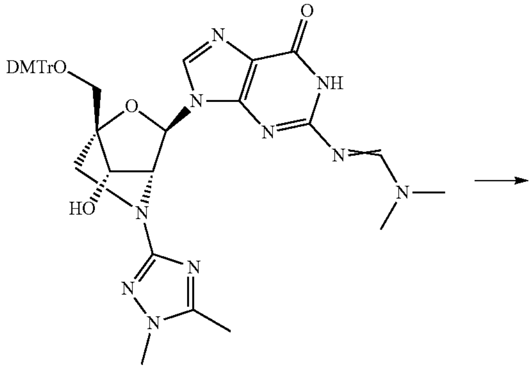
14Ge
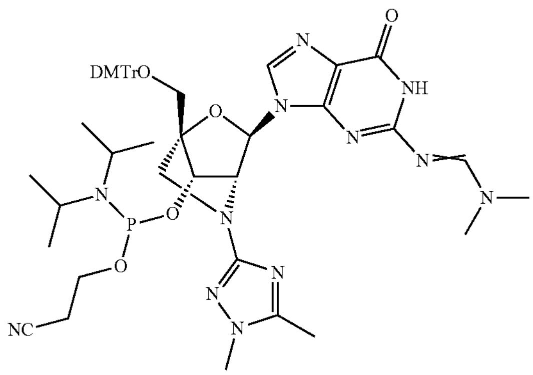
14Gf Synthesis of ALNA[Trz]-A
[Chemical Formula 36]
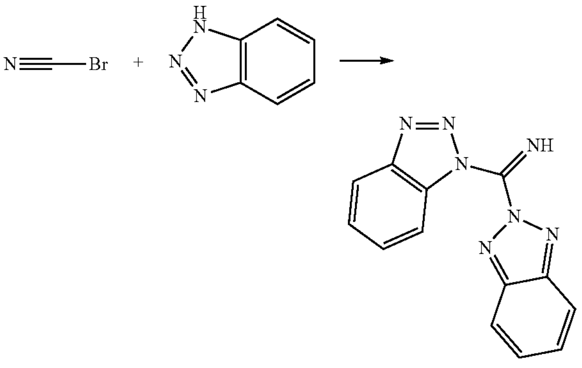
14Aa
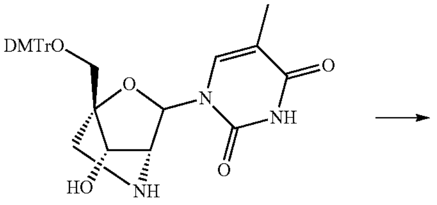
1a
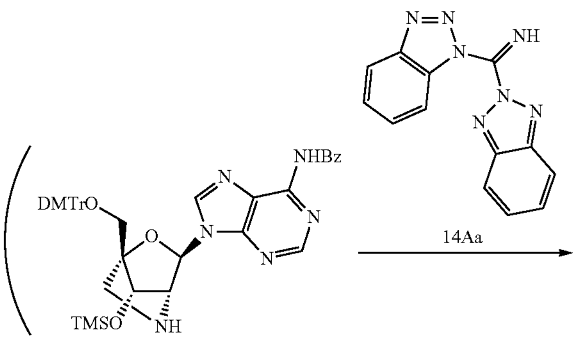
14Gb
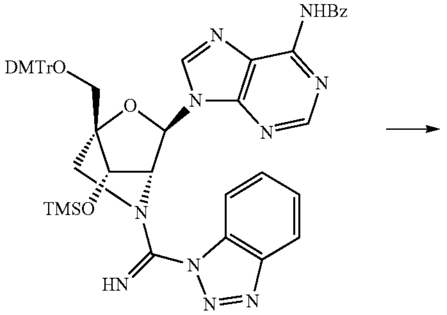
14Gc
-continued
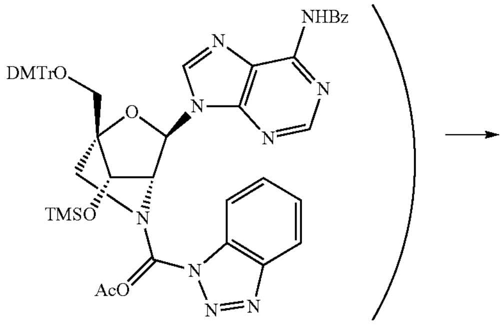
14Gd
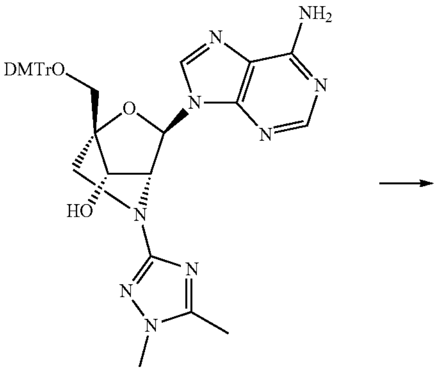
14Ae
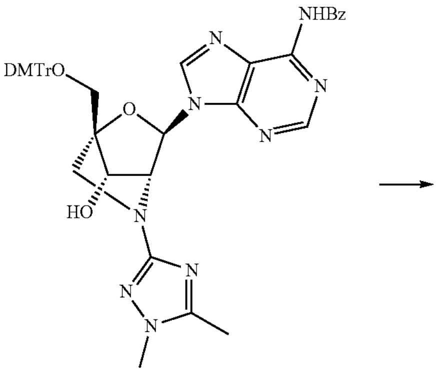
14Af
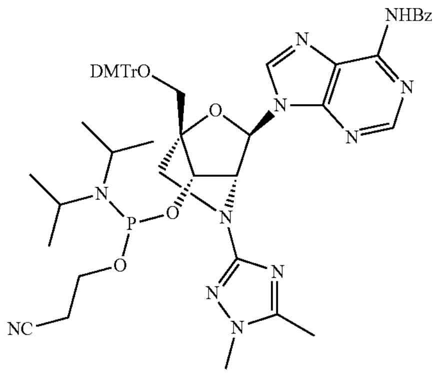
14Ag Synthesis of ALNA[Oxz]-T
[Chemical Formula 37]
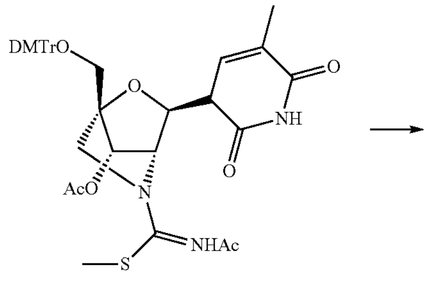
14Tc
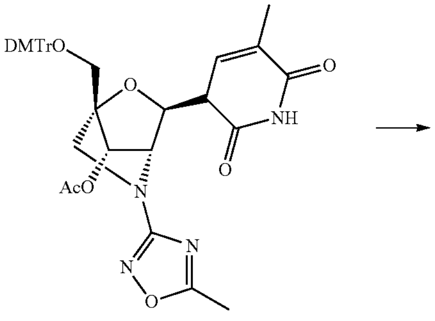
15Ta
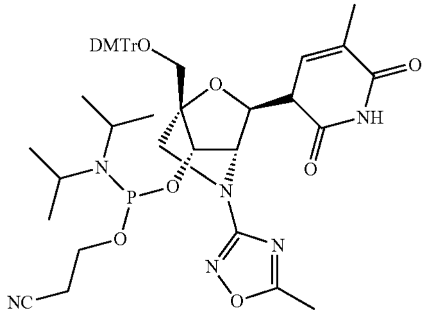
15Tb
Synthesis of ALNA[Oxz]-mC
[Chemical Formula 38]
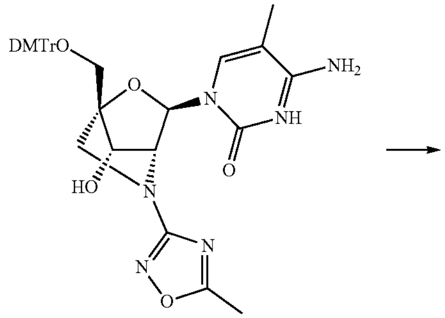
15Ta
-continued
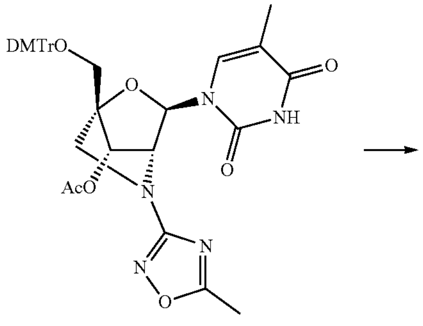
15Ca
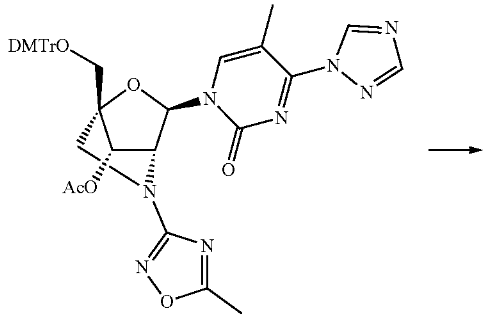
15Cb
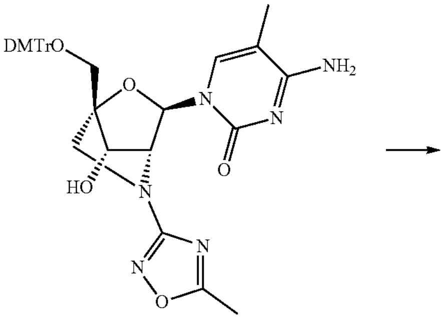
15Cc
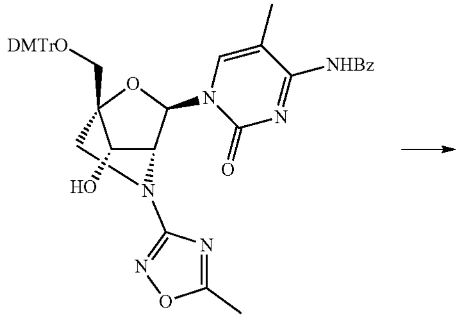
15Cd -continued

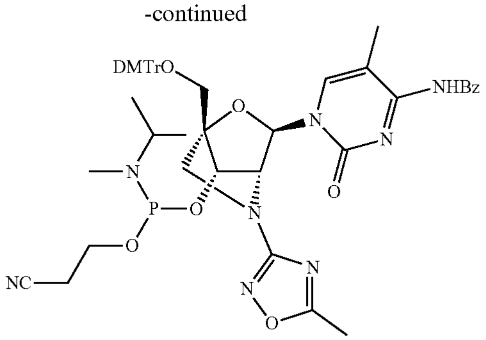

15Ce

In the present specification, unless specifically stated otherwise, the use of a singular form includes a plural form. In the present specification, unless specifically stated otherwise, the use of "or" means "and/or." Further, the use of the term "including" and its other forms such as "includes" and "included" are not limiting. Further, unless specifically stated otherwise, the term "element" or the like includes an element that includes one unit and an element that includes more than one subunit.

Section headings used herein are for organizational purposes only and should not be construed as limiting the subject matter described. All documents or portions of documents cited in this application, including, but not limited to, patents, patent applications, reports, books and articles, are expressly incorporated herein by reference, with respect to the portions of the document discussed herein, and in their entirety.

Unless a specific definition is given, the nomenclature used in connection with analytical chemistry, synthetic organic chemistry, and medical chemistry and pharmaceutical chemistry, and their procedures and techniques described herein are those that are well known in the art and are commonly used. Standard techniques can be used for chemical synthesis and chemical analysis as used herein. Where permitted, all patents, patent applications, published patent applications and other publications referred to throughout the disclosure of this specification, and GenBank accession numbers and relevant sequence information as well as other data available through databases such as the National Center for Biotechnology Information (NCBI), are incorporated by reference with respect to portions of the documents discussed herein, and in its entirety.

Further, this specification is filed together with a sequence listing in electronic format. However, the information of the sequence listing described in the electronic format is incorporated herein by reference in its entirety.

The invention claimed is:

1. A modified oligonucleotide having an activity of inhibiting Ataxin 3 (ATXN3) expression, comprising:

a 3' wing segment comprising nucleosides including a modified sugar;

a 5' wing segment comprising nucleosides including a modified sugar; and a gap segment positioned between the 5' wing segment and the 3' wing segment, wherein a nucleobase sequence of the modified oligonucleotide is a nucleobase sequence selected from the group consisting of (1) TCGGGTAAGTAGATTTTC (complementary sequence of 2159-2176 of SEQ ID NO: 1) (SEQ ID NO: 239 of the sequence listing), (5) AGGTTATAGGATGCAGGT (complementary sequence of 5845-5862 of SEQ ID NO: 1) (SEQ ID NO: 243 of the sequence listing), (6) GAAGCTAAGTAGGTGACT (complementary sequence of 15115-15132 of SEQ ID NO: 1) (SEQ ID NO: 244 of the sequence listing),

(22) GTCATCCCTATGTCTTAT (complementary sequence of 36607-36624 of SEQ ID NO: 1) (SEQ ID NO: 259 of the sequence listing),

(23) GTCATATGGTCAGGGTAT (complementary sequence of 40453-40470 of SEQ ID NO: 1) (SEQ ID NO: 260 of the sequence listing),

(24) TGTCATATGGTCAGGGTA (complementary sequence of 40454-40471 of SEQ ID NO: 1) (SEQ ID NO: 261 of the sequence listing),

(25) ATGTCATATGGTCAGGGT (complementary sequence of 40455-40472 of SEQ ID NO: 1) (SEQ ID NO: 262 of the sequence listing), and

(26) TATGTCATATGGTCAGGG (complementary sequence of 40456-40473 of SEQ ID NO: 1) (SEQ ID NO: 263 of the sequence listing)

or a nucleobase sequence of 17 contiguous bases contained in the nucleobase sequence.

2. The modified oligonucleotide according to claim 1, wherein the modified oligonucleotide is single-stranded.

3. The modified oligonucleotide according to claim 1, wherein at least one nucleoside forming the modified oligonucleotide includes a modified sugar.

4. The modified oligonucleotide according to claim 3, wherein the modified sugar is selected from the group consisting of a bicyclic sugar, a 2'-MOE (2'-O-methoxyethyl) modified sugar, and a 2'-OMe modified sugar.

5. The modified oligonucleotide according to claim 4, wherein the bicyclic sugar is selected from sugar moieties of LNA, GuNA, ALNA[Ms], ALNA[mU], ALNA[ipU], ALNA[Oxz], or ALNA[Trz].

6. The modified oligonucleotide according to claim 1, wherein at least one nucleoside forming the modified oligonucleotide includes a modified nucleobase.

7. The modified oligonucleotide according to claim 6, wherein the modified nucleobase is 5-methylcytosine.

8. The modified oligonucleotide according to claim 1, wherein at least one internucleoside linkage forming the modified oligonucleotide is a modified internucleoside linkage.

9. The modified oligonucleotide according to claim 8, wherein the modified internucleoside linkage is a phosphorothioate internucleoside linkage.

10. A pharmaceutical composition, comprising:

the modified oligonucleotide of claim 1 or a pharmaceutically acceptable salt thereof; and a pharmaceutically acceptable carrier.

11. A method for treating, preventing, or delaying progression of an ATXN3-related disease, comprising:

administering an effective amount of the pharmaceutical composition of claim 10 to a subject in need thereof.

12. The method according to claim 11, wherein the ATXN3-related disease is a neurodegenerative disease.

13. The method according to claim 12, wherein the neurodegenerative disease is spinocerebellar ataxia type 3.

14. A method for treating, preventing or delaying progression of an ATXN3-related disease, comprising:

administering an effective amount of the modified oligonucleotide of claim 1 or a pharmaceutically acceptable salt thereof to a subject in need thereof.

15. The method according to claim 14, wherein the ATXN3-related disease is a neurodegenerative disease.

16. The method according to claim 15, wherein the neurodegenerative disease is spinocerebellar ataxia type 3.

17. The modified oligonucleotide according to claim 2, wherein at least one nucleoside forming the modified oligonucleotide includes a modified sugar.

18. The modified oligonucleotide according to claim 17, wherein the modified sugar is selected from the group consisting of a bicyclic sugar, a 2'-MOE (2'-O-methoxyethyl) modified sugar, and a 2'-OMe modified sugar.

19. The modified oligonucleotide according to claim 18, wherein the bicyclic sugar is selected from sugar moieties of LNA, GuNA, ALNA[Ms], ALNA[mU], ALNA[ipU], ALNA[Oxz], or ALNA[Trz].

* * * * *

SEQUENCE LISTING

```
<160> NUMBER OF SEQ ID NOS: 285

<210> SEQ ID NO 1
<211> LENGTH: 48070
<212> TYPE: DNA
<213> ORGANISM: Homo sapiens

<400> SEQUENCE: 1

gagaggggca gggggcggag ctggaggggg tggttcggcg tgggggccgt tggctccaga     60

caaataaaca tggagtccat cttccacgag aaagtgagtg tccgcgttcg gtggggagct    120

gtctgccgcg cggtggcggg cgtggagcgc ggcatcaccg cctctcggag ggctgggtgg    180

ggcccgagtc gcccccatgc cgatctcgcc cggcgagggg cgacgccgca gcctcccgcc    240

tcctcggctc gaggagggga gcatcaccta cgcccctact tcccccgcgg cccccgccct    300

gggagccggg agggagtatg ggcggggccg ggggcgtctc gggacacggg agtggggtgg    360

cgcccagtgg gtttgcttct gcctttctcc gtcactttcc atcgcttttc ggaggattcc    420

ttcacccctc cccaatcctt ccctctccct agggtctagc tagagtcatc tctgggacac    480

ctccctcaac ccctcctacc ctaatcctgg cagaattaac ttttcctcct ccggactgct    540

caattctata ttggagtctt ccctacacgt agatctttgg ggtcttgttc gtgtctttcc    600

cctgcactag gtccgcgagc ctcccgaggg aggagacctt ggctcgccca ctgtagggcc    660

tgacatttag gaagtgaagt aggaaacccg gcgtgcccct aaacagggaa gtcgtcacaa    720

gagtttttat tacgggatgt ttgggtttgg tttcttttgg tactcccatc tttccggagc    780

aggcggccag ctttgttttt aggtattagg agtggactgg gatgattttg ttgtagtctg    840

cctagcctgc tgtcccttta actcttccgt gaccatgcac ttgaagatac tgtttgtgat    900

atgtaaagaa actcctcgtt tctctcatac tattatccag ccatttgtgt gtgagtgaag    960

ccttccccag gacagctttg gcacatggta tcatgtttca taatagtttc gtgtttggaa   1020

agagttgctg gtaaggctgt tatttaatag gaggagcaaa gggtttttgt tttattaaat   1080
```

```
actttataaat gatcatttat cccagacatt taaaattcac acacacacaa caaataaagc   1140
aaagacaaaa gaatacattt accaaatgta aatctgtagc ataaattttt tttaattttt   1200
attttaaaga tggggtctca ttctgtcacc caggcaggtg tgcaatggag agatcatggc   1260
tcactgcagc cttgatctcc taggcacaag cgatcctccc gcctctgcct ccagagtagc   1320
tgggactaca ggtgcatatc gccagggcca ggtaatgttt ttgggagaga cggggtctcg   1380
ctgtgttgcc caggctggtc tcgaactcct ggactcaggt gattctccca cctcggcctc   1440
tcgaagtgct gtgattacag gcgtgagcca ctgtgcctgg aacaaattgt taagtacaat   1500
gcttttcatt gtagaaaaca tctcggaaac ttttgaaata ggctgatgtt cagtgggggga   1560
ggaaggactc agtcgtatag ttgtcactaa ttttttgact tgattgacat gactcgtaaa   1620
tcatagacaa tagagatttg gttgcttggc tgagtagagt gcgtgaaaaa tacacacgta   1680
ctttttttttt tttttttttg agatggagtt tggctcttgt cacccaggct ggagtgcaat   1740
ggcgccatca tggctcactg caacctccgc ctccccgttc aagcgattct cctgcctcag   1800
tctccccagt agctgagatt acaggcgccc gccaccacgc ccagctaatt tttgtatttt   1860
tagtagagac agggtttcac catgttggcc aggctggtct ccaactcctg acaggtggtc   1920
cgcccgcctc ggcctcccaa agtgctggga ttacaggcgt gagccaccgc acccggccat   1980
atttttgtta ttaattttca aaggctttgg tgtgggacca catttcaaca tggaaggcct   2040
taaacatgtt ccacactact tcctgagaat tagacaagat ttttaacaat attgttacct   2100
agttgggaca catttgtact gacccatggg atgaaaaaaa gctgagtgct agcctagtga   2160
aaatctactt acccgaaaga aatccctctt agtctgggtg cagtggctca caccagtgct   2220
ttgggaggcc cagacgggcg gatcatgagg tcagtagttt gagaccagcc tggccaacat   2280
ggtgaaaccc cgtctctact aaaaatacaa aaaattagcc aggtgtggtg gcaggcgcct   2340
gtaatcccag gtactctgga ggctgaggca ggagaattgc ttgaacccga gaggcagagg   2400
ttgcagtgag ccgagaccgt gccactgcac ttcagcctgg gcaacagagc gagactccgt   2460
ctcaaaaaaa agaaaaggaa aaaagagtcc ctcttaatta tcagcatgtg tataggccta   2520
cagatacttc aggaatacct ttaccattat catcaacttg tatctacata gcatgtgaag   2580
attcaacaat ttagtttttt gggcgtcctc aagagtacgc acctataacc atatggccca   2640
attgttaatc tcctatacag tccattctgg gaatgtttgg gcttactgtg ccatttttcc   2700
gttcactgcc ttcccctctg caatatacct ttaacccttg ctaggtcctg ggtttggaga   2760
gccagagaac caactttggc cctaaagaag ctgtgtaggt agcaatatct gcctacgaag   2820
ggccttgcaa ccatttcctc ttggaacctt ggtttcctct ttctgagtag tcactttgag   2880
taccctttat taagttagaa tgtaaaaaca gtttctcact gatatatctg cagtgcctga   2940
gagagggcct ggcacagagt aagtactcaa taaatatttg aatggggccg ggcgtggtga   3000
gacctgtctc tacaagaatg aacaaaatta gctgggcgtg ttagcacatg cctgtagact   3060
tgggaggctg aggtgggagg attgcatgag tctgggaggt cgaggctgta gtgagccatg   3120
atcgcaccac tgcactccag cctaggggac agagcaagat cctgtctcaa aagaaaaaaa   3180
tgtatatatt tgaatggata aagagatggc tttgagtttc tgagatatat atggtgctgt   3240
ttatctaaag taaacaagtt ttctgtaaat attttaaggc tttgcaggcc agctgtagtc   3300
tctgtcacac attcttattt gtgcatgttt ttcccaacca tgtaaaaatg taaagtgcat   3360
tcttagctac tggggcaggt tgaatttggc ccatgggcta gagtttgcca accccctaact   3420
```

-continued

```
taaacctttg tactaacttt atgaccacta ctggattttt gttgttgttt gttttagttc   3480
tggtgcctgc tttgtttttt tttttttttt taatcctctt gctgatgttt cttggtgcag   3540
ttactgtgcc atttgtattg gtgcttttaa tgtaatgcaa actggtaata atatctaaac   3600
ttgctggggt tgtacataaa attattgaaa agattgaaaa gatgctgagc attgactctg   3660
tggcattcat tatgcccttt tgtgattgct ggattttagc catctttagg acatttgagc   3720
tttaggagaa gccaaattct gtataaatga cttgaagtgc taatagcaca ggttttgaaa   3780
cctctgcctg ggtttgagtc tcagctctgc cttttactac ctgtgtgatc ctgagcaagt   3840
tacttagtat ccctgtcctc tagtttcctc ctctgtagtg tggggataat aacatagaca   3900
taacctgaga gttagagtgt agagaaggct ccctggcaga tagtgctgta gaagtactgg   3960
ccattgccat tactcaggtg cttgtgtttg ctgaacctca tagtaagggc tcggagagca   4020
ctaagaggag gtgagaaatg ctgctagatt gacagcttgt ccccagatag cccattcccg   4080
agagcacctt aggtttatac ctgatttgtg ttgtagttag tagtgtctct ggtaatttga   4140
actagtttca ggttggtctt gaaaacctgg ggaggttggg ggtaaatgat ttggtagcag   4200
ttctcttttg tgattttata cattatcttt gtagaactgc agtttgctaa ttctctgagc   4260
ccaacacaat gaagtctggg cctaaaatca tagaatttct tttatttttt tttttgtttt   4320
taatttattt attccctccc tccctccttt cttcctttct tccttttctt tctttctttc   4380
cttccttcct tccttctttc ttttctttct ttcttttctt tctttggagt ctcactctgt   4440
caccaggctg gagtgcagtg gcacgaactt tcttcagagt ctcactttgt caccaggctg   4500
gagtgcagtg gcgcgaactc agctcactgc aacctccgtc tcctgagttc aagagattct   4560
cctgcctcag cctcccgagt agctgggact ataggcatgt gccaccatgc ccagctaatt   4620
ttcttatttt tagtagagac gaggtttcac catgttggcc aggatggtct tgatctcttg   4680
acctcgtgat ccacctgcct cagcctccca aagtgcgggg attacaggcg tgagctacca   4740
cgcccagcct atttttttatt ttttgaggca gagtctcact ctgtcaccca ggctggagtg   4800
cagtggtgca atctcagctc actgcaacct ccgcctcctg ggttcaggtg attctcctgc   4860
cttagcctcc tgagcacctg ggactacagg cgcctgccac cacacctggc taattcttat   4920
atttttagta gaggcggggt ttcaccatgt tggccaggct ggtctcgaac tcctgatctc   4980
aagtgatcaa cctgccttgg cctcccaaag tgctggaatt acagccatga gccaccatgc   5040
ccagccaaat catgagattt caataccgct gaactttgat tatggcaaag tgaacttctg   5100
ctttgattaa agcttgatga gagaggtggc tggggatagt ttgagataag ggcaaggcag   5160
gaaaatgcat aatcttacgt gggctcattg tcattgtaca attcttttgg tccatgtgga   5220
atttgatccg tcctatgact taagttatgt ttatttttgt ttttattttt atttattttg   5280
tgtctttttg agagacatga tgttgctctg tcacctgggc cagaatacag tggcacaatc   5340
ttagctccgt gtagccttga actcctgggc tcaagtgatc ctcccacctc agcccctcaa   5400
acagttgaga ttatagtatg aaccactgtg cctagcctta agtgattttt aaatttgtac   5460
tgaacagttt gtcctttcct tccattaaat catattagaa gtacagaact tgatatttcc   5520
tgtagcaata cagtttttct ttgatgaagt ttgatttcaa gtacttattt ttcataattt   5580
aaagctattt tttatagaga gaattttaat caaatatttg gatgtcacta ttgctatata   5640
tggtattaag tatggtgacc atagtttgta aactccaaac tgacagcaag acaggaaatt   5700
tgtgttagca aaggcttttt tcttactgtt tgaatttttt aaaaattaga tacaatacag   5760
agaggagcac acaaatcatt aagagtacag ctcagcgaat tttcacacag tgaacatgtg   5820
```

-continued

```
taaacagcaa gtaacaaaag atttacctgc atcctataac ctcccattat tcccttttct   5880
aggtactgtc tctccactgc attcccacca aatataacca ctatgctgaa ttctgacatc   5940
ataaatgagt tttgcctgat tttgagcttt tgtgactgga agtgtacagt gtatataccc   6000
tttcgattct gtcctcttta gtttaccatt gtttgagaaa tttatccata ctgttccaga   6060
attaactact gttaattatt gttaattaac tactgttgta gttaattcat cctcattgtt   6120
atctagtatt cttttgtgag taaacacaat ttccattcta ctgtgatccc agctatccat   6180
ttgggtcgtt tccagtttgg ggtccattac aaatagtaat gctatctgta atgctatttt   6240
gtattactac aaatagtaat gctatttgtg gcacaaaaat actgcttttg tgaacattct   6300
tatacatgtc ttttgatgaa tgtatgtttg cattgctgtt gtttacatta tgtacctagt   6360
aatggaattg ctagatcata ggagatgtat atattaagct ttagtggatg cattacataa   6420
ttattagtta ttattggtta taccaattta tcctctcatc agtagtatac aacagtttct   6480
gtatctctaa tctccaacat tttagccatt ttagagtttg tgtactaaca cattgtggtt   6540
ttaatttaca tttccctgat gactaataaa gttgagtacc tcttttgtgt tctttatagc   6600
catttgactg tcttgtgaag tgcttgtttg tcttgcctat ttttcttttc tttctttctt   6660
tttcttcctt ccttcctttc tttctttctt ctttctttcc ttccttcttt tctttctttc   6720
tgtctttctt tcttgtcttt cttgtctttc tgtctttctt ggtcttgccc tgtcacccat   6780
gctggagtgc agtggtgcag tctcagctta ctgtagcctc gaccttttttg gggctcaagt   6840
tatcctcctt tctcagcctc ccaagaagct ggactacaag cacgcaccac catgctcagt   6900
taattttttta tttttgtag aaatggggtt tcaccatgtt gtccaggctg gtctcaaact   6960
tctgggctca agtaatcctc ctgccttggc ctcccaaaat gctgggatta caggcatgag   7020
ccaccgcagc cagccttggc tatttttcaa aaggatataa gtagaacatc tgtatatccc   7080
ttcaatttgc atattattca gtaagagttg cactctggta gtagaaatat ataaggagga   7140
gaaagaagtg gaaacaaaaa gtctattctc atgagaagac ttgggggata gtgttctctc   7200
tagctccaag ctacttattc cttacgaaaa gttgaagata aacttatctc agactgaggc   7260
tgtctcaatg ttgtcttcct attccattat acacatataa cccatatttt tttcaccagc   7320
tgaattttgc tcctagaaaa ttgattcatc aggaaaaata tccgtcttgc aaggtggttc   7380
tctttagagt ctgctgtgtg acatagctca ggacaaattg tgtgatgtca gataggttgg   7440
gttaaggaat agaccttatt ggggaaagag agaacttgga gggccaaggt tagcaggaga   7500
aggaaatgtt ctctcatctg ccgtcaattc agggaggggc aaacctggtg tctgtgttca   7560
cagggaggga tccatccatc tgtgattctc ccttcttatc aggtagcatg ggaaagctac   7620
actgttgcgg ggaggagggt cacacgcagg ctacttagta ccaggcaccc tggacttgga   7680
ttcaggttgc cagttgtgtg agaaactgcc cagcacctga aggccctgaa cccatgagaa   7740
gttgtaccta cctcccatga ggaggaatcc tgtcatccca tgggagctga gcttgggtgc   7800
agtccctctt gctggcttgt ccaggagtga gctccagggt tgtttgggac agttctgctc   7860
attgctttac actgtgtata cattatctgt agagttccat gaagagaact tcagcactgt   7920
aactgcaagt tttaacatgg aacagaattt ttctcacctg tattaattct taagatttga   7980
agttctatca acaagcattt agattgtgtg gagatttttt tatttttatt tttggagaca   8040
gagtcttgct ctgttaccca gactggagtg gcagtggcat ggtcttggct cactgcaggc   8100
tctacttcct gggttcaagc gattctcatg cctcagtgtc ctgattagct aggactacag   8160
```

gtacacacca ccatgctggc taatttttgt atttttagta gagacgaggt ttcaccgtat 8220
tggtcaggct ggtctcgaac tcccagcctc aagcagtcca cccacctcgg cctcccaaac 8280
tgctgggatt acaggtgtga gccaccatgc ttgactgaca tcatcatgtt aaaagaataa 8340
atgttctagg gagctgggca cagtgtcatg tttctgtagt tctagctgct cgggaggctg 8400
aggcaggaag atcccttgag ccctggagtt caagtccagc ctgggcaaca tagtgagatc 8460
tcttttttta aataaataaa taactgttct agggactaaa atttcctttc accattagta 8520
atttactgta gaatctccaa gaatgaactt attttaggta ctgaaaatga gggagactaa 8580
atgttttata cagtagtttt tagtaaaata tgagatttga tgcatttgat agatgatgtt 8640
tgtttaaaat aattcttaaa tttttgatca tgtaattata gtttcattaa tggtagattt 8700
gtaaaataaa tgttaccaaa tgaaaatgca tgtacctatg ttaattatcc ttatctaaag 8760
ctgaaagttc agttcaacta tgttaaaaca tagtaggggc ctggcagggt ggctcttgcc 8820
tgtaatccca gaacttaggg aggccaaggt gggcagatca cgaggtcagg agatcgagac 8880
catcctggct aacattgtga aaccgtatcg ctactaaaaa tacaaaaaat tagccgggca 8940
tggcggtggg cacctgtagt cgcagctact tggtaggctg aggcaggaga atggcgtgaa 9000
ctcaggaggc agagcttaca gtgagccgag atcatgccac tgcactccag gctgggtgac 9060
agagcaagac tccatctcaa aaaaaaaaaa aaagttggcc aggtgtggcg gctcacacct 9120
gtaatcccag cacttttgga ggccgaggca ggcggatcac aagatcagga gtttgagacc 9180
agcctggcta acagagtgaa accctgtata tactaaaaat acaaaaatta gccaggcatg 9240
gtggtgcatg cctgtagtcc cagctacttg agaggctgag gcaggagaat cacttgaacc 9300
cgggaggcgg aggttgtggt aagctgagat tgctccactg cactccagcc tggacaacag 9360
agcaagactc tgtctcaaaa aaaaaaaaaa ttaatgatta aattatttag gggagccggg 9420
cgcagtggct cacgcctgta atcccagcac tttgggaggc caaggcgggc ggatcacgag 9480
gtcaggagat caagaccatc ctggctaaca caggatgaaa ccccgtctct actaaaaata 9540
caaaaattta gccgggcgtg gtggcgggtg cctgtagtac cagctactcg ggaggctgag 9600
gcaggagaat ggcatgaacc cgggtggcgg agcttgcagt gagccaagat agcgccactg 9660
cactccggcc tgggtgaaag agtgagactc cgtctcaaaa aaaaaaaaaa attatttagg 9720
ggaagatact atacaattct gtttaacaag tcacatttta atttttctt ttggaaatat 9780
tagcaagaag gctcactttg tgctcaacat tgcctgaata acttattgca aggagaatat 9840
tttagccctg tggaattatc ctcaattgca catcagctgg atgaggagga gaggatgaga 9900
atggcagaag gaggagttac tagtgaagat tatcgcacgt ttttacaggt actgatttta 9960
aactcactaa gtcacatttc tttttttttt tttttttgga gacggagtct cgccctgttg 10020
cccatgctgg agtgcaatgg cgcgatctcg gctcactgca acctctgcct cccgggttca 10080
agcgattctc ctgcctcagc ctcccaagta gctgggatta caggcacacg gcactatgcc 10140
cggctaattt tttgtatctt tgttagagat ggggtttcac catgttggtc aggttggtct 10200
caaactcctg accttatgat ccacctgtct tggcctccca aagtgctggg attataggtg 10260
tgagccacca cacccggctt acatttcttt taaaaatgtg gataccattt agaaaaggat 10320
gggccattct tcctataggg atctgactgg tgaattataa ctgtgctgtt aactttggaa 10380
atgggaatgc acaagatatt gttttaaata tgcacgctaa tgacagtttg tatccttctt 10440
tccccacccc caccccttgct tcaactacct gtcaaaatta acagcagcct tctggaaata 10500
tggatgacag tggtttttc tctattcagg taagtagtca caagcatgta ctatgtgttg 10560

-continued

```
cttacatccc aggcaccgtt tcacagcctt tcaatagtca ctgtaacaag gcgaccttcg  10620
gaagttcttc tgtctacaga gtatagatta tactctagag tactagattt tttttttctt  10680
gagacagagt ctcgttctgt cacctaggct ggagtgcagt ggcgtgatct tggctcactg  10740
tagcctctgc ctcccgggtt caagcgatcc tcctgcctca gcctcccaag tagctgggat  10800
tacaggcacc cgccaccaca ccagttaata tttgtatttt tagtagagat agtggggttt  10860
caccgtgttg gccagtctgg tctccaactc ctgacctcag cctcccaaag tgctgggatt  10920
acaggtgtga gccactgcac ctggccaact agagtactag atttttatat agataaacat  10980
gaaaggattg tagaatcttc atattagagt ggggcattta aaaattcctt cttgagaaag  11040
attaatttgc atctggatgc taataataac cttaattctg gccgggcgcg gtggctcaca  11100
cctgtaatcc cagcactttg gggaggccga ggtgggcgga tcacgaggtc aggagattga  11160
gaccatcctg gctaacatgg tgaaaccccg tctctactaa aaatacaaaa attagctgga  11220
cgtggtgaca cgtgcctgta atcccagcta ctcgggaggc tgaggcagga gaatcgcttg  11280
aaccagggag tcgtaggttg cagtgagcca agatcgcgcc actgcactct agcctggtga  11340
cagagcgaga ctccatctca aagaaaaaaa gaaatcctta attctaataa gtcacaatgt  11400
ctcaaactta ccatctgttg ggtaaatttg agaaaatgca ataccttgct accatccttt  11460
taaatcagcc taccagactg gatttcctta ttatggtttg tggcttttga tttttttttt  11520
ttaatgtata gctctctttg aattctttgg tggttatata tatatgtact cgcaagattc  11580
ttttatctgt gggtctttca ttctttttct aacactgtga gttgtatcca gagtactttc  11640
ggaacctctc ctgagcgacc tatctctgca gatatctttg tttatgtttc ccttgtactg  11700
ccctcctgga ctcttcctca tccaccagca tttccatcta gtgctttacc gtgccactgc  11760
taacaggtaa tggctactgc agggctgaaa tcagaggcca gagtaggccc agcacttggc  11820
gtttcctatt tgtgccttgc tgctcttggt gcctgttcat gtgtgcccac taccttgcac  11880
tcaatttctg tctttgctgg tacctggctc acttgcttct ttgttggcta ccttggaggg  11940
cagatagtga attttcagaa atttcccttt ttttgtcaga cagattgaaa taaacaggtt  12000
tgcattttgt tttttctaca agcggcaagc ccatgaccct agaagtctga catctatgga  12060
accttcagtt taaatgccca gggagaactt attttggtag atatgatttc tgacattgca  12120
ggtagcaagt tgaatataat tttctaaag tagcacccac agcagccaaa ttatcagatg  12180
tatatagtag actagtttta agaaaagcac ttatgggtag aatatacatc tggatttttg  12240
aggcagtttt atttaggaat tgtgtggttt tctggaacat ctcagagacc tggtatgaaa  12300
agcactcttc taatatatat gtgttttttt ttatggattt agtgatatat ctatacacac  12360
acacttttta aaacctatag ccggctgggc gtggtggctc atgcctgtaa tcccagtact  12420
ttgggaggcc caggcgggtg gatcacaagg tcaggagatt gagaccagcc tggccaacaa  12480
ggtgaaaccc tgtctctact aaaaatacaa aaatagctgg gtgtggtggc gtgtgcttgt  12540
aatcccagct actcgggagc ctcaggagga gaatcgcttg aacctgggag gcggaggttg  12600
cagcgagccg agatcgtgcc actatactcc agcctgggcg acagagcaag actctgtcac  12660
aaaaaaaaaa aaaaaaacct atagccttct agagaaattt atatatgaag tacacaacta  12720
acatagctac acttcctaaa tttggaatgg agtggtttag cttatgaaaa gttgctattt  12780
ttcttaacag gttataagca atgccttgaa agtttggggt ttagaactaa tcctgttcaa  12840
cagtccagag tatcagaggc tcaggatcga tcctatgtaa gattctgttt tgcatttcat  12900
```

-continued acatttcttt tcccaaattt gatttttaaa gttgtaattt cttaaagaag agaaatacat 12960
tttgaatact tttgttttga tgttccctgt ttcattcact cagactttcc tatttcacct 13020
ttgtgatgtc catgagcatc tgccctgtag ccttcctggc accccagtgt ctgtggcagc 13080
acagagctga ccccataagt ggtgcatgag gccatcttgt ggcacagcat cactaagctg 13140
ctgcagagac gttcatatgg ttgtgtgatc ttttaaaaac atcagtgaca cttaactata 13200
aatataatct taaattatca caaattttat ataatatttg ccagtagaca acataaatat 13260
gaattcaata tttcaagtta atattgtctg ttttcttttt tagaaatgaa agatcattta 13320
tatgcaatta taaggaacac tggtttacag ttagaaaatt aggaaaacag gtaacatttc 13380
ttacccttcc ttgtcttttt ttcttatatt gtaccccatt taaaactaaa atgtgggcca 13440
ggtgtggtgg ctcatgccaa cagtttggga ggctgaggtg gggggatcac ttgaagccag 13500
gagtttgaga ccagcctggg caacaaaggg aggtcctgtc tcttaaaaaa aaaataaaaa 13560
taaaaataaa aataaataaa aaaaaaaaca aagagccagg catggtggct cacatctgta 13620
attccagctt acttggaagg ctgagtcaga aggatcactt gagctcagga gtttgaggct 13680
gcagtgaact atgattttgt cactgtaccc cagcctgggt gacagagtaa gactgttcta 13740
taaaacataa aaataaaaaa aatatattta aaaattaaaa aaaaaaaagg attgctgact 13800
ttaaaattag gaaactgacc agtaatgtgt gtgtgtgtag catggtttat ccttcttgat 13860
agatagaaat tgtcatttta aaagataata tcagttttcc ttataaattt atttgtgaca 13920
agtatatgca atttaactat atcataagaa aaattctata ttaaagataa tacaaatgtg 13980
gttactttta agtgggtttt tatgtgatga ctatgttctg tcagttaatt attacattta 14040
tagatttgta tttagcatag tgctgtcaca aagcctgaaa tagtgtcaag catgaataaa 14100
gcattcaatt atgtttgctt tagtgtaaga ttattcatta tgattccaaa agccatgtaa 14160
tacgtacgtc tacagaaaat cacttctatt ttttaaataa aacatgaaat atgtcttgag 14220
caagctattt taagaaacaa tcatttaacg tccttgttat tagaattttg aatctttgaa 14280
agagggttat tgaaaaccag ctaggacagt aaaaaagaat aaactagtga tacatgcagc 14340
aatatggatg aatctcaaaa taattatgct gaaagaataa cccacaaaca aaatactacc 14400
tgctgtatgg tatcatttat taaaagtcta gaaaagtgca gattcatctg tagtgatgga 14460
aagcagattg accagcggtt gcctggggac gagaaggcta tggaggagtg agaggggagg 14520
gttacagaga ggcacgggaa acatggcaat gaggaatgtg ttcactatct tggttgtagt 14580
aatggtttca tgggagtaca gtatacaaat gtgaaaacat ttcagaggcc agatgcagtg 14640
gctcatgcct gtaatcccag cacttttgga ggccaaggca ggaggattgc ttgagctcaa 14700
ggagttcagg accagcctgg gcaatggcac aagaccccat ctctaaaaaa aaaatgaaag 14760
aaaaaaaaat tggctaggcg tggtgatgca tggccgtagt cccaggtgct agggaggctg 14820
aggagggagc acagaggtca agcctgcagt gaatcatgat cgtgctactg cactccagct 14880
tgggtgacag aaggagatcc tgtctcaaaa aaaaagtttc aaattataca ctttaaatat 14940
gtgcagttta ttatatgtca cttatacccc aataaatctg ttttttttaa aatgtaaata 15000
caagccaaaa aaggtataag tcaagaaaat atattgaatt aaatctgtaa gagataattc 15060
aaaaacaaaa accctattgt tatcttttaa gtcacccaaa tcaaatttgg gaaaagtcac 15120
ctacttagct tcatcctaag ttggttcttt ctttctttct ttccttcttt tgagacggat 15180
tcttgctcta tcgcccaggc tggattgcag tggcgggatc ttggctccct gcaacctccg 15240
ccacctgggt tcaagcaatt ctcttgtctc agcctcccaa atagctgtgt ctacagccac 15300

-continued

```
gcaccaccac acccagctaa tttttgtatt tttagtagag acggggtttc gccatgttgg  15360
tcaggctggt cttgaactcc tgacctcagg tgatccgtcc gtctctgcct ctcaaagtgc  15420
tggggttaca ggcgtgagcc accatgccga gccctaagtt ggttctttct taaagttctt  15480
cctgaggagc caagagcaag ttaaggagat gtaacctaga agcttacagt ggaggctagc  15540
tgggtgcagt ggttcacgcc tgtaatccca gcactttagg aggctgaggc agggagatca  15600
ctgaggccag gagcttgaga gcagcttggc ccaacacagt gacaccttgt ctctacaaaa  15660
aaaaaaaaaa aaaaaggcag cttacagcag tagaggctga tgcgagtggg aatcacctct  15720
aggtaaaaac cagtgtagcg tactgctgag attatttaac ctctgggttt tatttatgtg  15780
tttttaaaaa ttatgatcca gtattttta cttttttttg tataaagtaa gcactgaatt  15840
tttaaggttg tattaatttg caaataaatg tctatcttat tattttgaga gatttaaaaa  15900
attttagttc ttcaaaattg cattttcaca ttttgaatta cgttatcttt gacaaataca  15960
gaagatgtca aattttggtt tattttcttt ggttctaatt tatattttg tttaaaacta  16020
tatttttcac tatagactct ttctgtctct cgaggtccct gtataatgaa aaagaaggct  16080
ggaaaaagta ttaacattgt caaaatccag gaaaagtagt tggtcatgat attgatcgtt  16140
aactttagaa actttttgta tcttgtgggt taaattagga ttactatgtg gtagtgataa  16200
atgatgttaa ttagggccga gtgcagtggc taacacctgt aattccagca tgtagggagg  16260
ctgaggtggg aggatgtctt gaatccagga gtttgagacc agcctgtaca acatagtgta  16320
agacccctt c tccacacaaa aaaattagaa aatttgtcaa gcatcttggt gcacacctgt  16380
agtcccagct gcttgggagg atgaagcgag agaatcactt aagcccaggt gttcgaggct  16440
gcagtgagct atgattgcac cactgcactc cagactagat gaccatctct tttaaaaaaa  16500
tgtgtttata tgttatatgt gatagtgctt tttaaaaaca tttttaaatt atagagacag  16560
ggtctcacta tgttacagcc caggctggtc tcaaattcct gggctcaagc aatcctccca  16620
ccttagctaa cctcccaaag tgctcggatt ataggcatga gctgcatgcc cagctaattt  16680
agtgattttt aaaaactgag ctggtaatta taaattctct tcctggaact tctgactttc  16740
tcacaattgg aatcttttga caaaaattat cagtaatggg aaaactttgt gtagttgtca  16800
tttttcctcc catcagtgtg atagatatga ttggagttat gttggactga tattttgaaa  16860
aaagatttaa ttatagctat taataaagac atttaaacta ctgactatgc atttttattc  16920
ttttgggagg gtttaatgtt tatagtttaa agcaaactgt tgtttttaaa aaagtatcta  16980
acagggccgg gcgcggtggc tcacacctgt aatcccagca ctttgggagg cctaggcggg  17040
cggatcacaa ggtcaagaga tcaagaccat cctggctaac atggtgaaac cctgtctcta  17100
ctaaaaatac aaaaaaatag ctgggtgtgg cggcgtgcgc ctgtagtccc agctactcgg  17160
gaggctgagg caggaggatg gcatgaaccc gggaggcgga gcttgcagtg agccgagatc  17220
gcgccactgc actccagcct gggcgacaga gcaatactct gtctaaaaaa aaaaaaaaaa  17280
aaaaaaaaag agtatttagc agaggccagg tgcagtggct catgtttgta atcccagaac  17340
tttgggaggc tgaggcgggc ggatcatttg aggtcaggag tttgagacca gcctggccaa  17400
tgtggcaaat gtgctgtctc taactaaaaa tacaaaaatt agctgggtgt ggtggtgcag  17460
acctgtagtc ccagctactt gggaggctga ggcaggagaa tcacttgaac ctgggaggca  17520
gaggttgcag tgatccgaga tcatgccact gcactccagc ctgggttaca gagtgagact  17580
cttctcaaaa aaaaaaaaaa gtatttaata gtgataaatc tgcagtattc tcttgtagtt  17640
```

-continued

```
tttaagatca tattattcag tcaaagaaaa gagctcaact tgaaatattt ccagagttta  17700
aacaatctta ctaagctttg atgggttgta tctattctta acatgtgaaa cttccttatt  17760
acctataata tacactaact taaatattga caattttttt ccagtggttt aacttgaatt  17820
ctctcttgac gggtccagaa ttaatatcag atacatatct tgcacttttc ttggctcaat  17880
tacaacagga aggtaagtaa cggctgaaca ttttgtaatg ttacctttcg aagtagttaa  17940
ataaccaggc acattagatg acagtgtgat aaaactgttt ttctggcagt ggcagtgaaa  18000
caatctttag ttttgacgtg gtgataggct gtgatttggg tgacgctgtt cagttagagt  18060
tctcactgac acctggccct tcctcttctg aggatgctgc tttctttgca gcccttctaa  18120
gtaatggctt tttcttttat acatcacata tcacacggct gagaggaggg atagatgttt  18180
ttcttctttg cctcttctag gccactgttc ttccttataa actccagttt ctttgaaata  18240
catgccccta acggctgggc acggtggctc acgcctgtaa tcccagcact ttgggaggct  18300
gaggcaggcg gatcacgatg tcaggagatc gagaccatcc tggctaacac ggtgaaatcc  18360
tgtctctact aaaaataaca aaaaattagc cggggtgtgg tggcggacgc ctgtagtccg  18420
agctactcgg gaggctgagg caggagaatg gcgtgaaccc aggaggcgga gcttgcagtg  18480
agctgagatc gcgccactgc cctccagcct gggcgacaga gcgagactcc gtctcaaaaa  18540
aaaaaagaaa agaaaaaaaa aagaaataca tgcccctaga ttaaactatc ccttgtcctt  18600
ttgcactcat ccacaagtct cttttcatca gtgattttag gatctgactc gttgtctttt  18660
tctctacttc aactactttt atcattctta attatttctg tatcgtcaat caatccagta  18720
cctgcctctt agtttcaaaa tcacttactc ttgcttagct attaccagta atcataacca  18780
ctgtcaaatc tcaattgcaa gcatattact ctttaactac cacctcctat ctttaaacca  18840
tgttttgtct gttttttttat tccagccatt ctttaaaccc tactgtgggg cccaagcatt  18900
tcctttatac gcattcttcc tttcttctac tgcttatttt ctgtaatccg tcatcataat  18960
cactccattg cattcttcaa cgtgtttccc ctctctccct ccatcatact tgaatgacaa  19020
aaatctcaac cctggttaaa ccacatcttg gccttgtcca ttcctgtacc agagtagctg  19080
gacgtggcta aaaaataaca taaaacatga tgattggttt tacttttttc ttaaatgatc  19140
tatccatcca ttcacccatc catctatcaa agtgactagg cctatttctg aagcccaggc  19200
tggagtgcag cagcataatc acagctcatt gcagctccaa actcctgggc tcaagtgatt  19260
ctcttgcctt agcctgttga gtagctggga ctacaggctt gtgctaccac acctagctaa  19320
ggttttactt taaatttatt ataatcacaa aattcagatg agcctttagt gctgtctgat  19380
atttctacta tgttttctta gtgatgtacc accctccaag gtgtttataa aaaattatgt  19440
accactctcc aagaagttta taaaaaaataa tgtgccaccc tccaaggtga ctaatttcac  19500
agcttatgtc tttaaacctt taagcacttt cctctccctt acacaccttc cttgtggctt  19560
tccgttacat tctgctgaga acatagaagc aattaaaatt atgttctttc taccagcaaa  19620
tttatcaatt tgcttatatc ttcacctgtg ctttgagcct atttaaatag atgaatggtc  19680
ccctacctct aaccaaaacc agtccctcac ttgtgggctg gatcccagct cttctcacct  19740
actcaagatg ttcctgcttt catctctcca ctctcttata taatcagttc cccccccctt  19800
tttttgtaat attcctataa gcagtaaaat aagcttttta tttccattga ttaaaaataa  19860
aaatcctctc ttaattccat gaaactccag ctgcctcccc atttttattt tttccttagg  19920
attgtctcta gtgtgccttc tccttttctt gaactctgcc tcctgggttc aagcgattct  19980
cctgcctcaa cctcccgagt agctgggatt acaggcgtgc accaccatga ccggctaatt  20040
```

-continued

```
ttttttttt ttttttgaga tggagtttcc ctcttgttgc tccggctgga gtgcaatggc  20100
gtgatctcgg ctcaccgtaa cttctgcctc ctgggttcaa gcgattttct tgcctcagcc  20160
tcccgagtag ctggatttac aggcatgtgc caccatgcct ggctaatttt gtattttagt  20220
agagatggaa ggggtttctc catgtttgtt aggctggtct ccaactcctg acctcaggtg  20280
agccgcccac ctcggccccc taaagtgctg ggattacagg catgagccac tgcgcctggc  20340
cccggctaaa ttttttttt ttttttttgt atttttagta gagacagggt ttcaccatat  20400
tggccaggtt ggtctcgaat tcctggcctc gagtgatcca cctgcctcag cctcccaaag  20460
tgctgggatt acaggcgtga gtcaccttgc ctagccatct tttagtaatg gtatttggag  20520
atcacaattt gagtgctggc atgcttattg ctgctgggtt tgttatgtag ttattgtgaa  20580
ttcacattta ggaatatagg gtttttaatt ctttgatttt agatacttgt atcttttttc  20640
ttttatattt aaaaccttgg ttcctgatga tatcccttct tagaaaccct gtctaccttt  20700
ggccttcagc ccaccatgct gtggttttcc taacttgctg cctgcacttt tcagattcct  20760
ttcatggatc ttaaatatca tctgtaaata agatctatgt gtcaataatt accaaacttt  20820
tatctttagt cttgacatct accctgaaca cctagctttg actaactcct agctttggca  20880
tctccacttg gaaatccaaa aagtgtttca aactgaacat gtctatgaaa gacttatttt  20940
tttctctcta tccatgctat ccatcaggtt ttccatttcc ataagggtga ctcttgtact  21000
ctggttccta tatattatac cgacagagca gcccagagtg cttcttaacc agtgtaaggc  21060
ctgttatgtc ccaccctcac tctttgtcct tcagtggctt cccagcacac ttagaataaa  21120
atctgaagtc ttaggccggg cttggtggct catgcctgca atcccagcac tttgggagga  21180
tgagggggca gatcacttga ggtcaggagt tgatgagacc agcctggcca acatggtgaa  21240
accctgtctc taccaaaaaa tacaaaaatt aactgggtgt ggtgttgtgc acctgtagtc  21300
ccagctactc gggaggctga gataggagaa tcacttgaac ccgggaggca gaggttacag  21360
cgagccaaga tcataccact gcactccagc ctgggtgaca gaacgagact ctcaaaaaaa  21420
aattaaaaaa aaaaaatatg tgaagtcttg aataaaaccc aagatcttta ccatggcccc  21480
tgaacagggc agagtatcca ttcttcagac actcttcata gaataccatg gtgagctggc  21540
atatttatta tacaatacag aaacaatttt actggcagaa aacacattaa accgtctaaa  21600
ctctgaatac agttgtcctc ataaaaaatg ttcaacatac tattttgagg ttttccatta  21660
atagttctta taatctttgt cccattatgt gttaatccaa caaaggatat ccaataacaa  21720
acaccaaagt ttaagaaaaa tgtgctaggc gcggtggctc acacctgtaa tcccagcact  21780
ttgggaggcc gaggtgggca gatcacctga ggtcaggagt tcgagaccag cccagccaac  21840
atggtgaaac cctgcctctc ctaaaaatac aaacattaac tgggtgtggt ggtgggtgcc  21900
tgtaatccca gctactcagg aggctgaggc aggagaatcg cttgaacctc ctgggaggca  21960
gaggttgcag tgagctaata ttgcaccact gcactccagc ctgggtgaca gagtgagact  22020
ccatctcaaa ttaaaaaaaa aaaaaaatta atgatagaga aacttaaatc agttagattg  22080
ttttaggtat agcccatcct tggtttttgt gtgtagcatc tagcttgggg aaaccctgga  22140
tttctggaat catatttaga cacagtcaca ctagactaat gtaattcttt tgggatgcaa  22200
accacacgtt tgacacctta aatagctttt aggtatttgg cttcccagcc cctattttta  22260
gttacaaggg gtgtacatgt gtgggtcagg gtgggggtag ctctttccgc agatgattag  22320
ttttagccat gttactagtt attgcacaca ttatctgtgt cctcacagca gccctgtgag  22380
```

-continued

```
taagtgtatt agggttctct agagggacag aactaataag gtagatgtat atatgaaggg  22440
taatgtatta aggagtatcg actcgtatga tcacaaggtg aagtcccaca ataggctctc  22500
tgcaggctga ggaaccagga agccagtcca agtcccaaaa cctcaaaagt agggaagctg  22560
acagtgcagc cttcagtctg tggcaaaagg cctgagagcc cctggcaaac cactggtgta  22620
agttcaagag tccaaaagat gaagaacttg gagtctgatg tttgagggca ggaagcatcc  22680
agcatgggag aaagatgaag gctcagcaag tctagtactt ccacactctt atttctgcct  22740
gctttattct agctgagctg gcagctgatt agatggtgac cacccagttt gagggtgggt  22800
ctacctctcc cagttcactg gcttaaatgt taatctcctt tggcaacacc ctcgcagaca  22860
cacccagaaa caataatttg tagccttcaa tccaatcaag ttgataatat taaccatcac  22920
aggaaggtac tagtatcata tgtttaacag tagaaaccaa gacaaatgca gctaggaagt  22980
gggagaactg ggatcagatg caggcagtct gattctaaat cagttgctgt tacccactct  23040
gacaacagta agtgagtagc ctgctcagtc aagtactata ttagtagggc cctttacaga  23100
catatttatt tctcacagtc actcaatgag acggctcttc cagtcttaca atggagaaag  23160
tgaggctcag agactttaag taacttacct tagacgactt tactagtaag tataagaatc  23220
attatttgga ctaaagtctt tctgaatcct cagcttgtat ttttttccag tgttctgtgc  23280
tgccttttta tctactagtg ttttacatca attttgaatc tctttactaa ctggttaggt  23340
tgatttttgc cttttttttt taggttattc tatatttgtc gttaagggtg atctgccaga  23400
ttgcgaagct gaccaactcc tgcagatgat tagggtccaa cagatgcatc gaccaaaact  23460
tattggagaa gaattagcac aactaaaaga gcaaaggtaa aaatgaggcc tgcagtatgg  23520
aatatatggt agtatttcat tatgagaatt aaattttcat gcttagattg aatatgtggt  23580
ccttgtgttg ttggcgactc tattttggac cttatatttt agtgaagttt attagtttaa  23640
acttgaatca actctttgaa atacttaaat atattaactt agttagctgg tatggtatat  23700
tcctagcact tcgggaggct gaggcaggct gattgcttca acccaggagt tcgagaccag  23760
cctgggcaac atggcaaaac ctcatctcta caaatagtac aaaaattagc cagatgtggt  23820
ggtgtatgcc tatagtccca gctacttggg aggcagagga agaaggatca cctgaaactg  23880
gggaggtaga gactacagtg agccataatc acactaccgc actccagcct ggtcgagaga  23940
gtcagaccct gtctcaaaaa aaaaaaaaaa aagaaacgga aaaaaaaaac ttagttggat  24000
tcaaattgca acacaatcat tatattacta gagcttattt gccagaaaac attttaagtt  24060
ttgacttact taaagccttt acattacaaa tgcctttatg ttatgtctaa aatagaagat  24120
tggttgcagt tattaccagt gcttttgttc tttagagtcc ataaaacaga cctggaacga  24180
gtgttagaag caaatgatgg ctcaggaatg ttagacgaag atgaggagga tttgcagagg  24240
gctctggcac taagtcgcca agaaattgac atggaagatg aggaagcaga tctccgcagg  24300
gctattcagc taagtatgca aggtaaagac attctgatgt gtgttgtatt cattgctgaa  24360
gaattgattc caattattct tagatttcat ggaagttaat gtactcttag aggtgttttg  24420
acaattactg cagaagcaat agctatatag tgggctttcc ctttagattt cttataatgg  24480
aaatcacttt ttacaaccta tattttatta ggagtagtta tatttttact cctggttatt  24540
ttatttggtt tcaacactgt actaacacaa tagtaaattg tggttttaat ctttgtgggt  24600
atcagttgac ccttatccaa atcagctgtt acataaatat gtgccattag acactatgga  24660
agggcctgga cagggaatat aaactgattt tacaaaaacc caacatttat tggctatgca  24720
acttaaaccg taagcccact ttggtgggcc cagtttttta gtgatataaa ctatcaatag  24780
```

```
agaaaagcga aaacatatcc cctagacaat ctaggcaaag aaaaatgtta agacatagct  24840
caaagtagct taattaaaag tttgaagtgg gttttttgtt ttattttttt ctaactcata  24900
tgtatttgct tctactttct aatgaaatta tttatcagtt gatttcctta gatatctaaa  24960
taaaattgaa atttcattaa tgggaagatt atttttatcc tgaacttttc ttgcctctat  25020
gcatgcctct gagtactcca tatggtgtgc aatcccattt ttgattaata gagtcctgct  25080
ggattagcag ggacagaaat cagctttaga tttctttctt tttttttttt ctttcttttt  25140
tttttttttt tttttgagt cagagtctca ctgtcgccca gcctggagtg cagtgatctt  25200
ggctcactgc aacccctgcc tccgaggttc aagcgattct cctgcctcag cctcctgagt  25260
agctgggact acaggcgcct accaccacgc ccagctaatt ttttgtactt ttagtagaga  25320
tagggttttg cccttttggc caggctggtc ttgaactcct gacctcaggt gatccacctg  25380
ccttggcctc ccaaagtgct gggattacat gtgtgagcca ccacgcccag ccagaagagt  25440
agaatattct taaagagaaa acgttttaaa ggcttactca aatgagtata aacaaacata  25500
ttgttgcttg aattggtaaa tacagtgatt ggtttttgtt gtgttgtgtt ttgttttcag  25560
gtagttccag aaacatatct caagatatga cacagacatc aggtacaaat cttacttcag  25620
aagagcttcg gaagagacga gaagcctact ttgaaaagta aagtagttgg tacaagttaa  25680
agtagcatgt ttaatatttg ctttggctat tttgtctatt tgtaaatggt tactgcctga  25740
atcctgtgaa tatttgaatg tattttttaa aaatttacag caaataggac gggcacggtg  25800
gcttacgcct gtgatgctag cagtttggga ggccaaggcg ggcagattgc ctgaggtcag  25860
gagttcgaga ccagcctggg caacacagtg aaaccccatc tctactaaaa atacaaaaga  25920
atcagctggg catggaagcg tgcgcctgta gtcccagctg cttgggaggc tgagccagga  25980
gaattgcttg aacccgggac gtggaggttg cagtgagccg agatcgcacc actgccctcc  26040
agactgggtg acagagtgag actccgtctc caaaaatata tgtatatata tataaataaa  26100
aataaaaatt tacggcaaat aacatgaaac aaaaaaacct tgccccaata ctggataaat  26160
tttttaaact gagtgaagga aaccttataa aatttcattt attaaaagaa aaatgaaatt  26220
aggacaagac aagaagaatg ccaattgatc ctttggatgt acttcttgct tacctgatta  26280
accctgcaaa attcctctac caatcagtac gaaaaacagc tttggaggta tgggagcgca  26340
ttcccaaata gacgtggtag ttcatttagc tgctcatggc cgcttcaggc agtcctgtaa  26400
gcctgttagc atcaggggaa tggatgcaaa ccataaatct ggatcaactc ctaaaacctt  26460
accttgtgcc cagccttgta agtgcttgct aaataggaat tccaccatat gaaaatacat  26520
tcttttcaag taactatcat tcagactttt gtcccccact tttttttttt aaagaaaaat  26580
aaaaggctgg gcacggtggc ttacgtctgt aatcccacca ttttaggagg ccaaggcagg  26640
tggatcacct gaggtcagga attcaagacc agcctgacca acatggtgaa acctcatctc  26700
tactaaaaat acaaaaatta gccgggcatg gtggtgggtg cctgtaatcc cagctacttg  26760
ggaggctcag acaggagaat cgcttgaatc tgggaggcag aagttgcagt gagctgagat  26820
aacgccattg cactccagcc tgggggacaa gagcgagact tcgtctcaaa aaaaaagaga  26880
aagaaaactt catgttaaag attacaagat aaataatcag acccactgat cctaggtcag  26940
aaaacagagt catagctcaa tctgacttac tatttgctgt atttcatcca ttctgagatg  27000
cacatagttt cacatttcaa tgtctctgaa attgagaagc atcttacagt cataattgac  27060
agtatattag cagcacctat aaatattggc tcattttaca tttgatggta taatgaagaa  27120
```

-continued

```
aatatttacc ttttttctg ttttgttttt aagtcacaac tcagaagtag atgaaggaaa  27180
attctgatca gctgacatcc tcttaatgtg agatatttct agtctttatt cagtatagat  27240
taatggctaa ttatatgtta aatttcaaag tagtgcttat tagtgctttt tacttttaag  27300
tttcaaaatt aacttttta ttataataaa ctccaaattt atacaaaagt agaaaaacta  27360
gcatactcct gtttatgacc cagattcaac aaatactagc acacggccaa tcttgctttt  27420
ttttttttt tttttgaga tggagtcttg ctctgttgcc caggctggag tgcaatggca  27480
caatttctgc tcactgcaac ctctgcctcc tgagttcaag cgattctccc acttcagcct  27540
cccaagtagc tgggattaca ggtacacacc accatgcctg gctaattctt gtatttttag  27600
tagacacggg atttcaccat gtcgtccagg ctggccttaa actcctgacc tcaagtgatc  27660
cacctgcctc ggcctcccag agtgctggga ttacaggcat gagccactga gcccggccca  27720
atctcgtttt ataatactcc catctcccat tctttccact gtcccacctg caagtttgga  27780
ttattttgta acaaatctca atcatcatat tattctataa ccattttaat atgtgtctct  27840
aaaatatatt agctttattt ttaacatagt taaatgctat tgtcataaaa taataatcat  27900
aataattaat tgtaattcta tatcatcaat tatctagtta atgtaaaaaa taaatctaag  27960
gccaggcgcg gtggctcaca cctgtaatcc cagcactttg ggaggctgag gtgggcagat  28020
cacctgagat caggagttca agaccagcct gaccaacatg gagaaacccc atctctacta  28080
aaaatacaaa aaattagcca ggcgtggtgg cgcatgcttg taatcccagc tacttgagag  28140
gctgaggcag gagaatcact tgaacccggg aggcgaggtt gcggtgagcc gagatcgtgc  28200
cattgcactc tagcctgggc aaaaagagtg aaactccatc tcaaataaat aaataaataa  28260
ataataaaaa ataacttaaa tctacttaat tagaaaaact aacattctaa aaattttatt  28320
ttaagaaata tcaaaattgg ctgggcacgg tggctcacgc ctctaatccc tgcactttgg  28380
aaggctgagg tgggcggatc acctgaggtc aggagggtca ggagtacaag accagcctgg  28440
ccaacatggc gaaaccctgt ctccactaaa aatacaaaaa ttagccaggc atgatgatgg  28500
gcacctgtaa tcccagctac tcaggaggct gagacagaag aatcgcttga acccaggagg  28560
tagaggttgc agtgagctga gatcacccca ctgcactcca gcctgggtga cagagtgaaa  28620
ctccgcctca aaaaaaaaaa aaagagaaaa gaaatataga aattaaagca tacatggcca  28680
ggcgtagtgg ctcatgtctg taatcccagc actttgggag gctgaggcag gcagatcact  28740
tgaggccatg agttcaagac caacctggcc aacatggcga aagcctgtct ctactaaaaa  28800
tacaaaaaaa ttagttgggc atggtggtgc acacctgtaa tcacagctac tttggaggct  28860
gaggcaggag aatcgtttga acccagaggt ggaggttgca gtgagccgag attgtgccac  28920
tgcactctat cctgggtgac agagcgagat actgtctcaa aaagaaaaaa aaaaggctgg  28980
gcgcggtagt tcatgcctgc aatcccagca ctttgggagg ccgaggcagg cagattacga  29040
agtcaggaga tggagaccat cctggctaat acagtgaaac cccgtctcta ctaaaaaata  29100
cacaaaaatt agctgggtgt ggtggcaggc acctgtagtc ccagctactc tggaggctga  29160
ggcaggagaa tggcatgaac ccgggaggtg gagcttgcag tgagcagaga tcacaccact  29220
gcactccagt ctgggcgaca gagcgaggct ctgtctcaaa aaaaaaaaag aaagcatact  29280
ctcacctcct tcagtgactg atgttagtat tttggcacat tctttttctg tgacatatac  29340
acacttacct tgtaagtgtt gtactcattt cctatgacag taaatagtct ttgtaacagg  29400
ctgcatgata tttcataaaa tgaatggatg tggcataatt tatatgtgag ccttttgaat  29460
tctgctatta taattaatat tgcaatgaac aattcttata ttgcctctac acctcaaatg  29520
```

-continued

```
tcttatcatt tcttctagtt tttctgagga tgtcagatta ttgggttaaa ggatatgaac  29580
atttttaagg ccttggaaca gatttctaaa ttgctttcca gaataattcc catgtgatac  29640
tttcaccatg tttatttcag actttttttt tttttttttt ttgagacgaa atctcactct  29700
gtcacccagg ctggagtgta gtggcatgat ctcggctcac tgcaacctcc gcctcctgag  29760
tttaagcgat tattctgcct cagcctccca agtagctgcg gttacaggca agtgcctcca  29820
tgcctggcta atttttgtgt cttttgtaga catggggttt caccatgttg cccaggctgg  29880
tttcgaactc ctgagctcag gcaatctgcc tacctcggcc tcccaaagtt ctgggattac  29940
aggcgtgcac caccgcgccc agccatcaga gtctttttg tcaaaataaa atggtctaaa  30000
gacatacatc atagagaaac tataatacaa aatttacagg tatatctaag aaaagaaaag  30060
tatatttaaa gcataaaaat aaactgctct tttacttaaa atttttaaa aactggatta  30120
aaaatatgaa acttccaaca aattgagctt tttttttttt ttttttcttt tttgagacga  30180
ggtctcgctt ttgtcaccca gtctggagtg cagtggcgcg atctcggctc actgcaacct  30240
ccacctccct ggttcaagca attcccctgc ctcagcctcc caagtagctg ggattacagg  30300
cgcatgccac cacgtcgggc taattttttt gtatttttag tagagagggg gtttcaccat  30360
gttggccaga ctggtctcga actcctgatc tcaggcaatc tgccagcctg ggtctcccaa  30420
catgctggga ttacaggcat gagccactgc actcggcctg aactttttat agtagtaacg  30480
ataattcagt aatgtccaat aatgactaag taagttataa caagtacaat gtcagcaata  30540
actagtgctt tttagtaaac agggtcaggc aaccttgtac ccttttaaaa atgttcgaat  30600
atcgatatac ctccttccta cttggtggag gattgattga ggaggaaagt gtgcagtgat  30660
ggttaccagc ttcagcctct tggcttgact ttgcaaatac tggtgagaat ttggaaagag  30720
cttgagaata tcttacatag tcacatgttg ctgagaagag ttaagaacta acttcttgat  30780
gttcattttt aacaatggct tgcattcaaa accttgtaga gctcattagt aggagctaag  30840
aagctaatat ttgcctttca ctaaaattcc tgattactta gcctaggtag ttcgttgtct  30900
ctctaggttc tgtctttggg agcttgggtc taaggttatc aagctaactc tttcttccct  30960
ctcacccttc ccaaattgac cctggtgctg atttgttatt catacgattt tctagttttt  31020
cttttccctt tttgagtatt tgaagcttca tactgaatat agtaatcata gtattcatgc  31080
ataaagaaaa tcataaagta attgcataaa tgcataaagt aatcatagtt ttcatgcatt  31140
aaaaaaacta gttttggctg ggcgctatgg ctcacgcttg taatcccagc actttcggag  31200
gccaaggcag gcgaatcatc tgaggtcagg agttcgagac tagcctggcc aacatggcga  31260
aacctcttct ctactaaaaa tacaaaaaaa ttagccgagt atggtggcgg gcgcctgtaa  31320
tcctagctat ttggcaggct gaggcaggag aatcacttga acctgggagg cagaggttgc  31380
agtgagccga ggttgtgcca ttgcactaca gcctaggcga caagagcaag actccatctc  31440
aaaaaaaaaa aaaaaaaaaa aaaaactccc tattacagat tcataattta tgagtcatta  31500
aataatattt tcaagccatg acatttttttc cagcagtagt ctctaaatct gttttaccat  31560
cataaaaccc caagcaaaac tctactacat cagctgtgtc actgtaaaac ctgccttaac  31620
tcacagaagc atgaaattaa gcaatgtgtg tgaaactatt ttataaactg taaagtattc  31680
catacataca tgttggcagt tattaatgtc ttctctaggt gtggctttga aatggatgca  31740
gatgctttct gttacaaaaa acataagttg caaatgttct ataacaagga gagacacaaa  31800
tatcttcatg gacatggatt gctatgagtg tttgattgcc taatacttga gccaccactt  31860
```

cagtgatatg gtataattta tcaaacagtg ttgagaaaca gaaactactg gggatgtttt 31920
aaagaggaaa atacttaata tagaaattag gggtttacat aatcttaaga aaggatgaag 31980
gtgcagctct tagccaggcc tccacagtac cacaaaccaa cttgcaggaa gagctgtaac 32040
cactgcccca gttgggacaa tgggtaatga ggatattaaa tttaagaaca tactgctata 32100
gcaatgatcc ttggcataga aagctgccac cacaattgcc tagagatggg aacatgaagt 32160
ctggccccca ttgcaacagc agtgaagcag aattttggga ctggcatctc ccaaatggct 32220
ttgcttgcca ccagagaaca accaaagtgg agggagatgg ctaggcctca tttctgccta 32280
ttttatttta tttttgaga cggagtcttg tctgtcgccc aggctggagt gcagtagtgt 32340
gatctcggct cactgcagcc tccgcctccc agcttcaaac aattctcctg cctcagcctc 32400
ctgagtagct gggattacag gcacccgcca ctgtgcccag ccaattttct tatttttagt 32460
agaggtgggg ttttgccacg ttggccaggc tggtcttgaa ctcctgacct caggtgatct 32520
gcccgcctca gcctcccaaa gtgttgtgat tacaggtatg agccaccatg cctggcccat 32580
ttctcccttt tttttttttt tttttttttg aggtggagtc tcactctgtt gcccagactg 32640
gagtgcagtg gtgcaatctt ggcgcattgc aacctctgcc tcccagtttc aagcaattct 32700
tctgcttcag cctcctgagt agctgggact acaggtgtgt agcaccacac ctggctaatt 32760
tttgtttttg ttttgttttt tttgagacag agtctcactc tgtcacccag gctggagtgt 32820
agtggcatga tctgggctca ctacaacctc cgcctcccgg gttcaagcaa ttctcctgcc 32880
tcagcctcca gagtagctgg gattacaggt gtgcgccaac acacctggct aattttttttg 32940 tatttttaat agagatgggg tttcaccatg ttggccaggc tggtctcgaa ctcctgacct 33000
cgtgatccgc ccgcctcggc ctcccaaagt gctgggatta caggcatgag ccaccgtgcc 33060
cagacaaggt ttgtattttt agtagagaca gttttgccat gttggccagg ctggtcttga 33120
actcctcacc tcaggtgatc cgcctgcctt ggcctcccaa agtgctggga ttacaggcgc 33180
aagccactgt gcctgacccg tttctgcttt ttaaagctca tgtgagcact taatttgtaa 33240
ccagaatcct acttgtaaaa taatctaaga catgtagctt ttagctttgt aacctctata 33300
atattgatgg cacagtggga gtggatgctg agtaccactt gaacatgttc cacctcagtg 33360
tcttcacagc tggaaggtgt ctacattgtt tcaaggtgga caattgattt acttctcatt 33420
tttcataaac taaaagtaga ataaaggcta ttcctctaaa attgctatct cacctgtcac 33480
tcccttgcat tctcacatac cttcttgagt ggaggggcag agggcatgga gtgatagcag 33540
atgtgccagg aattctccat aactcagtcc gtccctcttg tgctatgttg cagcatcagg 33600
atttgctaat gggaggatac tgcccttacg tgcatcatta gccatgcaca ctaaggtctt 33660
acacctacac acaggtcagt attctggctc agagaccaac agggagaaat tgcagttctc 33720
attagttgaa ctttctttat tgttcacagt tttaaaacac aaaattgaga ggaactctat 33780
aaaaaatgtg ccattctatt aataattgtt gctggtaatt taaaaatcct tgttcctttt 33840
caaattctta tataccttttt ttttttaaac acttgatctt agccaaaaga ccgagaagca 33900
atcttttttt tttttttttt ttttttttaac ctatagcttc tcactgagat tgtcagctgt 33960
ttgtaagttt tggtttttgg ttttctgtgt ttgtatttac atatatgaaa tacagattga 34020
gtatccctta tccaaaatgc ttaagactgg aagtgtttta gatttggggt tttttaggat 34080
ttgtgaatat ttgcactata cttaccagtt aagcattcca aatccaaaat ttcaaatctg 34140
aagtgttcca ctgagcacct cttttgagta tcatgttggt gctcaaaaag tttctgattt 34200
tggagcattt ggatttctga ttctcggatt taggatgctt gacctgtaat ttcagattta 34260

-continued

```
cataaaagca gaaatagtac acagagctcc ttatatcctt cacccagatt ccccaattat  34320
tggcctttct gaaccatttg ggaataatat gcagatatga ttttccatta tgtctcagtt  34380
gttcagtgta tattttctaa gtacaagaat atattcctac atatttacat gataaccgtc  34440
atgtttaaac attttaaaat ggggatttgt attacattgt ttctcttttt gaaaaaatta  34500
cagaggagct taatgcaatc agtattactt aaaatctgat aatgtgtgtt aaatagtagt  34560
tttcatttat ttcatttatc aggtgttcag tgaatgctta ctatgtaaca gcacagttat  34620
cagcactggg gaaatagatg agtaagataa gatttgcact ttcattagct tacatgccat  34680
aaagagggaa ataaagagaa caccagatga tgataagttt atgctgagaa ttaaaatgaa  34740
gtgatgaaat aatgggaatg tcaggtggct acttttggtg ggatggtcag gaaaggcatc  34800
tctggggaga taaattttaa gctcagacct gagtgaaaag aatgagccag ccatggaaac  34860
attatgttaa ctcacatggt agtttgaaat gctttatctg atcaaaggta cttatttttg  34920
gtgactttca acaatattaa gggtctataa accaacactc atttgcataa gaataactac  34980
cagtgaatct ttttgtatga taggtttttt gtttgttgtt tttttgagac agagtctcgc  35040
tctgtcgccc aggctggagt gcagtggcgc gatcttggct cactgcaacc tctacctccc  35100
cggttcaagt gattctcctg cctcagcctc ccaaagtagc tgggattaca ggtgcctgcc  35160
accacgcctg gctaattttt gtatttttag tagagatggg gtttcaccgt gttgtccagg  35220
ctcgtgtcaa acttctgacc tcaagccatc cacccgcctc ggcctcccaa agtgctggga  35280
ttacaggtgt gagccaccac tcctggccat gataggttat tttgtgatga aaatacctac  35340
ctcttaattt gtctgataaa tttaaatttt atgtctagat ttcctaagat cagcacttcc  35400
atattttaaa gtaatctgta tcagactaac tgctcttgca ttcttttaat accagtgact  35460
actttgattc gtgaaacaat gtattttcct tatgaatagt ttttctcatg gtgtatttat  35520
tcttttaagt tttgtttttt aaatatactt cacttttgaa tgtttcagac agcagcaaaa  35580
gcagcaacag cagcagcagc agcagcagca gggggaccta tcaggacaga gttcacatcc  35640
atgtgaaagg ccagccacca gttcaggagc acttgggagt gatctaggta aggcctgctc  35700
accattcatc atgttcgcta ccttcacact ttatctgaca tacgagctcc atgtgatttt  35760
tgctttacat tattcttcat tccctcttta atcatattaa gaatcttaag taaatttgta  35820
atctactaaa tttccctgga ttaaggagca gttaccaaaa gaaaaaaaaa aaaaaaagct  35880
agatgtggtg gctcacatct gtaatcccag cactttggga aaccaaggca ggagaggatt  35940
gctagaacat ttaatgaata ctttaacata ataatttaaa cttcacagta atttgtacag  36000
tctccaaaaa ttccttagac atcatggata tttttctttt tttgagatgg agtcttgctc  36060
tgtcacccag gctggagtgc agtgtcgcga tctcggctca ctgcaagctc tgcttcctgg  36120
gttcatggca ttctcctgcc tcagcctcct gagtagctgg gactacaggc gcccgccaca  36180
tcgcctggct aattttttgt atttttagta gagacagggt ttcaccatgt tagccaggat  36240
ggtctcaatc tcctgacctc atgatccgcc cgcctcggcc tcccaaagtg ctgggattac  36300
aggcgtgagc catcacgtcc ggccagaaat catgaatatt agtaggtgaa aaataaacac  36360
attttaccac ctggaaaatg aaaaatactt gagtataatc taaataacaa tgggaagtgc  36420
agagttactt tccaggtctc ggtttaaata tgtcttaaac tttggccaat tagtagtaga  36480
agttgagaga aaaagtaact atctgacaaa gaaattataa gcagaatata taaagaactc  36540
ttaaaactga ataatcagaa aacaactcaa taaaaaggtg aaggatttga aaagatattt  36600
```

-continued

```
caccaaataa gacataggga tgacaaataa gcacatgaaa agactctcag catcactagt  36660
cacagggaaa tgcacgataa aaccacagtg agacaccatg gcacccctgt aggtatggct  36720
ttaatgaaga aataaaactg acaataccaa gtgttggcaa ggatccaagc agctgagact  36780
catatactgt taatgggaat gtaaaagtgt acagctttgg aaaacagttt ggcatttttt  36840
tgataaatgt atacttagcc atgtgatcca gcagtcccaa tcatgtatat ataaccaaaa  36900
gaaaagaaaa cttaggttca cataaaaact tatatcaaat gcttatagct gaccaggcat  36960
ggtggcccat gcctataatc ccagcacttt gggaggccga ggttggcaga tacctgaagt  37020
caagtgttcg agaccagcct ggccaacatg gcaaaaccct gtctctactt aaaatacaaa  37080
aattagccag gcgtgatggc aggcacctgt agtccagcta ttcaggaggc tgaggcagga  37140
gaatcacgtg aacccgggag gcagaggttg cagtgagccg agatcgtgcc actatactcc  37200
agcctgggtg acagagcaaa actctgtctc aaaaaaaaaa aaaaaaaaaa gggctggaca  37260
cggtggctta cgcctgttat cccggcactt tgggaggcca aggctgatgg atcacctgag  37320
gtcaggagtt caagaccagc ctggccaaca tggtgaaacc ccatctctac taaaaataca  37380
aaaatttgct gggcatggtg gtgggcacct gtaatcccag gaggctgagg caggagaatc  37440
acttgaaccc gggaggcgga gattgcagtg agccaagatt gtgccattga actccagcct  37500
gggtgacaag accaaaactc cttctcaaaa aaaaaaaaga ttatagcatc tttattcatc  37560
attgcccaaa attacaaact gcctaaatgt agaccttcat ttagttaatg aatgcacaaa  37620
ctgtggtata tccaaacaat tgaataaaaa aaggaatgaa ctggtacttt tttctattcc  37680
tcctgtttaa gtacagccaa aacacctcaa catttgtata aaacatgagc tgggctgggt  37740
gcggtggctc acacgtgtaa tcccagcact ttgggaggct gaggcgggtg gatcacctaa  37800
ggttgggagt tcaagaccgg tctgaccaac atggagaaac cctgtctcaa ctaaaaatac  37860
aagattagtc gggcatggtg gcgcatgcct gtaatcccag cttcttggga ggctgaggca  37920
ggagaattgc ttgatcccgg gaagcgaagg ttgcagtaag ctgagattgc accattgcac  37980
tccagcctgg gcaacaagag caaaactctg tctcaaaaag aaaaaaaaaa ccattcagct  38040
gaatctcaaa ggcagagaga agacagactg gctagggacc ttggaaccag aggagcagtg  38100
tggtggggag tggactggat tttctttttg cctcatttat cctggacttg gtgctggaga  38160
agctatgggt tcagaccaag agaaaacccc atgaaaagcc tgctctctct agccaaaaga  38220
ggcaacctag caagataaaa acctttagat aataagcact tgactccagt caaacaaaac  38280
agaataaact ggccccattc acccctgtca gcaaaggcca agtgggagcc aagatatgta  38340
ccccaacctg gaagtcataa ggtacacttc tccccttcc cagccaaggt ggtgttagag  38400
aaggctgact ggggagctgg gattctcatt ccctccagga ggtgataaca ctcctttcac  38460
atggtgtcag tggtcacagg gaggctgaac ttccacccag taatacatag gcatctctct  38520
ggctcctata tgggtgatgt tggagaagag gccgagtaga gaatccagac tgttgctgac  38580
acccagcagt aacaaggaca cctccacaat gtccgtggag gccatgtgga gatcagtaac  38640
aaggcactgc tctccctccc agtcagagag atgtcagtgg aggactaggg ggctagaact  38700
cccatgtgcg ttcagcagta atccccatga ccgccactcc ttgacatcac aggccttgaa  38760
gaaacctgga ctttcactcc cctctggttg tagcgaggtg gcactccctt ttccctgttg  38820
ccagtgctgt gtcagtggag gcttgctaaa ttggaagatg taaataagat tcacattctc  38880
ataacataat accccaaatt ttcaggattt aattgaaaat cactaagctg ggcatggtgg  38940
ctcacacctg taatcccagc actttgggag gccaaggtgg gccaaacact taaggtcagg  39000
```

-continued

```
aattcaagac cagcctggcc agcatggtga aaccctgtct ctactaaaaa tacaaaaatt  39060
agctgggcgt ggtggcacat gcctgtaatc ccagctactg ggaaggctaa ggcaggaaaa  39120
tcactggaac ctgggagacg gaggttgcag tgatccaaga tcgcactagt gtactgcagc  39180
ctgggcaaca gagcaagact ccatctaaat ttgtgtcagg attcccagaa ggagatgaga  39240
aagggtgggg ctgaaaaaaa ttgaggaaga agtcatggct gaaaatttcc caaatttggc  39300
aaaagtcaga aacctacaga ttgaaaaagc tgaatgaagc tcaaatatga taaactcaaa  39360
gaagttcaca cagagacaca tcacagtcag atttctgaac actgcagaca aaaaatgaag  39420
atctcgaaat tagcaagaaa tgaccttacc taagcaattt gaatgacagc agatttccca  39480
tcagagatca taaaggccag aaggaagggg tacatacaac atttttteta gtgctgaaag  39540
acaaaaactc taggctgggc acggtggcac acacctgtaa tcccagcact tttggaggct  39600
gaggcaggca gatcacctga agtcaggagt tcgagaccag cctggccaac atggggaaac  39660
cctgtctcta ctaaaaatac aaaaattagc caggtgtggt ggcacgcacc tataatccta  39720
gctacttggg aggctgaggc aggggaatcg cttgaacctg ggaggcgacg gttgcagtga  39780
gccaaggtcg cgccactgca ctccagcctg ggcagttgag cgagactcca tctcaaaaaa  39840
aaaaaaatta tccaggcttg gtggtgggcg cctatagtcc cagctacttg ggaggctgag  39900
gcaagagaat tggttgaacc caggaggtgg aggttgcagt gagccaagct catgccactg  39960
tactccagcc tgggtgacag agcgagacct tgtctcaaaa aaaaaaaaaa aaaaaaaaaa  40020
caagaaaaaa actctaaacc cagagttaca tatccagtga aatatccttc aggagtgaag  40080
ggaaaattaa cgatttgtct tcaggagacc taccctaaaa gaatggctaa aggaatttct  40140
ctaaacagaa aagaaatgat aaaagaagta attttggaac atcaggaagg aagaaagaac  40200
aataaaaaga gtaaaatatg ggtaaacaca atagactttc ccctcctttt gaattttcta  40260
aattgtatga tggttgaagc aagaattata gcactgattt ggttttcagt atatatattg  40320
gaaatattta aggcattatg ttacagatga aggagggtca aaggatataa agggaggtaa  40380
cctttctata tttcttttgt actgatgcag gcactttgga aaataatttc actatttgtt  40440
taaaaactga acataccctg accatatgac atagcatcta tactcctggg catttatccc  40500
agagaaacag aaatttattt attttttttt tagtattaca ctccgtaagt gctgtaatac  40560
tagcacttag ggaggctgag gcaagcagat tgcttgagcc caggagttca agaccagcct  40620
gggcaatgct gcacagtcaa aaaagaaaaa caaacattta gaaaactatt ttaaaagtct  40680
ttaattgctg aatgcctctt tggctaatat ttggaagatc attattatta tttttctttt  40740
ttaggcagag tcttgctctg tcactgaggc tggagtgcag tggcgccatc tcggcttact  40800
gcaacctctg cctcccgggt tcacgccatt ctcctgcctc agcctcccga gtagctggga  40860
ctacaggcgt gtgccaccat gcccggctaa tttttgtgt ttttagtaga gatggggttt  40920
cactatgtta gtcaggatgg tctccatctc ctaacctcgt gatccgccca cctcggcttc  40980
ccaaaatgct gggattacag gcgtgagcca ctgtgcccag cctggaagat cattatttag  41040
tcctacaact gacacattgt tccactgacg caattgccca ggctggtctt gaactcctgg  41100
gctcaagcaa tctgcctgcc tcggcctccc taagtgctag tattacaggc ttgagccact  41160
gtgcccagcc aaaaatagaa atttatattc tcacaaaaac atgtacatga atgtttatag  41220
cagctttact tgtcataatc aaaaactgga aacaaccaaa atgtcctaca gtgaaacaaa  41280
ctgtagtaca tccatagcat gtaatactct actgtcagga ttaaaaagaa acccactgtt  41340
```

-continued

```
ggcacaggca gcaccgtggc tggatctcag gggcattatg ctgagtgcaa aaaagcctca  41400
aagggtctta cactgtatga ttccacttgt tcaactaaaa atgacagctg tatagagata  41460
gagaacatat tagtggtttc cactagttag agaaagtggg taaaagatag gtgggtggga  41520
atataaatcg atagcaggga gatctttgtg gtattataac acttctatgt cttgattgta  41580
gtggtggtgg ttacatgaat acacgtgtga taaaatgcca tgtagaacta catataacgt  41640
tgtgccaatg tcaatatcta ggttttagtt tgatctttag ttacataaga tgtaactatt  41700
gggtgaaatt gggcaaaaga gtacacgaaa cctctcttaa atatctttac aacttccttt  41760
gaattgacag tttttcaaaa tagaaagttg ggtttttgta aatacatgaa ttgttgatat  41820
acacaacaaa tctcaaatgc attatgctac gtgaaagaag ccatattcaa aaggctacat  41880
acctactgat gccttttata tgacgtgcag gaaaagataa aactgtagga cagagaatat  41940
actggtggct atctgggatt aggaaatggg gatcgaccac aaaggggcag catgggggaa  42000
ttttctgggg caatggaatg gttgtgtatc ttgatggtgt atttgtcaaa atatatagaa  42060
ctataaaagt aaattttgct ttatatgtat taaatcaaaa aaagaaactc gtgctcaaat  42120
agaaatacat tttctgagaa cttgcctttt gatgactttg agaattttct ggaaatttta  42180
aagaaatgtg gttttgtttc ccaacaggtg atgctatgag tgaagaagac atgcttcagg  42240
cagctgtgac catgtcttta gaaactgtca gaaatgattt gaaaacagaa ggaaaaaaat  42300
aataccttta aaaaataatt tagatattca tactttccaa cattatcctg tgtgattaca  42360
gcatagggtc cactttggta atgtgtcaaa gagatgagga aataagactt ttagcggttt  42420
gcaaacaaaa tgatgggaaa gtggaacaat gcgtcggttg taggactaaa taatgatctt  42480
ccaaatatta gccaaagagg cattcagcaa ttaaagacat ttaaaatagt tttctaaatg  42540
tttctttttc ttttttgagt gtgcaatatg taacatgtct aaagttaggg cattttttctt  42600
ggatcttttt gcagactagc taattagctc tcgcctcagg ctttttccat atagtttgtt  42660
ttctttttct gtcttgtagg taagttggct cacatcatgt aatagtggct ttcatttctt  42720
attaaccaaa ttaacctttc aggaaagtat ctctactttc ctgatgttga taatagtaat  42780
ggttctagaa ggatgaacag ttctcccttc aactgtatac cgtgtgctcc agtgttttct  42840
tgtgttgttt tctctgatca caacttttct gctacctggt tttcattatt ttcccacaat  42900
tcttttgaaa gatggtaatc ttttctgagg tttagcgttt taagccctac gatgggatca  42960
ttatttcatg actggtgcgt tcctaaactc tgaaatcagc cttgcacaag tacttgagaa  43020
taaatgagca ttttttaaaa tgtgtgagca tgtgctttcc cagatgcttt atgaatgtct  43080
tttcacttat atcaaaacct tacagctttg ttgcaacccc ttcttcctgc gccttatttt  43140
ttcctttctt ctccaattga gaaaactagg agaagcatag tatgcaggca agtctccttc  43200
tgttagaaga ctaaacatac gtacccacca tgaatgtatg atacatgaaa tttggccttc  43260
aattttaata gcagttttat tttattttt ctcctatgac tggagctttg tgttctcttt  43320
acagttgagt catggaatgt aggtgtctgc ttcacatctt ttagtaggta tagcttgtca  43380
aagatggtga tctggaacat gaaaataatt tactaatgaa aatatgttta aatttatact  43440
gtgatttgac acttgcatca tgtttagata gcttaagaac aatggaagtc acagtactta  43500
gtggatctat aaataagaaa gtccatagtt ttgataaata ttctctttaa ttgagatgta  43560
cagagagttt cttgctgggt caataggata gtatcatttt ggtgaaaacc atgtctctga  43620
aattgatgtt ttagtttcag tgttccctat ccctcattct ccatctcctt ttgaagctct  43680
tttgaatgtt gaattgttca taagctaaaa tccaagaaat ttcagctgac aacttcgaaa  43740
```

attataatat ggtatattgc cctcctggtg tgtggctgca cacattttat cagggaaagt 43800
tttttgatct aggatttatt gctaactaac tgaaaagaga agaaaaaata tcttttattt 43860
atgattataa aatagctttt tcttcgatat aacagatttt ttaagtcatt attttgtgcc 43920
aatcagtttt ctgaagtttc ccttacacaa aaggatagct ttattttaaa atctaaagtt 43980
tcttttaata gttaaaaatg tttcagaaga attataaaac tttaaaactg caagggatgt 44040
tggagtttag tactactccc tcaagattta aaaagctaaa tattttaaga ctgaacattt 44100
atgttaatta ttaccagtgt gtttgtcata ttttccatgg atatttgttc attacctttt 44160
tccattgaaa agttacatta aacttttcat acacttgaat tgatgagcta cctaatataa 44220
aaatgagaaa accaatatgc attttaaagt tttaacttta gagtttataa agttcatata 44280
taccctagtt aaagcactta agaaaatatg gcatgtttga cttttagttc ctagagagtt 44340
tttgttttttg tttttgtttt tttttgagac ggagtcttgc tatgtctccc aggctggagg 44400
gcagtggcat gatctcggct cactacaact tccacctccc gggttcaagc aattctcctg 44460
cctcagcctc cagagtagct gggattacag gcgcccacca ccacacccgg cagatttttg 44520
tatttttggt agagacgcgg tttcatcatg tttggccagg ctggtctcga actcctgacc 44580
tcaggtgatc cgcctgcctt ggcctcccaa agtgttggga ttacaggcat gagccactgc 44640
gcctggccag ctagagagtt tttaaagcag agctgagcac acactggatg cgtttgaatg 44700
tgtttgtgta gtttgttgtg aaattgttac atttagcagg cagatccaga agcactagtg 44760
aactgtcatc ttggtggggt tggcttaaat ttaattgact gtttagattc catttcttaa 44820
ttgattggcc agtatgaaaa gatgccagtg caagtaacca tagtatcaaa aaagttaaaa 44880
attattcaaa gctatagttt atacatcagg tactgccatt tactgtaaac cacctgcaag 44940
aaagtcagga acaactaaat tcacaagaac tgtcctgcta agaagtgtat taaagatttc 45000
cattttgttt tactaattgg gaacatctta atgtttaata tttaaactat tggtatcatt 45060
tttctaatgt ataatttgta ttactgggat caagtatgta cagtggtgat gctagtagaa 45120
gtttaagcct tggaaatacc actttcatat tttcagatgt catggattta atgagtaatt 45180
tatgttttta aaattcagaa tagttaatct ctgatctaaa accatcaatc tatgtttttt 45240
acggtaatca tgtaaatatt tcagtaatat aaactgtttg aaaaggctgc tgcaggtaaa 45300
ctctatacta ggatcttggc caaataattt acaattcaca gaatatttta tttaaggtgg 45360
tgcttttttt ttttgtcctt aaaacttgat ttttcttaac tttattcatg atgccaaagt 45420
aaatgaggaa aaaaactcaa aaccagttga gtatcattgc agacaaaact accagtagtc 45480
catattgttt aatattaagt tgaataaaat aaattttatt tcagtcagag cctaaatcac 45540
attttgattg tctgaatttt tgatactatt tttaaaatca tgctagtggc ggctgggcgt 45600
ggtagctcac gcctgtaatc ccagcatttt gggaggccga agtgggtgga tcacgaggtc 45660
gggagttcga gaccagcttg gccaaaatgg tgaaacccca tctgtactaa aaactacaaa 45720
aattagctgg gcgcggtggc aggtgcctgt aatcccagct acctgggagt ctgaggcagg 45780
agaattgctt gaaccctggc gacagaggat gcagtgagcc aagatggtgc cactgtactc 45840
cagactgggc gacagagtga gactctgtct caaaaaaaaa aaaaaaatca tgctagtgcc 45900
aagagctact aaattcttaa aaccggccca ttggacctgt acagataaaa aatagattca 45960
gtgcataatc aaaatatgat aattttaaaa tcttaagtag aaaaataaat cttgatgttt 46020
taaattctta cgaggattca atagttaata ttgatgatct cccggctggg tgcagtggct 46080

-continued

```
cacgcctgta atcccagcag ttctggaggc tgaggtgggc gaatcacttc aggccaggag  46140
ttcaagacca gtctgggcaa catggtgaaa cctcgtttct actaaaaata caaaaattag  46200
ccgggcgtgg ttgcacacac ttgtaatccc agctactcag gaggctaaga atcgcatgag  46260
cctaggaggc agaggttgca gagtgccaag ggctcaccac tgcattccag cctgcccaac  46320
agagtgagac actgtttctg aaaaaaaaaa atatatatat atatatatat atgtgtgtat  46380
atatatatgt atatatatat gacttcctat taaaaacttt atcccagtcg gggcagtgg  46440
ctcacgcctg taatcccaac actttgggag gctgaggcag gtggatcacc tgaagtccgg  46500
agtttgagac cagcctggcc aacatggtga aaccccatct ctactaaaaa tacaaaactt  46560
aagccaggta tggtggcggg cacctgtaat cccagttact tgggaggctg aggcaggaga  46620
atcgtttaaa cccaggaggt ggaggttgca gtgagctgag atcgtgccat tgcactctag  46680
cctgggcaac aagagtaaaa ctccatctta aaggtttgtt tgttttttttt taatccggaa  46740
acgaagaggc gttgggccgc tattttcttt ttctttcttt ctttctttct ttttttttt  46800
ttctgagacg gagtctagct ctgctgccca ggctggagta caatgacacg atgttggctc  46860
actgcaacct ccacctcctg ggttcaagcg attctcctgc ctcagcctcc caagtacctg  46920
ggattacagg cacctgccac tacacctggc gaatatttgt ttttttagt agagacgggc  46980
ttttaccatg ttaggctggt ctcaaactcc tgacctcagg tgatctgcct gccttggcct  47040
cccaaagtgc tgggattaca ggtgcaggcc accacacccg gccttgggcc actgttttca  47100
aagtgaattg tttgttgtat cgagtcctta agtatggata tatatgtgac cctaattaag  47160
aactaccaga ttggatcaac taatcatgtc agcaatgtaa ataactttat ttttcatatt  47220
caaaataaaa actttctttt atttctggcc cctttataac cagcatcttt ttgctttaaa  47280
aaatgacctg gctttgtatt tttttagtct taaacataat aaaaatattt ttgttctaat  47340
ttgctttcat gagtgaagat tattgacatc gttggtaaat tctagaattt tgattttgtt  47400
ttttaatttg aagaaaatct ttgctattat tattttttcc aagtggtctg gcattttaag  47460
aattagtgct aataacgtaa cttctaaatt tgtcgtaatt ggcatgttta atagcatatc  47520
aaaaaacatt ttaagcctgt ggattcatag acaaagcaat gagaaacatt agtaaaatat  47580
aaatggatat tcctgatgca tttaggaagc tctcaattgt ctcttgcata gttcaaggaa  47640
tgttttctga atttttttaa tgcttttttt tttttgaaa gaggaaaaca tacattttta  47700
aatgtgatta tctaattttt acaacactgg gctattagga ataacttttt aaaaaattact  47760
gttctgtata aatatttgaa attcaagtac agaaaatatc tgaaacaaaa agcattgttg  47820
tttggccatg atacaagtgc actgtggcag tgccgcttgc tcaggaccca gccctgcagc  47880
ccttctgtgt gtgctccctc gttaagttca tttgctgtta ttacacacac aggccttcct  47940
gtctggtcgt tagaaaagcc gggcttccaa agcactgttg aacacaggat tctgttgtta  48000
gtgtggatgt tcaatgagtt gtattttaaa tatcaaagat tattaaataa agataatgtt  48060
tgcttttcta                                                         48070
```

<210> SEQ ID NO 2
<211> LENGTH: 6884
<212> TYPE: DNA
<213> ORGANISM: Homo sapiens

<400> SEQUENCE: 2

```
gtgggggccg ttggctccag acaaataaac atggagtcca tcttccacga gaaacaagaa     60
ggctcacttt gtgctcaaca ttgcctgaat aacttattgc aaggagaata ttttagccct    120
```

-continued

```
gtggaattat cctcaattgc acatcagctg gatgaggagg agaggatgag aatggcagaa    180
ggaggagtta ctagtgaaga ttatcgcacg tttttacagc agccttctgg aaatatggat    240
gacagtggtt ttttctctat tcaggttata agcaatgcct tgaaagtttg ggtttagaa     300
ctaatcctgt tcaacagtcc agagtatcag aggctcagga tcgatcctat aaatgaaaga    360
tcatttatat gcaattataa ggaacactgg tttacagtta gaaaattagg aaaacagtgg    420
tttaacttga attctctctt gacgggtcca gaattaatat cagatacata tcttgcactt    480
ttcttggctc aattacaaca ggaaggttat tctatatttg tcgttaaggg tgatctgcca    540
gattgcgaag ctgaccaact cctgcagatg attagggtcc aacagatgca tcgaccaaaa    600
cttattggag aagaattagc acaactaaaa gagcaaagag tccataaaac agacctggaa    660
cgagtgttag aagcaaatga tggctcagga atgttagacg aagatgagga ggatttgcag    720
agggctctgg cactaagtcg ccaagaaatt gacatggaag atgaggaagc agatctccgc    780
agggctattc agctaagtat gcaaggtagt tccagaaaca tatctcaaga tatgacacag    840
acatcaggta caaatcttac ttcagaagag cttcggaaga gacgagaagc ctactttgaa    900
aaacagcagc aaaagcagca acagcagcag cagcagcagc agcaggggga cctatcagga    960
cagagttcac atccatgtga aaggccagcc accagttcag gagcacttgg gagtgatcta   1020
ggtgatgcta tgagtgaaga agacatgctt caggcagctg tgaccatgtc tttagaaact   1080
gtcagaaatg atttgaaaac agaaggaaaa aaataatacc tttaaaaaat aatttagata   1140
ttcatacttt ccaacattat cctgtgtgat tacagcatag ggtccacttt ggtaatgtgt   1200
caaagagatg aggaaataag acttttagcg gtttgcaaac aaaatgatgg gaaagtggaa   1260
caatgcgtcg gttgtaggac taaataatga tcttccaaat attagccaaa gaggcattca   1320
gcaattaaag acatttaaaa tagttttcta aatgtttctt tttctttttt gagtgtgcaa   1380
tatgtaacat gtctaaagtt agggcatttt tcttggatct tttgcagac tagctaatta    1440
gctctcgcct caggcttttt ccatatagtt tgttttcttt ttctgtcttg taggtaagtt   1500
ggctcacatc atgtaatagt ggctttcatt tcttattaac caaattaacc tttcaggaaa   1560
gtatctctac tttcctgatg ttgataatag taatggttct agaaggatga acagttctcc   1620
cttcaactgt ataccgtgtg ctccagtgtt ttcttgtgtt gttttctctg atcacaactt   1680
ttctgctacc tggttttcat tattttccca caattctttt gaaagatggt aatcttttct   1740
gaggtttagc gttttaagcc ctacgatggg atcattattt catgactggt gcgttcctaa   1800
actctgaaat cagccttgca caagtacttg agaataaatg agcatttttt aaaatgtgtg   1860
agcatgtgct ttcccagatg ctttatgaat gtcttttcac ttatatcaaa accttacagc   1920
tttgttgcaa ccccttcttc ctgcgcctta ttttttcctt tcttctccaa ttgagaaaac   1980
taggagaagc atagtatgca ggcaagtctc cttctgttag aagactaaac atacgtaccc   2040
accatgaatg tatgatacat gaaatttggc cttcaatttt aatagcagtt ttattttatt   2100
ttttctccta tgactggagc tttgtgttct ctttacagtt gagtcatgga atgtaggtgt   2160
ctgcttcaca tcttttagta ggtatagctt gtcaaagatg gtgatctgga acatgaaaat   2220
aatttactaa tgaaaatatg tttaaattta tactgtgatt tgacacttgc atcatgttta   2280
gatagcttaa gaacaatgga agtcacagta cttagtggat ctataaataa gaaagtccat   2340
agttttgata aatattctct ttaattgaga tgtacagaga gtttcttgct gggtcaatag   2400
gatagtatca ttttggtgaa aaccatgtct ctgaaattga tgttttagtt tcagtgttcc   2460
```

-continued

```
ctatccctca ttctccatct ccttttgaag ctcttttgaa tgttgaattg ttcataagct   2520
aaaatccaag aaatttcagc tgacaacttc gaaaattata atatggtata ttgccctcct   2580
ggtgtgtggc tgcacacatt ttatcaggga aagtttttg atctaggatt tattgctaac    2640
taactgaaaa gagaagaaaa aatatctttt atttatgatt ataaaatagc tttttcttcg   2700
atataacaga ttttttaagt cattattttg tgccaatcag ttttctgaag tttcccttac   2760
acaaaaggat agctttattt taaaatctaa agtttctttt aatagttaaa aatgtttcag   2820
aagaattata aaactttaaa actgcaaggg atgttggagt ttagtactac tccctcaaga   2880
tttaaaaagc taaatatttt aagactgaac atttatgtta attattacca gtgtgtttgt   2940
catattttcc atggatattt gttcattacc tttttccatt gaaaagttac attaaacttt   3000
tcatacactt gaattgatga gctacctaat ataaaaatga gaaaaccaat atgcatttta   3060
aagttttaac tttagagttt ataaagttca tatataccct agttaaagca cttaagaaaa   3120
tatggcatgt ttgactttta gttcctagag agtttttgtt tttgtttttg tttttttttg   3180
agacggagtc ttgctatgtc tcccaggctg gagggcagtg gcatgatctc ggctcactac   3240
aacttccacc tcccgggttc aagcaattct cctgcctcag cctccagagt agctgggatt   3300
acaggcgccc accaccacac ccggcagatt tttgtatttt tggtagagac gcggtttcat   3360
catgtttggc caggctggtc tcgaactcct gacctcaggt gatccgcctg ccttggcctc   3420
ccaaagtgtt gggattacag gcatgagcca ctgcgcctgg ccagctagag agtttttaaa   3480
gcagagctga gcacacactg gatgcgtttg aatgtgtttg tgtagtttgt tgtgaaattg   3540
ttacatttag caggcagatc cagaagcact agtgaactgt catcttggtg gggttggctt   3600
aaatttaatt gactgtttag attccatttc ttaattgatt ggccagtatg aaaagatgcc   3660
agtgcaagta accatagtat caaaaaagtt aaaaaattatt caaagctata gtttatacat  3720
caggtactgc catttactgt aaaccacctg caagaaagtc aggaacaact aaattcacaa   3780
gaactgtcct gctaagaagt gtattaaaga tttccatttt gttttactaa ttgggaacat   3840
cttaatgttt aatatttaaa ctattggtat catttttcta atgtataatt tgtattactg   3900
ggatcaagta tgtacagtgg tgatgctagt agaagtttaa gccttggaaa taccactttc   3960
atattttcag atgtcatgga tttaatgagt aatttatgtt tttaaaattc agaatagtta   4020
atctctgatc taaaaccatc aatctatgtt ttttacggta atcatgtaaa tatttcagta   4080
atataaactg tttgaaaagg ctgctgcagg taaactctat actaggatct tggccaaata   4140
atttacaatt cacagaatat tttatttaag gtggtgcttt tttttttgt ccttaaaact    4200
tgatttttct taactttatt catgatgcca aagtaaatga ggaaaaaaac tcaaaaccag   4260
ttgagtatca ttgcagacaa aactaccagt agtccatatt gtttaatatt aagttgaata   4320
aaataaattt tatttcagtc agagcctaaa tcacattttg attgtctgaa tttttgatac   4380
tatttttaaa atcatgctag tggcggctgg gcgtggtagc tcacgcctgt aatcccagca   4440
ttttgggagg ccgaagtggg tggatcacga ggtcgggagt tcgagaccag cttggccaaa   4500
atggtgaaac cccatctgta ctaaaaacta caaaaattag ctgggcgcgg tggcaggtgc   4560
ctgtaatccc agctacctgg gagtctgagg caggagaatt gcttgaaccc tggcgacaga   4620
ggatgcagtg agccaagatg gtgccactgt actccagact gggcgacaga gtgagactct   4680
gtctcaaaaa aaaaaaaaaa atcatgctag tgccaagagc tactaaattc ttaaaaccgg   4740
cccattggac ctgtacagat aaaaaataga ttcagtgcat aatcaaaata tgataatttt   4800
aaaatcttaa gtagaaaaat aaatcttgat gttttaaatt cttacgagga ttcaatagtt   4860
```

-continued

```
aatattgatg atctcccggc tgggtgcagt ggctcacgcc tgtaatccca gcagttctgg   4920

aggctgaggt gggcgaatca cttcaggcca ggagttcaag accagtctgg gcaacatggt   4980

gaaacctcgt ttctactaaa aatacaaaaa ttagccgggc gtggttgcac acacttgtaa   5040

tcccagctac tcaggaggct aagaatcgca tgagcctagg aggcagaggt tgcagagtgc   5100

caagggctca ccactgcatt ccagcctgcc caacagagtg agacactgtt tctgaaaaaa   5160

aaaaatatat atatatatat atatatgtgt gtatatatat atgtatatat atatgacttc   5220

ctattaaaaa ctttatccca gtcgggggca gtggctcacg cctgtaatcc caacactttg   5280

ggaggctgag gcaggtggat cacctgaagt ccggagtttg agaccagcct ggccaacatg   5340

gtgaaacccc atctctacta aaaatacaaa acttaagcca ggtatggtgg cgggcacctg   5400

taatcccagt tacttgggag gctgaggcag gagaatcgtt taaacccagg aggtggaggt   5460

tgcagtgagc tgagatcgtg ccattgcact ctagcctggg caacaagagt aaaactccat   5520

cttaaaggtt tgtttgtttt tttttaatcc ggaaacgaag aggcgttggg ccgctatttt   5580

ctttttcttt ctttctttct ttcttttttt tttttctga gacggagtct agctctgctg   5640

cccaggctgg agtacaatga cacgatgttg gctcactgca acctccacct cctgggttca   5700

agcgattctc ctgcctcagc ctcccaagta cctgggatta caggcacctg ccactacacc   5760

tggcgaatat ttgttttttt tagtagagac gggcttttac catgttaggc tggtctcaaa   5820

ctcctgacct caggtgatct gcctgccttg gcctcccaaa gtgctgggat tacaggtgca   5880

ggccaccaca cccggccttg ggccactgtt ttcaaagtga attgtttgtt gtatcgagtc   5940

cttaagtatg gatatatatg tgaccctaat taagaactac cagattggat caactaatca   6000

tgtcagcaat gtaaataact ttatttttca tattcaaaat aaaaactttc ttttatttct   6060

ggccccttta taaccagcat ctttttgctt taaaaaatga cctggctttg tattttttta   6120

gtcttaaaca taataaaaat atttttgttc taatttgctt tcatgagtga agattattga   6180

catcgttggt aaattctaga attttgattt tgttttttaa tttgaagaaa atctttgcta   6240

ttattatttt ttccaagtgg tctggcattt taagaattag tgctaataac gtaacttcta   6300

aatttgtcgt aattggcatg tttaatagca tatcaaaaaa cattttaagc ctgtggattc   6360

atagacaaag caatgagaaa cattagtaaa atataaatgg atattcctga tgcatttagg   6420

aagctctcaa ttgtctcttg catagttcaa ggaatgtttt ctgaattttt ttaatgcttt   6480

tttttttttt gaaagaggaa aacatacatt tttaaatgtg attatctaat ttttacaaca   6540

ctgggctatt aggaataact ttttaaaaat tactgttctg tataaatatt tgaaattcaa   6600

gtacagaaaa tatctgaaac aaaaagcatt gttgtttggc catgatacaa gtgcactgtg   6660

gcagtgccgc ttgctcagga cccagccctg cagcccttct gtgtgtgctc cctcgttaag   6720

ttcatttgct gttattacac acacaggcct tcctgtctgg tcgttagaaa agccgggctt   6780

ccaaagcact gttgaacaca ggattctgtt gttagtgtgg atgttcaatg agttgtattt   6840

taaatatcaa agattattaa ataaagataa tgtttgcttt tcta                     6884
```

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(13),(15)..(18)

-continued

<223> OTHER INFORMATION: m5c

<400> SEQUENCE: 3
gcgtaggtga tgctcccc 18

<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(8),(10),(11),(18)
<223> OTHER INFORMATION: m5c

<400> SEQUENCE: 4
aggaatcctc cgaaaagc 18

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(9),(11),(12)
<223> OTHER INFORMATION: m5c

<400> SEQUENCE: 5
aaggaatcct ccgaaaag 18

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (10),(11),(13),(14)
<223> OTHER INFORMATION: m5c

<400> SEQUENCE: 6
tgaaggaatc ctccgaaa 18

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (11),(12),(14),(15)
<223> OTHER INFORMATION: m5c

<400> SEQUENCE: 7
gtgaaggaat cctccgaa 18

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (12),(13),(15),(16)
<223> OTHER INFORMATION: m5c

<400> SEQUENCE: 8
ggtgaaggaa tcctccga 18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (13),(14),(16),(17)
<223> OTHER INFORMATION: m5c

<400> SEQUENCE: 9
gggtgaagga atcctccg 18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(5),(6)
<223> OTHER INFORMATION: m5c

<400> SEQUENCE: 10
gactccaata tagaattg 18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(7),(8),(9),(12)
<223> OTHER INFORMATION: m5c

<400> SEQUENCE: 11
gtcaggccct acagtggg 18

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(8),(9),(10),(13)
<223> OTHER INFORMATION: m5c

<400> SEQUENCE: 12
tgtcaggccc tacagtgg 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide
<220> FEATURE:

<221> NAME/KEY: modified_base
<222> LOCATION: (1),(4),(7),(8),(9)
<223> OTHER INFORMATION: m5c

<400> SEQUENCE: 13
cgacttccct gtttaggg 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(5),(8),(9),(10)
<223> OTHER INFORMATION: m5c

<400> SEQUENCE: 14
acgacttccc tgtttagg 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(6),(9),(10),(11)
<223> OTHER INFORMATION: m5c

<400> SEQUENCE: 15
gacgacttcc ctgtttag 18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(6),(8),(9)
<223> OTHER INFORMATION: m5c

<400> SEQUENCE: 16
gcctgctccg gaaagatg 18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (13)
<223> OTHER INFORMATION: m5c

<400> SEQUENCE: 17
agtagtgtgg aacatgtt 18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 18
gaagtagtgt ggaacatg 18

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 19
ggaagtagtg tggaacat 18

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (17)
<223> OTHER INFORMATION: m5c

<400> SEQUENCE: 20
aggaagtagt gtggaaca 18

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(18)
<223> OTHER INFORMATION: m5c

<400> SEQUENCE: 21
caggaagtag tgtggaac 18

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(4),(5),(8),(16)
<223> OTHER INFORMATION: m5c

<400> SEQUENCE: 22
gtcccaacta ggtaacaa 18

<210> SEQ ID NO 23
<211> LENGTH: 18
<212> TYPE: DNA
<213> ORGANISM: Artificial sequence
<220> FEATURE:

<223> OTHER INFORMATION: Synthetic oligonucleotide
<220> FEATURE:
<221> NAME/KEY: modified_base
<222> LOCATION: (2),(18)
<223> OTHER INFORMATION: m5c

<400> SEQUENCE: 23
tcgggtaagt agattttc 18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(4),(10),(12),(16)
<223> OTHER INFORMATION: m5c

<400> SEQUENCE: 24
aggcctatac acatgctg 18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(15),(16)
<223> OTHER INFORMATION: m5c

<400> SEQUENCE: 25
gaagtatctg taggccta 18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4)
<223> OTHER INFORMATION: m5c

<400> SEQUENCE: 26
ggactgtata ggagatta 18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8)
<223> OTHER INFORMATION: m5c

<400> SEQUENCE: 27
gaatggactg tataggag 18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(4),(11),(13),(15),(16)
<223> OTHER INFORMATION: m5c

<400> SEQUENCE: 28
cctcttagtg ctctccga 18

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(5),(12),(14),(16),(17)
<223> OTHER INFORMATION: m5c

<400> SEQUENCE: 29
tcctcttagt gctctccg 18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(8),(12),(16)
<223> OTHER INFORMATION: m5c

<400> SEQUENCE: 30
aagctgtcaa tctagcag 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(9),(13),(17)
<223> OTHER INFORMATION: m5c

<400> SEQUENCE: 31
gggacaagct gtcaatct 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(6),(7),(11),(14)
<223> OTHER INFORMATION: m5c

<400> SEQUENCE: 32
taggcccaga cttcattg 18

<210> SEQ ID NO 33
<211> LENGTH: 18
<212> TYPE: DNA

-continued

<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(7),(8),(12),(15)
<223> OTHER INFORMATION: m5c

<400> SEQUENCE: 33
ttaggcccag acttcatt 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(8),(9),(13),(16)
<223> OTHER INFORMATION: m5c

<400> SEQUENCE: 34
tttaggccca gacttcat 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(7),(14),(15),(16),(18)
<223> OTHER INFORMATION: m5c

<400> SEQUENCE: 35
caatgacaat gagcccac 18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (12)
<223> OTHER INFORMATION: m5c

<400> SEQUENCE: 36
gttataggat gcaggtaa 18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (13)
<223> OTHER INFORMATION: m5c

<400> SEQUENCE: 37
ggttatagga tgcaggta 18

<210> SEQ ID NO 38
<211> LENGTH: 18

<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14)
<223> OTHER INFORMATION: m5c

<400> SEQUENCE: 38
aggttatagg atgcaggt 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
ataatgggag gttatagg 18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (11),(18)
<223> OTHER INFORMATION: m5c

<400> SEQUENCE: 40
gaataagtag cttggagc 18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 41
gtaaggaata agtagctt 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(5),(6),(14),(15),(16),(17)
<223> OTHER INFORMATION: m5c

<400> SEQUENCE: 42
gacaccaggt ttgcccct 18

<210> SEQ ID NO 43
<211> LENGTH: 18
<212> TYPE: DNA
<213> ORGANISM: Artificial sequence
<220> FEATURE:

-continued

<223> OTHER INFORMATION: Synthetic oligonucleotide
<220> FEATURE:
<221> NAME/KEY: modified_base
<222> LOCATION: (4),(6),(7),(15),(16),(17),(18)
<223> OTHER INFORMATION: m5c

<400> SEQUENCE: 43
agacaccagg tttgcccc 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15),(18)
<223> OTHER INFORMATION: m5c

<400> SEQUENCE: 44
atgggaggta ggtacaac 18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(7),(9),(10),(11),(15),(17)
<223> OTHER INFORMATION: m5c

<400> SEQUENCE: 45
ggactgcacc caagctca 18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(11),(13),(14),(15)
<223> OTHER INFORMATION: m5c

<400> SEQUENCE: 46
agagggactg cacccaag 18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9),(12),(14),(15),(16)
<223> OTHER INFORMATION: m5c

<400> SEQUENCE: 47
aagagggact gcacccaa 18

<210> SEQ ID NO 48
<211> LENGTH: 18
<212> TYPE: DNA
<213> ORGANISM: Artificial sequence -continued
<220> FEATURE:
<223> OTHER INFORMATION: Synthetic oligonucleotide
<220> FEATURE:
<221> NAME/KEY: modified_base
<222> LOCATION: (1),(2),(3),(4),(6),(8)
<223> OTHER INFORMATION: m5c

<400> SEQUENCE: 48
ccccactcta atatgaag 18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(5),(7),(18)
<223> OTHER INFORMATION: m5c

<400> SEQUENCE: 49
gtcgctcagg agaggttc 18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(6),(8)
<223> OTHER INFORMATION: m5c

<400> SEQUENCE: 50
ggtcgctcag gagaggtt 18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(7),(9)
<223> OTHER INFORMATION: m5c

<400> SEQUENCE: 51
aggtcgctca ggagaggt 18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(6),(10)
<223> OTHER INFORMATION: m5c

<400> SEQUENCE: 52
taggtcgctc aggagagg 18

<210> SEQ ID NO 53
<211> LENGTH: 18
<212> TYPE: DNA

<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(9),(11)
<223> OTHER INFORMATION: m5c

<400> SEQUENCE: 53
ataggtcgct caggagag 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(12),(14),(16)
<223> OTHER INFORMATION: m5c

<400> SEQUENCE: 54
cagagatagg tcgctcag 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(5),(16),(18)
<223> OTHER INFORMATION: m5c

<400> SEQUENCE: 55
tctgcagaga taggtcgc 18

<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(9),(11)
<223> OTHER INFORMATION: m5c

<400> SEQUENCE: 56
cggtaaagca ctagatgg 18

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(10),(12)
<223> OTHER INFORMATION: m5c

<400> SEQUENCE: 57
acggtaaagc actagatg 18

<210> SEQ ID NO 58
<211> LENGTH: 18

<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(8),(16),(18)
<223> OTHER INFORMATION: m5c

<400> SEQUENCE: 58
agtggcacgg taaagcac 18

<210> SEQ ID NO 59
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(10),(11),(14),(16)
<223> OTHER INFORMATION: m5c

<400> SEQUENCE: 59
agtgctgggc ctactctg 18

<210> SEQ ID NO 60
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(11),(12),(15),(17)
<223> OTHER INFORMATION: m5c

<400> SEQUENCE: 60
aagtgctggg cctactct 18

<210> SEQ ID NO 61
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(18)
<223> OTHER INFORMATION: m5c

<400> SEQUENCE: 61
gctatgttag ttgtgtac 18

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(6),(8),(11),(14),(17)
<223> OTHER INFORMATION: m5c

<400> SEQUENCE: 62
aacgtctctg cagcagct 18

<210> SEQ ID NO 63

<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(17)
<223> OTHER INFORMATION: m5c

<400> SEQUENCE: 63
gaagctaagt aggtgact 18

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(18)
<223> OTHER INFORMATION: m5c

<400> SEQUENCE: 64
tgaagctaag taggtgac 18

<210> SEQ ID NO 65
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (11),(12),(13),(15),(17)
<223> OTHER INFORMATION: m5c

<400> SEQUENCE: 65
agaggtgatt cccactcg 18

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (12),(13),(14),(16),(18)
<223> OTHER INFORMATION: m5c

<400> SEQUENCE: 66
tagaggtgat tcccactc 18

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(13),(14),(15),(17)
<223> OTHER INFORMATION: m5c

<400> SEQUENCE: 67
ctagaggtga ttcccact 18

<210> SEQ ID NO 68
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(14),(15),(16),(18)
<223> OTHER INFORMATION: m5c

<400> SEQUENCE: 68
cctagaggtg attcccac 18

<210> SEQ ID NO 69
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9),(14)
<223> OTHER INFORMATION: m5c

<400> SEQUENCE: 69
ggtaatagct aagcaaga 18

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(7),(13)
<223> OTHER INFORMATION: m5c

<400> SEQUENCE: 70
gctactctgg tacaggaa 18

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(7),(9)
<223> OTHER INFORMATION: m5c

<400> SEQUENCE: 71
cctagtcact ttgataga 18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(4),(11),(13),(16)
<223> OTHER INFORMATION: m5c

<400> SEQUENCE: 72
gcactaaagg ctcatctg 18

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(7)
<223> OTHER INFORMATION: m5c

<400> SEQUENCE: 73
gaacatcttg agtaggtg 18

<210> SEQ ID NO 74
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(8)
<223> OTHER INFORMATION: m5c

<400> SEQUENCE: 74
ggaacatctt gagtaggt 18

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(9)
<223> OTHER INFORMATION: m5c

<400> SEQUENCE: 75
aggaacatct tgagtagg 18

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(7),(10)
<223> OTHER INFORMATION: m5c

<400> SEQUENCE: 76
caggaacatc ttgagtag 18

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)
<223> OTHER INFORMATION: m5c

<400> SEQUENCE: 77
tgttcagggt agatgtca 18

<210> SEQ ID NO 78
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7)
<223> OTHER INFORMATION: m5c

<400> SEQUENCE: 78
ggtgttcagg gtagatgt 18

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8)
<223> OTHER INFORMATION: m5c

<400> SEQUENCE: 79
aggtgttcag ggtagatg 18

<210> SEQ ID NO 80
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9),(14),(18)
<223> OTHER INFORMATION: m5c

<400> SEQUENCE: 80
gggtgggaca taacaggc 18

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (10),(15)
<223> OTHER INFORMATION: m5c

<400> SEQUENCE: 81
agggtgggac ataacagg 18

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(8),(11),(12),(13),(18)
<223> OTHER INFORMATION: m5c

<400> SEQUENCE: 82
ggatactctg ccctgttc 18

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(9),(12),(13),(14)
<223> OTHER INFORMATION: m5c

<400> SEQUENCE: 83
tggatactct gccctgtt 18

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(11),(14),(16),(18)
<223> OTHER INFORMATION: m5c

<400> SEQUENCE: 84
aagctagatg ctacacac 18

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(5),(16)
<223> OTHER INFORMATION: m5c

<400> SEQUENCE: 85
caaacgtgtg gtttgcat 18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(6),(17)
<223> OTHER INFORMATION: m5c

<400> SEQUENCE: 86
tcaaacgtgt ggtttgca 18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(7),(18)
<223> OTHER INFORMATION: m5c

<400> SEQUENCE: 87

```
gtcaaacgtg tggtttgc                                              18


<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(8)
<223> OTHER INFORMATION: m5c

<400> SEQUENCE: 88

tgtcaaacgt gtggtttg                                              18


<210> SEQ ID NO 89
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(10)
<223> OTHER INFORMATION: m5c

<400> SEQUENCE: 89

ggtgtcaaac gtgtggtt                                              18


<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(5),(8),(9)
<223> OTHER INFORMATION: m5c

<400> SEQUENCE: 90

gtaccttcct gtgatggt                                              18


<210> SEQ ID NO 91
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(5),(8),(10),(12),(16)
<223> OTHER INFORMATION: m5c

<400> SEQUENCE: 91

caggctactc acttactg                                              18


<210> SEQ ID NO 92
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(6),(9),(11),(13),(17)
<223> OTHER INFORMATION: m5c
```

<400> SEQUENCE: 92
gcaggctact cacttact 18

<210> SEQ ID NO 93
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(7),(10),(12),(14),(18)
<223> OTHER INFORMATION: m5c

<400> SEQUENCE: 93
agcaggctac tcacttac 18

<210> SEQ ID NO 94
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(8),(11),(13),(15)
<223> OTHER INFORMATION: m5c

<400> SEQUENCE: 94
gagcaggcta ctcactta 18

<210> SEQ ID NO 95
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(9),(12),(14),(16)
<223> OTHER INFORMATION: m5c

<400> SEQUENCE: 95
tgagcaggct actcactt 18

<210> SEQ ID NO 96
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(10),(14),(17)
<223> OTHER INFORMATION: m5c

<400> SEQUENCE: 96
ttgactgagc aggctact 18

<210> SEQ ID NO 97
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(6),(11),(15),(18)
<223> OTHER INFORMATION: m5c

<400> SEQUENCE: 97
cttgactgag caggctac 18

<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(7),(12),(16)
<223> OTHER INFORMATION: m5c

<400> SEQUENCE: 98
acttgactga gcaggcta 18

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(5),(6),(7),(10),(11)
<223> OTHER INFORMATION: m5c

<400> SEQUENCE: 99
caggcccttc catagtgt 18

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(6),(7),(8),(11),(12)
<223> OTHER INFORMATION: m5c

<400> SEQUENCE: 100
ccaggccctt ccatagtg 18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(7),(8),(9),(12),(13)
<223> OTHER INFORMATION: m5c

<400> SEQUENCE: 101
tccaggccct tccatagt 18

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(7)

<223> OTHER INFORMATION: m5c

<400> SEQUENCE: 102
cgtgtgctag tatttgtt 18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(8)
<223> OTHER INFORMATION: m5c

<400> SEQUENCE: 103
ccgtgtgcta gtatttgt 18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(4),(10)
<223> OTHER INFORMATION: m5c

<400> SEQUENCE: 104
ggccgtgtgc tagtattt 18

<210> SEQ ID NO 105
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(5),(11)
<223> OTHER INFORMATION: m5c

<400> SEQUENCE: 105
tggccgtgtg ctagtatt 18

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(6),(12)
<223> OTHER INFORMATION: m5c

<400> SEQUENCE: 106
ttggccgtgt gctagtat 18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(7),(13)
<223> OTHER INFORMATION: m5c

<400> SEQUENCE: 107
attggccgtg tgctagta 18

<210> SEQ ID NO 108
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(8),(14)
<223> OTHER INFORMATION: m5c

<400> SEQUENCE: 108
gattggccgt gtgctagt 18

<210> SEQ ID NO 109
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(9),(13),(14),(15)
<223> OTHER INFORMATION: m5c

<400> SEQUENCE: 109
aaggttgcct gaccctgt 18

<210> SEQ ID NO 110
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(9),(10),(14),(15),(16)
<223> OTHER INFORMATION: m5c

<400> SEQUENCE: 110
caaggttgcc tgaccctg 18

<210> SEQ ID NO 111
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(10),(11),(15),(16),(17)
<223> OTHER INFORMATION: m5c

<400> SEQUENCE: 111
acaaggttgc ctgaccct 18

<210> SEQ ID NO 112
<211> LENGTH: 18
<212> TYPE: DNA
<213> ORGANISM: Artificial sequence
<220> FEATURE:
<223> OTHER INFORMATION: Synthetic oligonucleotide
<220> FEATURE:

<221> NAME/KEY: modified_base
<222> LOCATION: (5),(13),(14),(18)
<223> OTHER INFORMATION: m5c

<400> SEQUENCE: 112
ggtacaaggt tgcctgac 18

<210> SEQ ID NO 113
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(14),(15)
<223> OTHER INFORMATION: m5c

<400> SEQUENCE: 113
gggtacaagg ttgcctga 18

<210> SEQ ID NO 114
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14)
<223> OTHER INFORMATION: m5c

<400> SEQUENCE: 114
tagtagagtt ttgcttgg 18

<210> SEQ ID NO 115
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (18)
<223> OTHER INFORMATION: m5c

<400> SEQUENCE: 115
gatgtagtag agttttgc 18

<210> SEQ ID NO 116
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 116
tgatgtagta gagttttg 18

<210> SEQ ID NO 117
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)
<223> OTHER INFORMATION: m5c

<400> SEQUENCE: 117
ctgatgtagt agagtttt 18

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(10)
<223> OTHER INFORMATION: m5c

<400> SEQUENCE: 118
gtggtggctc aagtatta 18

<210> SEQ ID NO 119
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(18)
<223> OTHER INFORMATION: m5c

<400> SEQUENCE: 119
caagttggtt tgtggtac 18

<210> SEQ ID NO 120
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 120
gcaagttggt ttgtggta 18

<210> SEQ ID NO 121
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 121
tgcaagttgg tttgtggt 18

<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(4)

```
<223> OTHER INFORMATION: m5c

<400> SEQUENCE: 122

ctgcaagttg gtttgtgg                                                    18


<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(5)
<223> OTHER INFORMATION: m5c

<400> SEQUENCE: 123

cctgcaagtt ggtttgtg                                                    18


<210> SEQ ID NO 124
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(6)
<223> OTHER INFORMATION: m5c

<400> SEQUENCE: 124

tcctgcaagt tggtttgt                                                    18


<210> SEQ ID NO 125
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(7)
<223> OTHER INFORMATION: m5c

<400> SEQUENCE: 125

tctaggcaat tgtggtgg                                                    18


<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(7),(16),(18)
<223> OTHER INFORMATION: m5c

<400> SEQUENCE: 126

gcatggctaa tgatgcac                                                    18


<210> SEQ ID NO 127
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
```

<222> LOCATION: (12),(16)
<223> OTHER INFORMATION: m5c

<400> SEQUENCE: 127
tgtgaaggta gcgaacat 18

<210> SEQ ID NO 128
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (13),(17)
<223> OTHER INFORMATION: m5c

<400> SEQUENCE: 128
gtgtgaaggt agcgaaca 18

<210> SEQ ID NO 129
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(7),(10),(12),(15),(16),(17)
<223> OTHER INFORMATION: m5c

<400> SEQUENCE: 129
gtaactctgc acttccca 18

<210> SEQ ID NO 130
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7),(9),(12),(14),(17),(18)
<223> OTHER INFORMATION: m5c

<400> SEQUENCE: 130
aagtaactct gcacttcc 18

<210> SEQ ID NO 131
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(6),(7),(8),(14)
<223> OTHER INFORMATION: m5c

<400> SEQUENCE: 131
gtcatcccta tgtcttat 18

<210> SEQ ID NO 132
<211> LENGTH: 18
<212> TYPE: DNA
<213> ORGANISM: Artificial sequence
<220> FEATURE:
<223> OTHER INFORMATION: Synthetic oligonucleotide
<220> FEATURE:

<221> NAME/KEY: modified_base
<222> LOCATION: (2),(5),(9),(16),(18)
<223> OTHER INFORMATION: m5c

<400> SEQUENCE: 132
gcaacagtct ggattctc 18

<210> SEQ ID NO 133
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (8),(9),(16)
<223> OTHER INFORMATION: m5c

<400> SEQUENCE: 133
gaggtgtcct tgttactg 18

<210> SEQ ID NO 134
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (9),(10),(17)
<223> OTHER INFORMATION: m5c

<400> SEQUENCE: 134
ggaggtgtcc ttgttact 18

<210> SEQ ID NO 135
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (10),(11),(18)
<223> OTHER INFORMATION: m5c

<400> SEQUENCE: 135
tggaggtgtc cttgttac 18

<210> SEQ ID NO 136
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (11),(12)
<223> OTHER INFORMATION: m5c

<400> SEQUENCE: 136
gtggaggtgt ccttgtta 18

<210> SEQ ID NO 137
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14),(15)
<223> OTHER INFORMATION: m5c

<400> SEQUENCE: 137
attgtggagg tgtccttg 18

<210> SEQ ID NO 138
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(15),(16)
<223> OTHER INFORMATION: m5c

<400> SEQUENCE: 138
cattgtggag gtgtcctt 18

<210> SEQ ID NO 139
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(17),(18)
<223> OTHER INFORMATION: m5c

<400> SEQUENCE: 139
gacattgtgg aggtgtcc 18

<210> SEQ ID NO 140
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(18)
<223> OTHER INFORMATION: m5c

<400> SEQUENCE: 140
ggacattgtg gaggtgtc 18

<210> SEQ ID NO 141
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(5)
<223> OTHER INFORMATION: m5c

<400> SEQUENCE: 141
cggacattgt ggaggtgt 18

<210> SEQ ID NO 142
<211> LENGTH: 18
<212> TYPE: DNA
<213> ORGANISM: Artificial sequence
<220> FEATURE:

<223> OTHER INFORMATION: Synthetic oligonucleotide
<220> FEATURE:
<221> NAME/KEY: modified_base
<222> LOCATION: (2),(6)
<223> OTHER INFORMATION: m5c

<400> SEQUENCE: 142
acggacattg tggaggtg 18

<210> SEQ ID NO 143
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(3),(7)
<223> OTHER INFORMATION: m5c

<400> SEQUENCE: 143
cacggacatt gtggaggt 18

<210> SEQ ID NO 144
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(4),(8)
<223> OTHER INFORMATION: m5c

<400> SEQUENCE: 144
ccacggacat tgtggagg 18

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(2),(4),(5),(7),(11)
<223> OTHER INFORMATION: m5c

<400> SEQUENCE: 145
cctccacgga cattgtgg 18

<210> SEQ ID NO 146
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(4),(6),(7),(9),(13)
<223> OTHER INFORMATION: m5c

<400> SEQUENCE: 146
ggcctccacg gacattgt 18

<210> SEQ ID NO 147
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(5),(7),(8),(10),(14)
<223> OTHER INFORMATION: m5c

<400> SEQUENCE: 147
tggcctccac ggacattg 18

<210> SEQ ID NO 148
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(11)
<223> OTHER INFORMATION: m5c

<400> SEQUENCE: 148
gtcatatggt cagggtat 18

<210> SEQ ID NO 149
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(12)
<223> OTHER INFORMATION: m5c

<400> SEQUENCE: 149
tgtcatatgg tcagggta 18

<210> SEQ ID NO 150
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(13)
<223> OTHER INFORMATION: m5c

<400> SEQUENCE: 150
atgtcatatg gtcagggt 18

<210> SEQ ID NO 151
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(14)
<223> OTHER INFORMATION: m5c

<400> SEQUENCE: 151
tatgtcatat ggtcaggg 18

<210> SEQ ID NO 152
<211> LENGTH: 18
<212> TYPE: DNA

<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(4),(5)
<223> OTHER INFORMATION: m5c

<400> SEQUENCE: 152
tgcccaggag tatagatg 18

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(6),(8),(12)
<223> OTHER INFORMATION: m5c

<400> SEQUENCE: 153
tacagcactt acggagtg 18

<210> SEQ ID NO 154
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4),(7),(9),(13)
<223> OTHER INFORMATION: m5c

<400> SEQUENCE: 154
ttacagcact tacggagt 18

<210> SEQ ID NO 155
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(13),(16)
<223> OTHER INFORMATION: m5c

<400> SEQUENCE: 155
gctatggatg tactacag 18

<210> SEQ ID NO 156
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(6),(7),(15)
<223> OTHER INFORMATION: m5c

<400> SEQUENCE: 156 aagaccettt gaggcttt 18

<210> SEQ ID NO 157
<211> LENGTH: 18

<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6),(7),(8),(16)
<223> OTHER INFORMATION: m5c

<400> SEQUENCE: 157
taagaccctt tgaggctt 18

<210> SEQ ID NO 158
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5),(7),(12),(14),(18)
<223> OTHER INFORMATION: m5c

<400> SEQUENCE: 158
gtagctcttg gcactagc 18

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(14)
<223> OTHER INFORMATION: m5c

<400> SEQUENCE: 159
tccgagatgt tttcta 16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 160
tcaaaagttt ccgaga 16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)
<223> OTHER INFORMATION: m5c

<400> SEQUENCE: 161
caactatacg actgag 16

<210> SEQ ID NO 162

-continued

<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 162
tcaggaagta gtgtgg 16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 163
ttcgggtaag tagatt 16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 164
gcactatctg ccaggg 16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(14)
<223> OTHER INFORMATION: m5c

<400> SEQUENCE: 165
gtcaatctag cagcat 16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(16)
<223> OTHER INFORMATION: m5c

<400> SEQUENCE: 166
cttcattgtg ttgggc 16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14),(15)
<223> OTHER INFORMATION: m5c

<400> SEQUENCE: 167
tatgatttta ggccca 16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(16)
<223> OTHER INFORMATION: m5c

<400> SEQUENCE: 168
tcagtttgga gtttac 16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14),(16)
<223> OTHER INFORMATION: m5c

<400> SEQUENCE: 169
gatttgtgtg ctcctc 16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(15),(16)
<223> OTHER INFORMATION: m5c

<400> SEQUENCE: 170
gctttcccat gctacc 16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14)
<223> OTHER INFORMATION: m5c

<400> SEQUENCE: 171
gctcactcct ggacaa 16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(16)
<223> OTHER INFORMATION: m5c

<400> SEQUENCE: 172
acgtgcgata atcttc 16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
agaaatgtaa gccggg 16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 174
gtcattagcg tgcata 16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 175
tgggatgtaa gcaaca 16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(14)
<223> OTHER INFORMATION: m5c

<400> SEQUENCE: 176
gactattgaa aggctg 16

<210> SEQ ID NO 177
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 177
atgccccact ctaata 16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14),(16)
<223> OTHER INFORMATION: m5c

<400> SEQUENCE: 178
tctggataca actcac 16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
agataggtcg ctcagg 16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(15)
<223> OTHER INFORMATION: m5c

<400> SEQUENCE: 180
gcagagatag gtcgct 16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(3)
<223> OTHER INFORMATION: m5c

<400> SEQUENCE: 181
cacggtaaag cactag 16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)

<223> OTHER INFORMATION: m5c

<400> SEQUENCE: 182
cagtggcacg gtaaag 16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14)
<223> OTHER INFORMATION: m5c

<400> SEQUENCE: 183
gaaacgccaa gtgctg 16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 184
taagttctcc ctgggc 16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14)
<223> OTHER INFORMATION: m5c

<400> SEQUENCE: 185
atgaacgtct ctgcag 16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
ttgacactat ttcagg 16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 187
atagcttgct caagac 16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14)
<223> OTHER INFORMATION: m5c

<400> SEQUENCE: 188
gctgcatgta tcacta 16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14)
<223> OTHER INFORMATION: m5c

<400> SEQUENCE: 189
gctaagtagg tgactt 16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
ttaggatgaa gctaag 16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)
<223> OTHER INFORMATION: m5c

<400> SEQUENCE: 191
ctgcactcgg ccctaa 16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
agattccaat tgtgag 16

<210> SEQ ID NO 193
<211> LENGTH: 16
<212> TYPE: DNA

<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(16)
<223> OTHER INFORMATION: m5c

<400> SEQUENCE: 193
agcctatcac cacgtc 16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(16)
<223> OTHER INFORMATION: m5c

<400> SEQUENCE: 194
cagcgtcacc caaatc 16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(16)
<223> OTHER INFORMATION: m5c

<400> SEQUENCE: 195
tacttagaag ggctgc 16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3)
<223> OTHER INFORMATION: m5c

<400> SEQUENCE: 196
gcctagtcac tttgat 16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14)
<223> OTHER INFORMATION: m5c

<400> SEQUENCE: 197
tcagggtaga tgtcaa 16

<210> SEQ ID NO 198
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 198
taggtgttca gggtag 16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
agtcaaagct aggtgt 16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14),(15),(16)
<223> OTHER INFORMATION: m5c

<400> SEQUENCE: 200
aatggatact ctgccc 16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(3),(16)
<223> OTHER INFORMATION: m5c

<400> SEQUENCE: 201
tccccaagct agatgc 16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(16)
<223> OTHER INFORMATION: m5c

<400> SEQUENCE: 202
acgtgtggtt tgcatc 16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)

<223> OTHER INFORMATION: m5c

<400> SEQUENCE: 203
gtcaaacgtg tggttt 16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
aggtgtcaaa cgtgtg 16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(14)
<223> OTHER INFORMATION: m5c

<400> SEQUENCE: 205
ctatttaagg tgtcaa 16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3),(14)
<223> OTHER INFORMATION: m5c

<400> SEQUENCE: 206
atcagactgc ctgcat 16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 207
gcacttacaa ggctgg 16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 208

-continued ggtgctgcta atatac 16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(14)
<223> OTHER INFORMATION: m5c

<400> SEQUENCE: 209
gcactaataa gcacta 16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2),(16)
<223> OTHER INFORMATION: m5c

<400> SEQUENCE: 210
tcatgcagcc tgttac 16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 211
aagcactagt tattgc 16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 212
tgcctgaccc tgttta 16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 213
agcttgataa ccttag 16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
gatgtagtag agtttt 16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (3)
<223> OTHER INFORMATION: m5c

<400> SEQUENCE: 215
agctgatgta gtagag 16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 216
gttggtttgt ggtact 16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 217
gtaggattct ggttac 16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 218
ataagtacct ttgatc 16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
gaaggtagcg aacatg 16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
ggtaactgct ccttaa 16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15),(16)
<223> OTHER INFORMATION: m5c

<400> SEQUENCE: 221
gtaactctgc acttcc 16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14),(16)
<223> OTHER INFORMATION: m5c

<400> SEQUENCE: 222
gaaagtaact ctgcac 16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)
<223> OTHER INFORMATION: m5c

<400> SEQUENCE: 223
cgagacctgg aaagta 16

<210> SEQ ID NO 224
<211> LENGTH: 16
<212> TYPE: DNA
<213> ORGANISM: Artificial sequence
<220> FEATURE:

<223> OTHER INFORMATION: Synthetic oligonucleotide
<220> FEATURE:
<221> NAME/KEY: modified_base
<222> LOCATION: (3),(14)
<223> OTHER INFORMATION: m5c

<400> SEQUENCE: 224
gtcatcccta tgtctt 16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 225
gtgttttggc tgtact 16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 226
agtctggatt ctctac 16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
atatggtcag ggtatg 16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
gagtatagat gctatg 16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 229
atgctatgga tgtact 16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
gagtattaca tgctat 16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (15)
<223> OTHER INFORMATION: m5c

<400> SEQUENCE: 231
tttctatttg agcacg 16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
gtatacagtt gaaggg 16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 233
gctgtaaggt tttgat 16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (14)
<223> OTHER INFORMATION: m5c

<400> SEQUENCE: 234
ggagacttgc ctgcat 16

<210> SEQ ID NO 235
<211> LENGTH: 16
<212> TYPE: DNA

-continued

<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 235
gtacgtatgt ttagtc 16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)
<223> OTHER INFORMATION: m5c

<400> SEQUENCE: 236
tcatggtggg tacgta 16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (16)
<223> OTHER INFORMATION: m5c

<400> SEQUENCE: 237
gtgtaaggga aacttc 16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1),(16)
<223> OTHER INFORMATION: m5c

<400> SEQUENCE: 238
cttgagggag tagtac 16

<210> SEQ ID NO 239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 239
tcgggtaagt agattttc 18

<210> SEQ ID NO 240
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 240
gaagtatctg taggccta 18

<210> SEQ ID NO 241
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 241
ggactgtata ggagatta 18

<210> SEQ ID NO 242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 242
ggttatagga tgcaggta 18

<210> SEQ ID NO 243
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 243
aggttatagg atgcaggt 18

<210> SEQ ID NO 244
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 244
gaagctaagt aggtgact 18

<210> SEQ ID NO 245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 245
tgaagctaag taggtgac 18

<210> SEQ ID NO 246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 246
cctagtcact ttgataga 18

<210> SEQ ID NO 247

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 247
ggaacatctt gagtaggt 18

<210> SEQ ID NO 248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 248
ggtgttcagg gtagatgt 18

<210> SEQ ID NO 249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 249
ggatactctg ccctgttc 18

<210> SEQ ID NO 250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 250
ggtgtcaaac gtgtggtt 18

<210> SEQ ID NO 251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 251
ccgtgtgcta gtatttgt 18

<210> SEQ ID NO 252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 252
tagtagagtt ttgcttgg 18

<210> SEQ ID NO 253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 253
gatgtagtag agttttgc 18

<210> SEQ ID NO 254
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 254
tgatgtagta gagttttg 18

<210> SEQ ID NO 255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 255
ctgatgtagt agagtttt 18

<210> SEQ ID NO 256
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 256
gcaagttggt ttgtggta 18

<210> SEQ ID NO 257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 257
tctaggcaat tgtggtgg 18

<210> SEQ ID NO 258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 258
gtaactctgc acttccca 18

<210> SEQ ID NO 259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 259
gtcatcccta tgtcttat 18

<210> SEQ ID NO 260
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 260
gtcatatggt cagggtat 18

<210> SEQ ID NO 261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 261
tgtcatatgg tcagggta 18

<210> SEQ ID NO 262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 262
atgtcatatg gtcagggt 18

<210> SEQ ID NO 263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 263
tatgtcatat ggtcaggg 18

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
tcagtttgga gtttac 16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
taagttctcc ctgggc 16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
atagcttgct caagac 16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
cagcgtcacc caaatc 16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
gtcaaacgtg tggttt 16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
ggtgctgcta atatac 16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
gtcatcccta tgtctt 16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
gtgttttggc tgtact 16

<210> SEQ ID NO 272
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9),(11),(13)
<223> OTHER INFORMATION: m5c

<400> SEQUENCE: 272
agataggtcg ctcaggag 18

<210> SEQ ID NO 273

<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10),(12),(14)
<223> OTHER INFORMATION: m5c

<400> SEQUENCE: 273
gagataggtc gctcagga 18

<210> SEQ ID NO 274
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (11),(13),(15)
<223> OTHER INFORMATION: m5c

<400> SEQUENCE: 274
agagataggt cgctcagg 18

<210> SEQ ID NO 275
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9)
<223> OTHER INFORMATION: m5c

<400> SEQUENCE: 275
taggtgttca gggtagat 18

<210> SEQ ID NO 276
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1),(10)
<223> OTHER INFORMATION: m5c

<400> SEQUENCE: 276
ctaggtgttc agggtaga 18

<210> SEQ ID NO 277
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2),(13),(16),(17),(18)
<223> OTHER INFORMATION: m5c

<400> SEQUENCE: 277
acgtgtggtt tgcatccc 18

<210> SEQ ID NO 278
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3),(14),(17),(18)
<223> OTHER INFORMATION: m5c

<400> SEQUENCE: 278
aacgtgtggt ttgcatcc 18

<210> SEQ ID NO 279
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4),(15),(18)
<223> OTHER INFORMATION: m5c

<400> SEQUENCE: 279
aaacgtgtgg tttgcatc 18

<210> SEQ ID NO 280
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5),(9)
<223> OTHER INFORMATION: m5c

<400> SEQUENCE: 280
gtgtcaaacg tgtggttt 18

<210> SEQ ID NO 281
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7),(11)
<223> OTHER INFORMATION: m5c

<400> SEQUENCE: 281
aggtgtcaaa cgtgtggt 18

<210> SEQ ID NO 282
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8),(12)
<223> OTHER INFORMATION: m5c

<400> SEQUENCE: 282
aaggtgtcaa acgtgtgg 18

-continued

```
<210> SEQ ID NO 283
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (9),(13)
<223> OTHER INFORMATION: m5c

<400> SEQUENCE: 283

taaggtgtca aacgtgtg                                               18


<210> SEQ ID NO 284
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (17)
<223> OTHER INFORMATION: m5c

<400> SEQUENCE: 284

aagttggttt gtggtact                                               18


<210> SEQ ID NO 285
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6),(8),(11),(13),(16),(17),(18)
<223> OTHER INFORMATION: m5c

<400> SEQUENCE: 285

agtaactctg cacttccc                                               18
```